(12) United States Patent
Bark et al.

(10) Patent No.: US 9,394,324 B2
(45) Date of Patent: Jul. 19, 2016

(54) FE(III) COMPLEX COMPOUNDS FOR THE TREATMENT AND PROPHYLAXIS OF IRON DEFICIENCY SYMPTOMS AND IRON DEFICIENCY ANEMIAS

(75) Inventors: Thomas Bark, Zürich (CH); Wilm Buhr, Constance (DE); Susanna Burckhardt, Zürich (CH); Michael Burgert, Friedrichshafen (DE); Camillo Canclini, St. Gallen (CH); Franz Dürrenberger, Dornach (CH); Felix Funk, Winterthur (CH); Peter Geisser, St. Gallen (CH); Aris Kalogerakis, Winterthur (CH); Simona Mayer, Bühler (CH); Erik Philipp, Arbon (CH); Stefan Reim, Stadel Winterthur (CH); Diana Sieber, Abtwill (CH); Jörg Schmitt, Thal (CH); Katrin Schwarz, St. Gallen (CH)

(73) Assignee: Vifor (International) AG, St. Gallen (CH)

( * ) Notice: Subject to any disclaimer, the term of this patent is extended or adjusted under 35 U.S.C. 154(b) by 720 days.

(21) Appl. No.: 13/583,276

(22) PCT Filed: Mar. 22, 2011

(86) PCT No.: PCT/EP2011/054315
§ 371 (c)(1),
(2), (4) Date: Nov. 20, 2012

(87) PCT Pub. No.: WO2011/117225
PCT Pub. Date: Sep. 29, 2011

(65) Prior Publication Data
US 2013/0109662 A1 May 2, 2013

(30) Foreign Application Priority Data

Mar. 23, 2010 (EP) .................................... 10157387

(51) Int. Cl.
| | |
|---|---|
| A61K 31/295 | (2006.01) |
| C07F 15/02 | (2006.01) |
| A61K 31/4453 | (2006.01) |
| A61K 31/555 | (2006.01) |
| A61K 45/06 | (2006.01) |

(52) U.S. Cl.
CPC ............. *C07F 15/025* (2013.01); *A61K 31/295* (2013.01); *A61K 31/4453* (2013.01); *A61K 31/555* (2013.01); *A61K 45/06* (2013.01)

(58) Field of Classification Search
CPC ............................ A61K 31/555; A61K 45/09
USPC ......................................... 514/186, 188, 502
See application file for complete search history.

(56) References Cited

U.S. PATENT DOCUMENTS

| | | |
|---|---|---|
| 6,121,287 A | 9/2000 | Björk et al. |
| 2005/0192315 A1 | 9/2005 | Jansson et al. |

OTHER PUBLICATIONS

Schutter et al., Tetrahedron, 1972;28(18):4871-5.*
Syamal "Ferric benzoylacetanilides," Canadian Journal of Chemistry, vol. 47, 1969, pp. 1693-1696.
International Search Report for corresponding PCT/EP2011/054315 mailed Jun. 8, 2011, three pages.
International Preliminary Report on Patentability for corresponding PCT/EP2011/054315 mailed Oct. 4, 2012, seven pages.

* cited by examiner

*Primary Examiner* — San-Ming Hui
(74) *Attorney, Agent, or Firm* — Rankin, Hill & Clark LLP

(57) ABSTRACT

The invention relates to iron(III) complex compounds and pharmaceutical compositions comprising them for the use as medicaments, in particular for the treatment and/or prophylaxis of iron deficiency symptoms and iron deficiency anemias.

5 Claims, No Drawings

FE(III) COMPLEX COMPOUNDS FOR THE TREATMENT AND PROPHYLAXIS OF IRON DEFICIENCY SYMPTOMS AND IRON DEFICIENCY ANEMIAS

INTRODUCTION

The invention relates to iron(III)-β-ketoamide complex compounds and pharmaceutical compositions comprising them for the use as medicaments, in particular for the treatment and/or prophylaxis of iron deficiency symptoms and iron deficiency anemias.

BACKGROUND

Iron is an essential trace element for almost all organisms and is relevant in particular with respect to growth and the formation of blood. The balance of the iron metabolism is in this case primarily regulated on the level of iron recovery from hemoglobin of ageing erythrocytes and the duodenal absorption of dietary iron. The released iron is taken up via the intestine, in particular via specific transport systems (DMT-1, ferroportin, transferrin, transferrin receptors), transferred into the circulation and thereby conveyed to the appropriate tissues and organs.

In the human body, the element iron is of great importance for oxygen transport, oxygen uptake, cell functions such as mitochondrial electron transport, and ultimately for the entire energy metabolism.

On average, the human body contains 4 to 5 g iron, with it being present in enzymes, in hemoglobin and myoglobin, as well as depot or reserve iron in the form of ferritin and hemosiderin.

Approximately half of this iron, about 2 g, is present as heme iron, bound in the hemoglobin of the erythrocytes. Since these erythrocytes have only a limited lifespan (75-150 days), new ones have to be formed constantly and old ones eliminated (over 2 million erythrocytes are being formed per second). This high regenerative capacity is achieved by macrophages phagocytizing the ageing erythrocytes, lysing them and thus recycling the iron thus obtained for the iron metabolism. The amount of iron of about 25 mg required daily for erythropoiesis is thus provided for the main part.

The daily iron requirement of an adult human is between 0.5 to 1.5 mg per day, infants and women during pregnancy require 2 to 5 mg of iron per day. The daily iron loss, e.g. by desquamation of skin and epithelial cells, is low; increased iron loss occurs, for example, during menstrual hemorrhage in women. Generally, blood loss can significantly reduce the iron level since about 1 mg iron is lost per 2 ml blood. In a healthy human adult, the normal daily loss of iron of about 1 mg is usually replaced via the daily food intake. The iron level is regulated by absorption, with the absorption rate of the iron present in food being between 6 and 12%; in the case of iron deficiency, the absorption rate is up to 25%. The absorption rate is regulated by the organism depending on the iron requirement and the size of the iron store. In the process, the human organism utilizes both divalent as well as trivalent iron ions. Usually, iron(III) compounds are dissolved in the stomach at a sufficiently acid pH value and thus made available for absorption. The absorption of the iron is carried out in the upper small intestine by mucosal cells. In the process, trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or discharged into the blood by the transport protein ferroportin. Hepcidin plays a central role in this process because it is the most important regulating factor of iron uptake. The divalent iron transported into the blood by ferroportin is converted into trivalent iron by oxidases (ceruloplasmin, hephaestin), the trivalent iron then being transported to the relevant places in the organism by transferrin (see for example "Balancing acts: molecular control of mammalian iron metabolism". M. W. Hentze, *Cell* 117, 2004, 285-297.)

Mammalian organisms are unable to actively discharge iron. The iron metabolism is substantially controlled by hepcidin via the cellular release of iron from macrophages, hepatocytes and enterocytes.

In pathological cases, a reduced serum iron level leads to a reduced hemoglobin level, reduced erythrocyte production and thus to anemia.

External symptoms of anemias include fatigue, pallor as well as reduced capacity for concentration. The clinical symptoms of an anemia include low serum iron levels (hypoferremia), low hemoglobin levels, low hematocrit levels as well as a reduced number of erythrocytes, reduced reticulocytes and elevated levels of soluble transferrin receptors.

Iron deficiency symptoms or iron anemias are treated by supplying iron. In this case, iron substitution takes place either orally or by intravenous iron administration. Furthermore, in order to boost erythrocyte formation, erythropoietin and other erythropoiesis-stimulating substances can also be used in the treatment of anemias.

Anemia can often be traced back to malnutrition or low-iron diets or imbalanced nutritional habits low in iron. Moreover, anemias occur due to reduced or poor iron absorption, for example because of gastroectomies or diseases such as Crohn's disease. Moreover, iron deficiency can occur as a consequence of increased blood loss, such as because of an injury, strong menstrual bleeding or blood donation. Furthermore, an increased iron requirement in the growth phase of adolescents and children as well as in pregnant women is known. Since iron deficiency not only leads to a reduced erythrocyte formation, but thereby also to a poor oxygen supply of the organism, which can lead to the above-mentioned symptoms such as fatigue, pallor, reduced powers of concentration, and especially in adolescents, to long-term negative effects on cognitive development, a highly effective and well tolerated therapy is of particular interest.

Through using the Fe(III) complex compounds according to the invention, there is the possiblity of treating iron deficiency symptoms and iron deficiency anemias effectively by oral application without having to accept the large potential for side effects of the classical preparations, the Fe(II) iron salts, such as $FeSO_4$, which is caused by oxidative stress. Poor compliance, which often is the reason for the deficient elimination of the iron deficiency condition, is thus avoided.

PRIOR ART

A multitude of iron complexes for the treatment of iron deficiency conditions is known from the prior art.

A very large proportion of these complex compounds consists of polymer structures. Most of these complex compounds are iron-polysaccharide complex compounds (WO20081455586, WO2007062546, WO20040437865, US2003236224, EP150085). It is precisely from this area that there are medicaments available on the market (such as Maltofer, Venofer, Ferinject, Dexferrum, Ferumoxytol).

Another large portion of the group of the polymer complex compounds is comprised of the iron-peptide complex compounds (CN101481404, EP939083, JP02083400).

There are also Fe complex compounds described in the literature that are structurally derived from macromolecules such as hemoglobin, chlorophyll, curcumin and heparin (US474670, CN1687089, Biometals, 2009, 22, 701-710).

Moreover, low-molecular Fe complex compounds are also described in the literature. A large number of these Fe complex compounds comprises carboxylic acid and amino acids as ligands. In this case, the focus is on aspartate (US2009035385) and citrate (EP308362) as ligands. Fe complex compounds containing derivatized phenylalanine groups as ligands are also described in this context (ES2044777).

Furthermore, Fe complex compounds that are composed of monomeric sugar units or of a combination or monomeric and polymeric units are described in the literature (FR19671016).

Hydroxypyrone and hydroxypyridone Fe complex compounds are also described in the literature (EP159194, EP138420, EP107458). The corresponding 5-ring systems, the hydroxyfuranone Fe complex compounds, are also described in analogy thereto (WO2006037449).

Moreover, iron-cyclopentadienyl complex compounds are also described in the literature (GB842637).

Furthermore, β-ketoamides as Fe ligands are also described in the literature. However, the compounds were not proposed or used as medicaments, in particular for a treatment of iron deficiency conditions. These are ketoamide structural units that are a constituent of siderophores (JACS, 2008, 130, 2124-2125). Furthermore, hexadentate ferric aerobactin complex compounds (*Inorg. chem.* 2006, 45, 6028-6033) were described. Moreover, tripodal Fe ligands with β-ketoamide structural units are disclosed in the literature (*Inorg. chem.* 1990, 29, 4096-9).

Furthermore, β-ketoamides as Fe ligands which carry aromatic groups on the amide or the ketone and are present as Fe(III) complexes are described in the literature (*Journal of the Chemical Society of Pakistan*, 1991, 13, 79-83; *Indian Journal of Chemistry*, 1981, 20A, 372-4; *Journal of Inorganic and Nuclear Chemistry*, 1973, 35, 1397-400; *Can J Chem*, 1969, 47, 1693-6; *Indian Journal of Chemistry*, 1968, 6, 516-20).

Moreover, β-ketoamides as Fe(II) ligands containing pyridin groups (*Journal of Inorganic and Nuclear Chemistry*, 1967, 29, 2484-6), benzyloxazolidinones or substituted sultam groups (Polyhedron, 1995, 14, 1397-9) are described in the literature.

US2005/0192315 describes salts of quinoline compounds which are stabilized against the neutral forms of the quinoline compounds (see Sections 2 and 3). Among the salts there is also the N-ethyl-N-phenyl-5-chloro-1,2-dihydro-4-hydroxy-1-methyl-2-oxo-3-quinolinecarboxamide iron (III) salt. The document mentions also pharmaceutical compositions. However, throughout the document no specific medical indication is mentioned, let alone supported by any data. A medical use of iron (III)-β-ketoamide complex compounds is therefore not taught in this document. As far as a medical use of N-ethyl-N-phenyl-5-chloro-1,2-dihydro-4-hydroxy-1-methyl-2-oxo-3-quinolinecarboxamide iron (III) salt should be taught by this document, it is excluded from the present invention. In Syamal, A.: "Ferric benzoylacetanilides" Canadian Journal of Chemistry, 47 (10), 1969, 1693-6, only the synthesis and spectroscopic properties of individual benzoylacetanilide-iron complex compounds is described.

The use of these complexes for the treatment and prophylaxis of iron deficiency symptoms and iron deficiency anemias is described in none of the passages cited in the text above.

Iron salts (e.g. iron(II) sulfate, iron(II) fumarate, iron(III) chloride, iron(II) aspartate, iron(II) succinate) are another important constituent for the treatment of iron deficiency symptoms and iron deficiency anemias.

These iron salts are very problematic in that, in part, they are highly incompatible (up to 50%) in the form of nausea, vomiting, diarrhea and also obstipation and cramps. Moreover, free iron(II) ions which catalyze the formation (inter alia Fenton reaction) of reactive oxygen species (ROS) occur during the use of these iron(II) salts. These ROS cause damage to DNA, lipids, proteins and carbohydrates which has far-reaching effects in cells, tissue and organs. This complex of problems is known and, in the literature, is largely considered the cause for the high incompatibility and referred to as oxidative stress.

OBJECT

The object of the present invention lay in developing new therapeutically effective compounds that can be used for an effective therapy for the preferably oral treatment of iron deficiency symptoms and iron deficiency anemias. In this case, these iron complexes were supposed to exhibit significantly fewer side effects than the classically used Fe(II) salts. Furthermore, these iron complexes, in contrast to the known polymeric iron complex compounds, were, if possible, supposed to have a defined structure (stoichiometry) and be preparable by simple synthesis processes. This goal was achieved by the development of novel Fe(III) complex compounds.

Furthermore, the novel iron complexes were supposed to be designed such that they are taken up into the intestinal cells directly via the membrane in order thus to release their complex-bound iron directly to the ferritin or the transferrin or to reach the bloodstream directly as an intact complex. Because of their properties, these new complexes are supposed to virtually not lead to the occurrence of high concentrations of free iron ions. For it is precisely the free iron ions that lead to the occurrence of ROS which are ultimately responsible for the side effects that occur.

In order to be able to meet these requirements, the inventors developed new Fe(III) complex compounds with a molecular weight that is not too large, medium lipophila and an optimal complex stability.

DESCRIPTION OF THE INVENTION

The inventors found that Fe(III) complex compounds with β-ketoamide ligands were particularly suitable for the above-described requirements. It was possible to demonstrate that these Fe complex compounds exhibited a high iron uptake, whereby a quick therapeutic success in the treatment of iron deficiency anemia could be achieved. Especially in comparison to iron salts, the complex compounds according to the invention exhibited a faster and higher utilization. Furthermore, these new systems have significantly reduced side effects than the classically used iron salts since there is no noteworthy occurrence of free iron ions in this case. The complex compounds according to the invention exhibit almost no oxidative stress since there is no formation of free radicals. Thus, significantly fewer side effects occur in the case of these complex compounds than in the case of the Fe salts known from the prior art. The complex compounds exhibit good stability at various pH value ranges. The complex compounds can be prepared well and are optimally suitable for the formulation of medicaments, in particular for oral administration.

Thus, the subject matter of the invention are iron(III)-β-ketoamide complex compounds or their pharmaceutically acceptable salts for use as medicaments. Subject matter of the invention are therefore also iron (III)-β-ketoamide complex compounds or their pharmaceutically acceptable salts for use in a method for therapeutic treatment of the human or animal body.

The iron(III)-β-ketoamide complex compounds in particular include such compounds which comprise the following structural element:

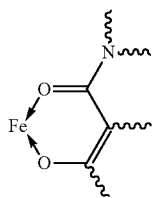

or its mesomeric resonance formula:

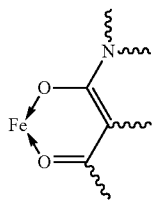

wherein ⁓⁓⁓ respectively is a substituent saturating the free valence and the arrows respectively represent coordinate bonds. Formally, a β-ketoamide ligand carries a negative charge and iron a positive charge (i.e., in the case of three β-ketoamide ligands, the iron formally has the oxidation number +3). Furthermore, it is clear to the person skilled in the art that a delocalization of the electrons occurs in the β-ketoamide ligand.

According to the invention, iron(III)-β-ketoamide complex compounds are also comprised in which the β-ketoamide ligand forms a bridge between different iron atoms:

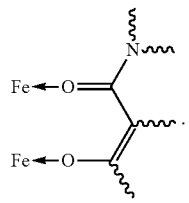

According to the invention, in particular bidentate β-ketomide ligands are preferred in which the bonding to the iron atom occurs via the two oxygen atoms of the β-keto structural unit. Though higher-dentate β-ketoamide ligands such as tridentate, tetradentate, pentadentate or even hexadentate β-ketoamide ligands are comprised in the present invention, they are less preferred due to their high complex stability (chelate effect) because possibly, iron is not released in a sufficient extent in the body due to the complex stabilities being too high. Higher-dentate β-ketoamide ligands are in particular those which, besides the two oxygen atoms of the β-ketoamide structure, comprise further functional coordinating groups, which are present, for example, in the substituent groups $R^1$ to $R^4$ explained below. These can be, for example, oxygen or nitrogen-containing functional groups, such as hydroxy, amino or the like.

The iron(III)-β-ketoamide complex compounds according to the invention include, in particular, such complex compounds that have at least one, preferably bidentate, β-ketoamide ligand bonded to one or two different iron atoms, as shown above.

Iron(III)-β-ketoamide complex compounds are preferred which exclusively comprise preferably bidentate β-ketoamide ligands that can be the same or different.

Furthermore, iron(III)-β-ketoamide complex compounds are particularly preferred which exclusively comprise the same, preferably bidentate β-ketoamide ligands.

According to the invention, however, also such complex compounds are comprised, which, besides the β-ketoamide ligand, preferably have one or more (such as two or three) mono- or polydentate ligands that are the same or different, such as, for example, carboxylic acid or carboxylate ligands (R—COOH bzw. RCOO⁻), alcohol ligands (R—OH), such as carbohydrate ligands, primary or secondary amino ligands (R—$NH_2$, R—NHR), imino ligands (R=NH), oximo ligands (R=N—OH), hydroxy ligands (OH or $H_2O$), ether ligands, or halogen ligands. Such complex compounds can also occur intermediately during the breakdown in the body, that is, in particular in an aqueous solution and, if applicable, in that case also intermediately coordinatively unsaturated.

In the iron(III)-β-ketoamide complex compounds according to the invention, the coordination number of the iron atoms is generally six (6), with the coordinating atoms generally being arranged octahedrally.

Furthermore, mono- or polynuclear iron(III)-β-ketoamide complex compounds in which one or more (such as 2, 3 or 4) iron atoms are present are also comprised according to the invention. However, mononuclear iron(III)-β-ketoamide complex compounds in which a central iron atom is present are preferred.

Generally, 1-4 iron atoms and 2-10 ligands can be present in the iron(III)-(1-ketoamide complex compounds. Mononuclear iron(III)-β-ketoamide complex compounds with at least one preferably tri-, preferably bidentate β-ketoamide ligand are preferred.

The iron(III)-β-ketoamide complex compounds are generally present in neutral form. However, salt-like iron(III)-β-ketoamide complex compounds are also included, in which the complex has a positive or negative charge which is compensated, in particular, by pharmacologically compatible, substantially non-coordinating anions (such as, in particular, halogenides, such as chloride) or cations (such as, in particular, alkaline or alkaline-earth metal ions).

According to the invention, iron(III) complex compounds are particularly preferred that contain at least one ligand of the formula (I):

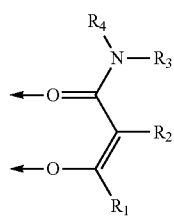

(I)

wherein
the arrows respectively represent a coordinate bond to one or different iron atoms,
$R_1$ is selected from the group consisting of optionally substituted alkyl, and optionally substituted alkoxycarbonyl,
$R_2$ is selected from the group consisting of hydrogen, optionally substituted alkyl, halogen and cyano, or
$R_1$ and $R_2$, together with the carbon atoms to which they are bonded, form an optionally substituted 5- or 6-membered ring, which may optionally contain one or more heteroatoms,
$R_3$ and $R_4$ are the same or different and are respectively selected from the group consisting of hydrogen, optionally substituted amino, and optionally substituted alkyl, or
$R_3$ and $R_4$, together with the nitrogen atom to which they are bonded, form an optionally substituted 3- to 6-membered ring, which may optionally contain one or more further heteroatoms,
or
$R_2$ and $R_3$ together form a saturated or unsaturated, optionally substituted 5- or 6-membered ring while forming a ligand of the formula (Ia):

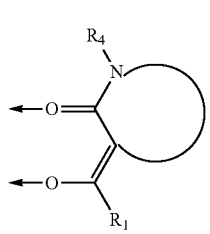

(Ia)

wherein $R_1$ and $R_4$ are defined as above,
or
$R_2$ and $R_3$ together form a saturated or unsaturated, optionally substituted 5- or 6-membered ring, and $R_1$ and $R_2$ together form a saturated or unsaturated, optionally substituted 5- or 6-membered ring, while forming a ligand of the formula (Ib):

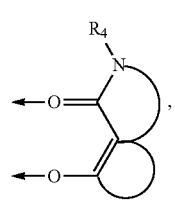

(Ib)

wherein $R_4$ is defined as above,
or pharmaceutically acceptable salts thereof.

Particularly preferred according to the invention are iron (III)-complex compounds comprising at least one ligand of formula (I):

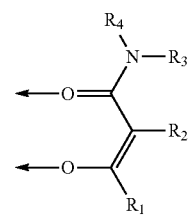

(I)

wherein
the arrows respectively represent a coordinate bond to one or different iron atoms,
$R_1$ is optionally substituted alkyl,
$R_2$ is selected from the group consisting of hydrogen, optionally substituted alkyl, halogen and cyano, or
$R_1$ and $R_2$, together with the carbon atoms to which they are bonded, form an optionally substituted 5- or 6-membered ring, which may optionally contain one or more heteroatoms,
$R_3$ and $R_4$ are the same or different and are respectively selected from the group consisting of hydrogen and optionally substituted alkyl, or
$R_3$ and $R_4$, together with the nitrogen atom to which they are bonded, form an optionally substituted 3- to 6-membered ring, which may optionally contain one or more further heteroatoms,
or, in another embodiment:
$R_2$ and $R_3$ together form a saturated or unsaturated, optionally substituted 5- or 6-membered ring while forming a ligand of the formula (Ia):

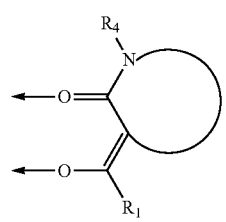

(Ia)

wherein $R_1$ and $R_4$ are defined as above,
or, in another embodiment:
$R_2$ and $R_3$ together form a saturated or unsaturated, optionally substituted 5- or 6-membered ring, and $R_1$ and $R_2$ together form a saturated or unsaturated, optionally substituted 5- or 6-membered ring, while forming a ligand of the formula (Ib):

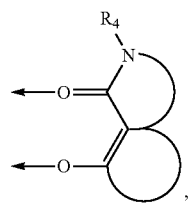

(Ib)

wherein $R_4$ is defined as above,
or pharmaceutically acceptable salts thereof.

A preferred embodiment of the invention relates to this iron(III) complex compounds, containing at least one ligand of the formula (I):

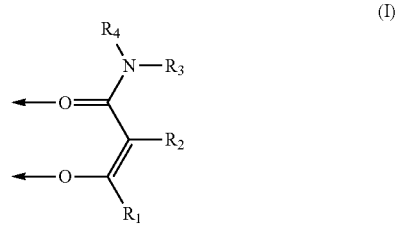

(I)

wherein
the arrows respectively represent a coordinate bond to one or different iron atoms,
$R_1$ is selected from the group consisting of optionally substituted alkyl, and optionally substituted alkoxycarbonyl, preferably optionally substituted alkyl,
$R_2$ is selected from the group consisting of hydrogen, optionally substituted alkyl, halogen and cyano, or
$R_1$ and $R_2$, together with the carbon atoms to which they are bonded, form an optionally substituted 5- or 6-membered ring, which may optionally contain one or more heteroatoms,
$R_3$ and $R_4$ are the same or different and are respectively selected from the group consisting of hydrogen, optionally substituted amino, and optionally substituted alkyl, preferably hydrogen and optionally substituted alkyl, or
$R_3$ and $R_4$, together with the nitrogen atom to which they are bonded, form an optionally substituted 3- to 6-membered ring, which may optionally contain one or more further heteroatoms.

Within the overall context of the invention, optionally substituted alkyl, in particular for the substituents $R_1$ to $R_4$, preferably includes:
Straight-chained or branched alkyl with 1 to 8, preferably 1 to 6 carbon atoms, cycloalkyl with 3 to 8, preferably 5 or 6 carbon atoms, or alkyl with 1 to 4 carbon atoms, which is substituted with cycloalkyl, wherein these alkyl groups can be optionally substituted.

The above-mentioned alkyl groups can optionally carry preferably 1 to 3 substituents, respectively.

These substituents are preferably selected from the group consisting of: hydroxy, optionally substituted aryl, in particular as defined below, optionally substituted heteroaryl, in particular as defined below, optionally substituted alkoxy, in particular as defined below, optionally substituted alkoxycarbonyl, in particular as defined below, optionally substituted acyl, in particular as defined below, halogen, in particular as defined below, optionally substituted amino, in particular as defined below, optionally substituted aminocarbonyl, in particular as defined below, and cyano.

Iron(III) complex compounds in which $R_1$, $R_2$, $R_3$ and/or $R_4$ represent aryl or heteroaryl-substituted alkyl groups are less preferred according to the invention.

Halogen includes, here and within the context of the present invention, fluorine, chlorine, bromine and iodine, preferably fluorine or chlorine.

In the above-defined alkyl groups, optionally one or more, more preferably 1 to 3 carbon atoms can furthermore be replaced with hetero-analogous groups that contain nitrogen, oxygen or sulfur. This means, in particular, that, for example, one or more, preferably 1 to 3, still more preferred one (1) methylene group ($—CH_2—$) can be replaced in the alkyl groups by $—NH—$, $—NR_5—$, $—O—$ or $—S—$, wherein $R_5$ is optionally substituted alkyl as defined above, preferably C1-C6 alkyl, such as methyl or ethyl, optionally substituted with 1 to 3 substituents, such as fluorine, chlorine, hydroxy, alkoxy.

Examples of alkyl residues having 1 to 8 carbon atoms include: a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3-dimethylhexyl group, a 4,4-dimethylhexyl group, a 5,5-dimethylhexyl group, a 1-propylpentyl group, a 2-propylpentyl group, etc. Those with 1 to 6 carbon atoms are preferred. Methyl, ethyl, n-propyl and n-butyl are most preferred.

Examples of alkyl groups produced by replacement with one or more hetero-analogous groups, such as $—O—$, $—S—$, $—NH—$ or $—N(R_5)—$ are preferably such groups in which one or more methylene groups ($—CH_2—$) are replaced with $—O—$ while forming an ether group, such as methoxymethyl, ethoxymethyl, 2-methoxyethyl etc. Therefore, the definition of alkyl also includes, for example, alkoxyalkyl groups as defined below, which are produced from the above-mentioned alkyl groups by replacement of a methylene group with $—O—$. If, according to the invention, alkoxy group are additionally permitted as substituents of alkyl, several ether groups can also be formed in this manner (such as a $—CH_2—O—CH_2—OCH_3$-group). Thus, according to the invention, polyether groups are also comprised by the definition of alkyl.

Examples of thio-containing alkyl radicals, especially as $R_4$ are:

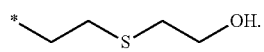

(* = binding site)

Cycloalkyl groups with 3 to 8 carbon atoms preferably include: a cyclopropyl group, a cyclobutyl group, a cyclopentyl group, a cyclohexyl group, a cycloheptyl group, a cyclooctyl group, etc. A cyclopropyl group, a cyclobutyl group, a cyclopentyl group and a cyclohexyl group are preferred. The cycloalkyl groups may optionally be substituted, preferably with 1 to 2 substituents such as hydroxyl, such as in the case of the 4-hydroxycyclohexyl, or C1-C6-alkoxycarbonyl, such as in the case of the following radicals:

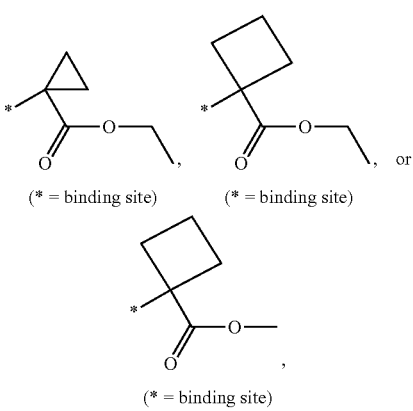

(* = binding site)  (* = binding site)

(* = binding site)

The definition of the optionally substituted alkyl also includes alkyl groups which are substituted by the above mentioned cycloalkyl groups, such as cyclopropylmethyl, cyclobutylmethyl, cyclopentylmethyl or cyclohexylmethyl.

Heterocyclic alkyl groups according to the invention are preferably those formed by the replacement of methylene with hetero-analogous groups from cycloalkyl, and include, for example, saturated 5 or 6-membered heterocyclic residues, which may be attached via a carbon atom or a nitrogen atom, and which preferably may have 1 to 3, preferably 2 heteroatoms, especially O, N, such as tetrahydrofuryl, azetidine-1-yl, substituted azetidinyl, such as 3-hydroxyazetidin-1-yl, pyrrolidinyl, such as pyrrolidin-1-yl, substituted pyrrolidinyl, such as 3-hydroxypyrrolidin-1-yl, 2-hydroxypyrrolidin-1-yl 2-methoxycarbonylpyrrolidin-1-yl, 2-ethoxycarbonylpyrrolidin-1-yl, 2-methoxypyrrolidin-1-yl, 2-ethoxypyrrolidin-1-yl, 3-methoxycarbonylpyrrolidin-1-yl, 3-ethoxycarbonylpyrrolidin-1-yl, 3-methoxypyrrolidin-1-yl, 3-ethoxypyrrolidine-1-yl, piperidinyl, such as piperidin-1-yl, piperidin-4-yl, substituted piperidinyl, such as 4-methyl-1-piperidyl, 4-hydroxy-1-piperidyl, 4-methoxy-1-piperidyl, 4-ethoxy-1-piperidyl, 4-methoxycarbonyl-1-piperidyl, 4-ethoxycarbonyl-1-piperidyl, 4-carboxy-1-piperidyl, 4-acetyl-1-piperidyl, 4-formyl-1-piperidyl, 1-methyl-4-piperidyl, 4-hydroxy-2,2,6,6-tetramethyl-1-piperidyl, 4-(dimethylamino)-1-piperidyl, 4-(diethylamino)-1-piperidyl, 4-amino-1-piperidyl, 2-(hydroxymethyl)-1-piperidyl, 3-(hydroxymethyl)-1-piperidyl, 4-(hydroxymethyl)-1-piperidyl, 2-hydroxy-1-piperidyl, 3-hydroxy-1-piperidyl, 4-hydroxy-1-piperidyl, morpholin-4-yl, substituted morpholinyl, such as 2,6-dimethyl morpholin-4-yl, piperazinyl, such as piperazin-1-yl, substituted piperazinyl, such as 4-methylpiperazin-1-yl, 4-ethylpiperazin-1-yl, 4-ethoxycarbonylpiperazin-1-yl, 4-methoxycarbonylpiperazin-1-yl, or tetrahydropyranyl, such as tetrahydropyran-4-yl, and which can optionally be condensated with aromatic rings, and which may optionally be substituted, such as with 1 to 2 substituents such as hydroxy, halogen, C1-C6-alkyl, etc. The definition of the optionally substituted alkyl groups thus includes also alkyl groups, which are substituted by the above-defined heterocyclic groups, such as 3-(1-piperidyl)propyl, 3-pyrrolidin-1-ylpropyl, 3-morpholinopropyl, 2-morpholinoethyl, 2-tetrahydropyran-4-ylethyl, 3-tetrahydropyran-4-ylpropyl, 3-(azetidin-1-yl)propyl etc.

Examples of a linear or branched alkyl group substituted with halogen and having 1 to 8 carbon atoms include, in particular:

a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a 1,2-difluoroethyl group, a 1,2-dichloroethyl group, a 1,2-dibromoethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptyl group, a 7-fluoroheptyl group, a 7-chloroheptyl group, a 7-bromoheptyl group, a perfluoroheptyl group, etc.

Examples of an alkyl group substituted with hydroxy include the above-mentioned alkyl residues, which have 1 to 3 hydroxy residues, such as, for example hydroxymethyl, 2-hydroxyethyl, 3-hydroxypropyl, 4-hydroxybutyl, 5-hydroxypentyl, 6-hydroxyhexyl, etc. and which possibly also may have other substituents such as alkoxycarbonyl or may have hetero atoms, such as sulfur, such as for example:

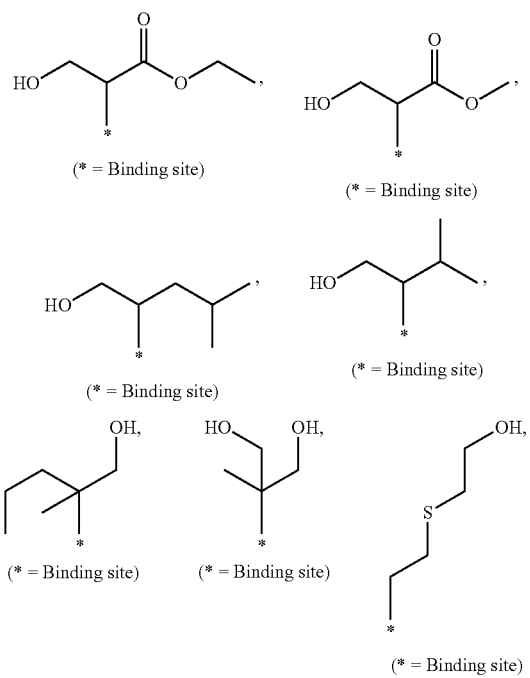

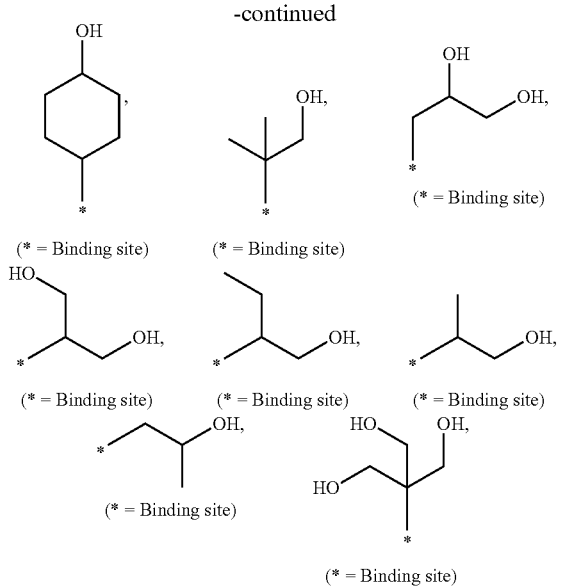

(* = Binding site)

which are also all examples of $R_3$ and/or $R_4$.

Optionally substituted aryl preferably includes according to the invention aromatic hydrocarbon residues with 6 to 14 carbon atoms (with no hetero atom in the aromatic ring system), for example: phenyl, naphthyl, phenanthrenyl and anthracenyl. The aforementioned aromatic groups optionally can preferably have one or more, preferably one, substituent, in particular halogen, hydroxy, alkyl, alkoxy, in each case as explained above or below. A preferred aromatic group is phenyl. A preferred alkyl substituted with an aromatic group (arylalkyl) is benzyl.

Optionally substituted aryl according to the present invention further includes optionally substituted heteroaryl, that is, heteroaromatic groups, such as for example: pyridyl, pyridyl-N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl. 5- or 6-membered aromatic heterocycles such as, for example pyridyl, pyridyl-N-oxide, pyrimidyl, pyridazinyl, furyl and thienyl are preferred. The aforementioned heteroaromatic groups can preferably have one or more, preferably one, substituent, in particular halogen, hydroxy, alkyl, alkoxy, in each case as explained above or below. Preferred examples of an alkyl substituted with a heteroaromatic group (hetarylalkyl) are methyl, ethyl, or propyl, in each case substituted with a heteroaromatic group, such as thienylmethyl, pyridylmethyl etc.

According to the invention, optionally substituted alkoxy (RO—) includes, for example, linear or branched alkoxy groups with up to 6 carbon atoms, such as a methoxy group, an ethoxy group, an n-propyloxy group, an i-propyloxy group, an n-butyloxy group, an i-butyloxy group, a sec-butyloxy group, a t-butyloxy group, an n-pentyloxy group, an i-pentyloxy group, a sec-pentyloxy group, a t-pentyloxy group, a 2-methylbutoxy group, an n-hexyloxy group, an i-hexyloxy group, a t-hexyloxy group, a sec-hexyloxy group, a 2-methylpentyloxy group, a 3-methylpentyloxy group, a 1-ethylbutyloxy group, a 2-ethylbutyloxy group, a 1,1-dimethylbutyloxy group, a 2,2-dimethylbutyloxy group, a 3,3-dimethylbutyloxy group, a 1-ethyl-1-methylpropyloxy group, etc. A methoxy group, an ethoxy group, an n-propyloxy group, an i-propyloxy group, an n-butyloxy group, an i-butyloxy group, a sec-butyloxy group, a t-butyloxy group, etc., are preferred. The alkoxy groups may optionally be substituted, such as with the above possible substituents for alkyl.

Methoxy, ethoxy, n-propoxy, n-butoxy, etc. are preferred alkoxy.

Accordingly, optionally substituted alkoxycarbonyl (RO—CO—) groups are formally derived from the above alkyl groups by adding a —OC(O)— residue under formation of an optionally substituted alkyloxycarbonyl residue. In that regard reference can be made to the definition of the above-described alkyl groups. As an alternative optionally substituted alkoxycarbonyl (RO—CO—) groups are derived from the aforementioned alkoxy groups by the addition of a carbonyl group. Methoxycarbonyl, ethoxycarbonyl, n-propoxycarbonyl, n-butoxycarbonyl tert.-butoxycarbonyl etc. are preferred alkoxycarbonyl, which may all be substituted as the above defined alkyl groups.

Optionally substituted amino includes according to the invention preferably: amino (—NH₂), optionally substituted mono- or dialkylamino (RHN—, (R)₂N—) for which with regard to the definition of optionally substituted alkyl reference can be made to the above definition. Furthermore included are optionally substituted mono- or diarylamino groups or mixed optionally substituted alkylarylamino groups, for which as regards the definition of optionally substituted alkyl or aryl reference can be made to the above definitions. Such groups include, for example methylamino, dimethylamino, ethylamino, hydroxyethylamino, such as 2-hydroxyethylamino, diethylamino, phenylamino, methylphenylamino etc. Optionally substituted amino further includes an optionally substituted cyclic amino, such as optionally substituted 5 or 6-membered cyclic amino that may contain further hetero atoms such as N, O, S, preferably O. Examples of such cyclic amino groups include the above-mentioned nitrogen-containing heterocyclic groups bonded through a nitrogen atom, such as piperidin-1-yl, 4-hydroxypiperidin-1-yl, 2-(methoxycarbonyl)pyrrolidin-1-yl, pyrrolidin-1-yl, morpholin-4-yl, etc.

Optionally substituted acyl includes, within the scope of the invention aliphatic and aromatic acyl, wherein aliphatic acyl is, in particular, formyl and optionally substituted alkylcarbonyl, for which with regard to the definition of the optionally substituted alkyl reference can be made to the foregoing definition of optionally substituted alkyl. Aromatic acyl therefore includes an optionally substituted arylcarbonyl, for which with regard to the definition of the optionally substituted aryl reference can be made to the foregoing definition of optionally substituted aryl. Preferred acyl groups according to the invention include for example: formyl (—C(=O)H), acetyl, propionyl, butanoyl, pentanoyl, hexanoyl, and in each case the isomers thereof, and benzoyl. Substituents of acyl groups include the above mentioned substituents for alkyl and aryl, and accordingly it can be referred to the above definitions.

Optionally substituted aminocarbonyl according to the invention can be formally derived from the above defined optionally substituted amino by adding a carbonyl from ((R)₂N—C(=O)—), and accordingly reference can be made to the above definition of optionally substituted amino. Examples include, therefore, carbamoyl (H₂NC(=O)—), optionally substituted mono- or dialkylaminocarbonyl (RHNC(=O)—, (R)₂NC(=O)—) wherein reference can be made to the above definition of optionally substituted alkyl. Furthermore are included are optionally substituted mono- or diarylaminocarbonyl residues or mixed optionally substituted alkylarylaminocarbonyl radicals, wherein reference can be made to the above definitions of optionally substituted alkyl and aryl. Such groups include, for example methylaminocarbonyl, dimethylaminocarbonyl, ethylaminocarbonyl, diethylaminocarbonyl, phenylaminocarbonyl, methylphenylaminocarbonyl to etc.

According to the invention, iron(III) complex compounds are preferred that contain at least one ligand of the formula (I):

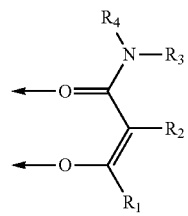

(I)

wherein
the arrows respectively represent a coordinate bond to one or different iron atoms, $R_1$ is alkyl, which can be optionally substituted with 1 to 3 substituents selected from the group consisting of hydroxy, alkoxy, ss defined above, in particular methoxy, ethoxy, halogen, cyano, alkoxycarbonyl, as defined above, such as especially methoxycarbonyl, ethoxycarbonyl, and aminocarbonyl as defined above, in particular carbamoyl, dimethylaminocarbonyl, or $R_1$ is alkoxycarbonyl that can be substituted by 1 to 3 substituents selected from the group consisting of hydroxy, C1-C6-alkoxy and halogen, in particular methoxycarbonyl, ethoxycarbonyl, propoxycarbonyl, etc., $R_2$ is selected from the group consisting of
  hydrogen,
  alkyl, which can be optionally substituted with 1 to 3 substituents selected from the group consisting of hydroxy, alkoxy, halogen, cyano and alkoxycarbonyl,
  halogen such as chlorine, fluorine, preferably fluorine and cyano or $R_1$ and $R_2$, together with the carbon atoms to which they are bonded, form an optionally substituted 5- or 6-membered ring, such as a cyclopentane ring or a cyclohexane ring which may optionally also contain one or more heteroatoms, and may have further substituents such as those mentioned for alkyl, $R_3$ and $R_4$ are the same or different and are respectively selected from the group consisting of hydrogen and alkyl, which can be optionally substituted with 1 to 3 substituents selected from the group consisting of hydroxy, alkoxy, halogen, cyano, optionally substituted amino and alkoxycarbonyl, and where alkyl may have one or more hetero atoms selected from —O— or —S— instead of —CH$_2$—, and/or $R_3$ and $R_4$ are selected from optionally substituted amino, as mentioned above, in particular, hydroxyethylamino, 4-morpholinyl, 1-piperidyl, 4-hydroxy-1-piperidyl, piperazin-1-yl, 4-methyl-1-yl.

In a preferred embodiment, only one of $R_3$ or $R_4$ is hydrogen.

Or $R_3$ and $R_4$, together with the nitrogen atom to which they are bonded, form an optionally substituted 3- to 6-membered ring, which may optionally contain one or more further heteroatoms, such as the above-mentioned optionally substituted via nitrogen bonded heterocycles.

Or, in another embodiment
$R_2$ and $R_3$ form together form a saturated or unsaturated, optionally substituted 5- or 6-membered ring while forming a ligand of the formula (Ia):

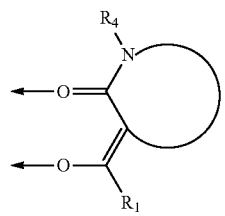

(Ia)

wherein $R_1$ and $R_4$ are defined as above, like for example realized in the following compounds:

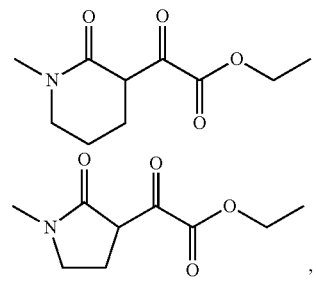

where the 5- or 6-membered ring systems may optionally be substituted, as for example by one to three substituents such as oxo, halogen, such as in the following example:

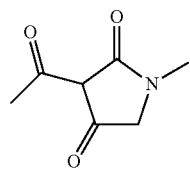

which carries oxo as a substituent,
or, in another embodiment
$R_2$ and $R_3$ together form a saturated or unsaturated, optionally substituted 5- or 6-membered ring, and $R_1$ and $R_2$ together form a saturated or unsaturated, optionally substituted 5- or 6-membered ring, while forming a ligand of the formula (Ib):

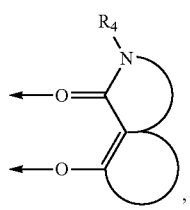

(Ib)

wherein $R_4$ is defined as above,
or pharmaceutically acceptable salts thereof.

The iron(III) complex compounds of the formula (II) are particularly preferred:

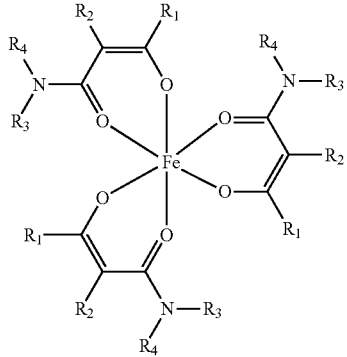

(II)

wherein $R_1$, $R_2$, $R_3$ and $R_4$ are respectively defined as above or preferably as below.

In a preferred embodiment of the invention, $R_1$ is selected from the group consisting of:

$C_{1-6}$-alkyl, preferably as presented above, optionally substituted with C1-4 alkoxy, as explained above, or with dialkylaminocarbonyl, also as explained above, $C_{3-6}$-cycloalkyl, preferably as presented above, $C_{3-6}$-cycloalkyl-$C_{1-4}$-alkyl, preferably as presented above, $C_{1-4}$-alkoxy-$C_{1-4}$-alkyl, preferably as presented above, hydroxy-$C_{1-4}$-alkyl, preferably as presented above, and halogen-$C_{1-4}$-alkyl, preferably as presented above, or $C_{1-4}$-alkoxycarbonyl, preferably as described above.

Particularly preferably, $R_1$ is $C_{1-6}$-alkyl, preferably as presented above, in particular methyl, ethyl, propyl, in particular n-propyl, and butyl, in particular n-butyl. Most preferably, $R_1$ is methyl, ethyl and n-butyl which are optionally substituted by $C_{1-6}$-alkoxy, such as methoxy or by di-$C_{1-6}$-alkylaminocarbonyl such as dimethylaminocarbonyl, or $R_1$ is C1-4 alkoxycarbonyl, especially methoxycarbonyl or ethoxycarbonyl.

In a preferred embodiment of the invention, $R_2$ is selected from the group consisting of:

hydrogen, halogen, preferably as presented above, $C_{1-6}$-alkyl, preferably as presented above, $C_{3-6}$-cycloalkyl, preferably as presented above, halogen-$C_{1-4}$-alkyl, preferably as presented above, and cyano.

Particularly preferably, $R_2$ is hydrogen, halogen, $C_{1-6}$-alkyl or Cyano, respectively preferably as presented above, still more preferably hydrogen, methyl and halogen, in particular chlorine or fluorine, most preferably hydrogen or fluorine.

In one embodiment of the invention, $R_1$ and $R_2$, together with the carbon atoms to which they are bonded, can form an optionally substituted 5- or 6-membered ring, which may optionally contain one or more (such as, in particular, 2) heteroatoms. In that case, β-ketoamide ligands of the following formula are present:

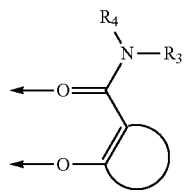

wherein $R_3$ and $R_4$ are as described above or below. However, this embodiment is less preferred.

In this embodiment, $R_1$ and $R_2$ together preferably represent a propylene (—$CH_2$—$CH_2$—$CH_2$—)— or a butylene (—$CH_2$—$CH_2$—$CH_2$—$CH_2$—)-group, in which one methylene group (—$CH_2$—), respectively, can be replaced with —O—, —NH—, or —$NR_5$—, wherein $R_5$ is optionally substituted alkyl, and wherein the groups formed by $R_1$ and $R_2$ can furthermore respectively be substituted by one to three substituents selected from the group consisting of hydroxy, $C_{1-4}$-alkoxy, amino and mono- or di-($C_{1-4}$-alkyl)amino. Exemplary ligands are the following:

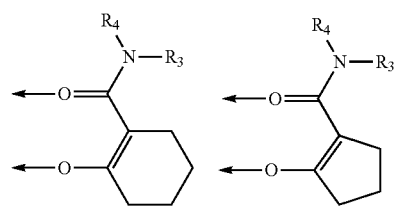

wherein $R_3$ and $R_4$ are respectively defined as above and wherein the rings may optionally carry 1 or 2 substituents such as oxo, alkyl or halogen.

In the invention, $R_3$ and $R_4$ are the same or different and are respectively selected from the group consisting of hydrogen, optionally substituted amino, and optionally substituted alkyl, preferably from hydrogen and optionally substituted alkyl, each as defined above.

Or $R_3$ and $R_4$, together with the nitrogen atom to which they are bonded, form an optionally substituted 3- to 6-membered ring, which may optionally contain one or more further heteroatoms each as defined above.

Preferably, $R_3$ and $R_4$ are the same or different and are respectively selected from the group consisting of:

hydrogen, and substituted or unsubstituted alkyl groups, such as selected from:

$C_{1-6}$-alkyl, preferably as presented above,

Di($C_{1-6}$-alkyl)amino-$C_{1-6}$-alkyl such as dimethyl- or diethylamino-$C_{1-6}$-alkyl, preferably as described above, Di($C_{1-6}$-alkyl)aminocarbonyl-$C_{1-6}$-alkyl such as aminocarbonyl-$C_{1-6}$-alkyl, or dimethyl- or diethylaminocarbonyl-$C_{1-6}$-alkyl, preferably as described above, $C_{3-6}$-cycloalkyl, preferably as presented above, $C_{3-6}$-cycloalkyl-$C_{1-4}$-alkyl, preferably as presented above, $C_1$-$C_4$-alkoxy-$C_{1-4}$-alkyl, preferably as presented above, $C_{1-3}$-alkoxycarbonyl-$C_{3-6}$-cycloalkyl, preferably as described above, $C_{1-3}$-alkoxycarbonyl-$C_{1-6}$-alkyl, preferably as presented above, hydroxy-$C_{1-4}$-alkyl, preferably as presented above, and halogen-$C_{1-4}$-alkyl, preferably as presented above, where possibly also more that one substituent can be present simultaneously on the alkyl, such as hydroxy and $C_{1-3}$-alkoxycarbonyl, or more hydroxyl groups, such as 2 to 3 hydroxyl groups, $C_{3-6}$-cycloalkyl also includes $C_{3-6}$-heterocyclyl, and where appropriate —$CH_2$— can be replaced by —S—, in each case as described above, or $R_3$ and $R_4$ together form an ethylene (—$CH_2$—$CH_2$—)—, propylene (—$CH_2$—$CH_2$—$CH_2$—)—, isopropylene (—$CH_2$—$CH(CH_3)$—)—, butylene (—$CH_2$—$CH_2$—$CH_2$—$CH_2$—)—, isobutylene-, pentylene (—$CH_2$—$CH_2$—$CH_2$—$CH_2$—$CH_2$—)—, or isopentylene group, in which in each case one methylene group (—$CH_2$—), respectively, can be replaced with —O—, —NH—, or —$NR_5$—, wherein $R_5$ is optionally substituted alkyl, and wherein the groups formed by $R_3$ and $R_4$ can furthermore respectively be substituted by one to three substituents selected from the group consisting of hydroxy, $C_{1-4}$-alkoxy, amino (—$NH_2$) and mono- or di($C_{1-4}$-alkyl)amino. Which means that $R_3$ and $R_4$ in this case, form an optionally substituted nitrogen-containing 5- to 6-membered heterocycle, such as the above or those indicated below.

Particularly preferably, $R_3$ and $R_4$ are the same or different and are selected from hydrogen, $C_{1-6}$-alkyl, preferably as presented above, in particular methyl, ethyl, propyl, in particular n-propyl, butyl, in particular n-butyl, pentyl, in particular n-pentyl and hexyl, in particular n-hexyl, and hydroxy-$C_{1-4}$-alkyl, preferably as presented above, and preferably hydroxymethyl, hydroxyethyl, $C_{1-3}$-alkoxycarbonyl-$C_{1-6}$-alkyl, preferably as presented above, and preferably methoxycarbonyl, ethoxycarbonyl, $C_{1-4}$-alkoxy-$C_{1-4}$-alkyl, as presented above.

Furthermore, in a preferred embodiment, $R_3$ and $R_4$ together form a pentylene (—$CH_2$—$CH_2$—$CH_2$—$CH_2$—$CH_2$—)— group, in which one methylene group (—$CH_2$—), respectively, can be replaced with —O—, —NH—, or —$NR_5$— (as defined above), and which can be respectively substituted by a substituent selected from hydroxy, $C_{1-4}$-alkoxy, amino (—$NH_2$) and mono- or di($C_{1-4}$-alkyl)amino. Examples of groups arising from $R_3$ and $R_4$ and the nitrogen atom to which they are bonded, are, for example the abovementioned via nitrogen bound heterocycles, which can optionally have 1 to 3, like 1 or 2 hetero atoms such as in particular O, N, such as azetidin-1-yl, substituted azetidinyl, such as 3-hydroxyazetidin-1-yl, pyrrolidinyl, such as pyrrolidin-1-yl, substituted pyrrolidinyl, such as 3-hydroxypyrrolidin-1-yl, 2-hydroxypyrrolidin-1-yl, 2-methoxycarbonylpyrrolidin-1-yl, 2-ethoxycarbonylpyrrolidin-1-yl, 2-methoxypyrrolidin-1-yl, 2-ethoxypyrrolidine-1-yl, 3-methoxycarbonylpyrrolidin-1-yl, 3-ethoxycarbonylpyrrolidin-1-yl, 3-methoxypyrrolidin-1-yl, 3-ethoxypyrrolidin-1-yl, piperidinyl, such as piperidin-1-yl, substituted piperidinyl such as 4-methyl-1-piperidyl, 4-hydroxy-1-piperidyl, 4-methoxy-1-piperidyl, 4-ethoxy-1-piperidyl, 4-methoxycarbonyl-1-piperidyl, 4-ethoxycarbonyl-1-piperidyl, 4-carboxy-1-piperidyl, 4-acetyl-1-piperidyl, 4-formyl-1-piperidyl, 4-hydroxy-2,2,6,6-tetramethyl-1-piperidyl, 4-(dimethylamino)-1-piperidyl, 4-(diethylamino)-1-piperidyl, 4-amino-1-piperidyl, 2-(hydroxymethyl)-1-piperidyl, 3-(hydroxymethyl)-1-piperidyl, 4-(hydroxymethyl)-1-piperidyl, 2-hydroxy-1-piperidyl, 3-hydroxy-1-piperidyl, morpholino-4-yl, substituted morpholinyl, such as 2,6-dimethyl morpholine-4-yl, piperazinyl, such as piperazin-1-yl, substituted piperazinyl, such as 4-methyl-piperazin-1-yl, 4-ethylpiperazin-1-yl, 4-ethoxycarbonylpiperazin-1-yl, 4-methoxycarbonylpiperazin-1-yl.

Particularly preferred are piperidin-1-yl, piperazin-1-yl, morpholin-4-yl which may optionally be substituted, such as by hydroxyl, such as 4-hydroxy-piperidin-1-yl. Even more preferred are 4-hydroxy-piperidin-1-yl and piperidin-1-yl.

In another less preferred embodiment of the invention, $R_2$ and $R_3$ together form a saturated or unsaturated, optionally substituted 5- or 6-membered ring while forming a β-ketoamide of the formula (Ia):

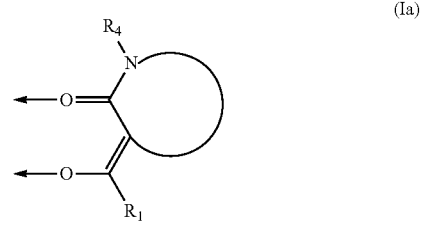

(Ia)

wherein $R_1$ and $R_4$ are defined as above. Examples for such ligands are compounds in which $R_2$ and $R_3$ together form an ethylene (—$CH_2$—$CH_2$—)— or propylene (—$CH_2$—$CH_2$—$CH_2$—)— group:

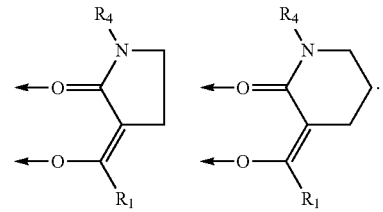

Ligands of this type are described, for example, in Korte et al., Chemische Berichte, 95, 2424 and Wamhoff et al., Liebigs Ann. Chem. 715, 23-34 (1968).

In another also less preferred embodiment of the invention, $R_2$ and $R_3$ together form a saturated or unsaturated, optionally substituted 5- or 6-membered ring, and $R_1$ and $R_2$ together form a saturated or unsaturated, optionally substituted 5- or 6-membered ring, while forming a β-ketoamide of the formula (Ib):

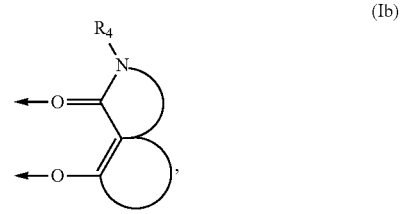

(Ib)

wherein $R_4$ is defined as above.

Examples of such ligands include:

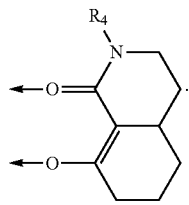

It is clear to the person skilled in the art that the ligands according to the invention

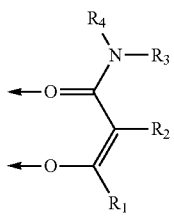

arise from the corresponding β-ketoamide compounds:

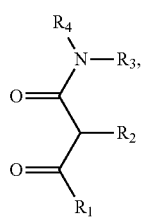

in which there is a keto-enol tautomerism, as is known:

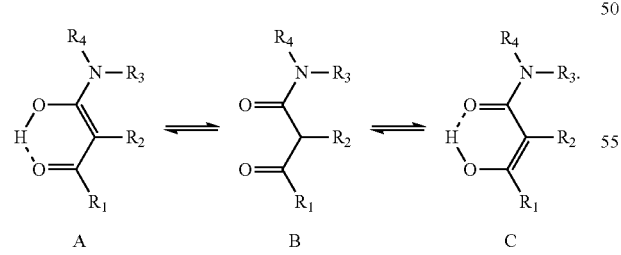

The mesomeric forms A and C are analytically indistinguishable. In the context of the present invention in each case, all forms are included, but in the context of the present invention the ligand in general, is only drawn in the keto form.

Formally, the ligand formally arises from the corresponding β-ketoamide compounds by abstraction of a proton.

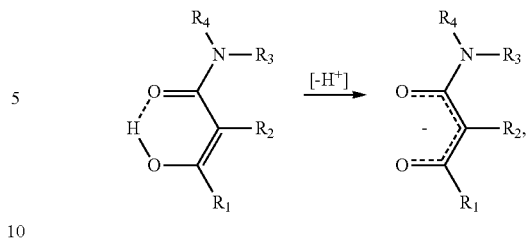

formally therefore carries a uninegative charge. Also for the iron complex compounds in the context of the present invention always only one of the localized resonance formulas is depicted:

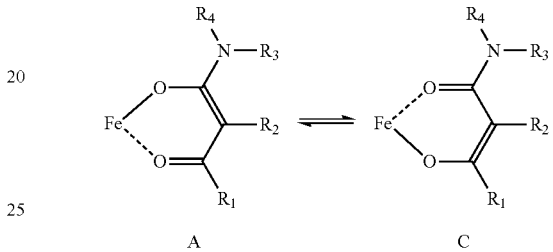

although due to the lower electron density at the amidic oxygen atom, is to be expected that the resonance formula C prevails. As explained above, an analytical distinction of the resonance formulas A and C is not possible.

Examples of the β-ketoamide ligands used in the present invention are shown below:

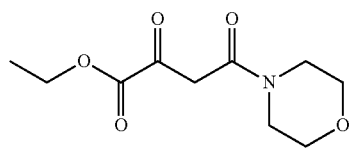

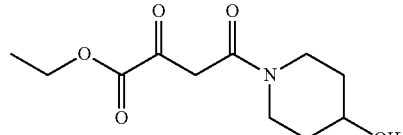

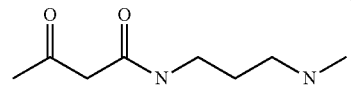

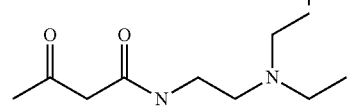

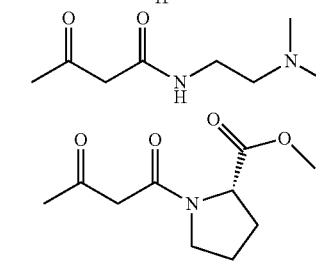

23
-continued
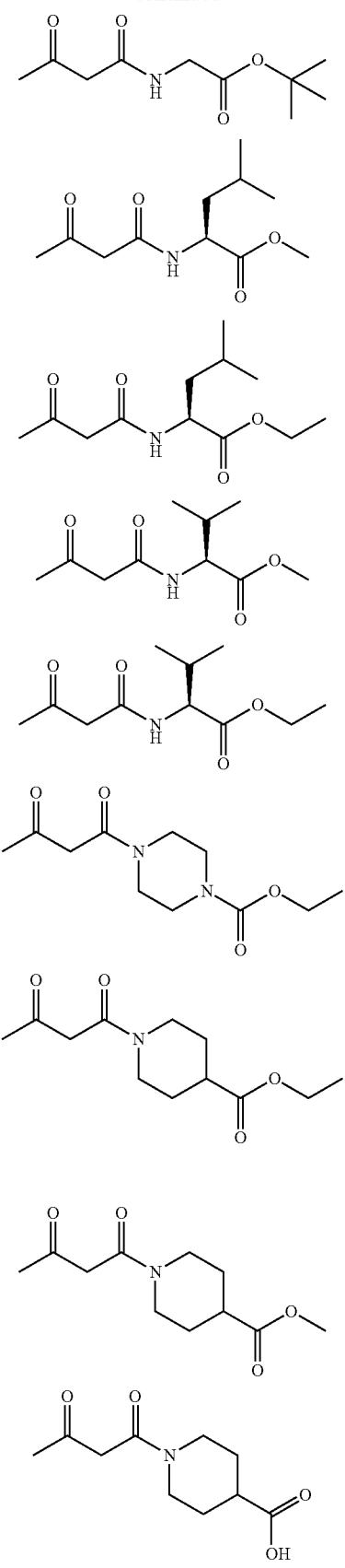
24
-continued
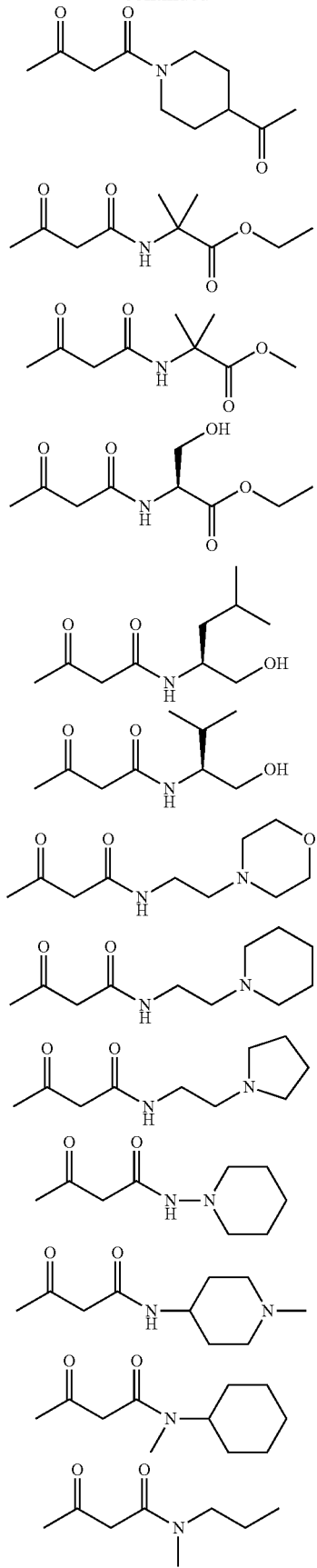

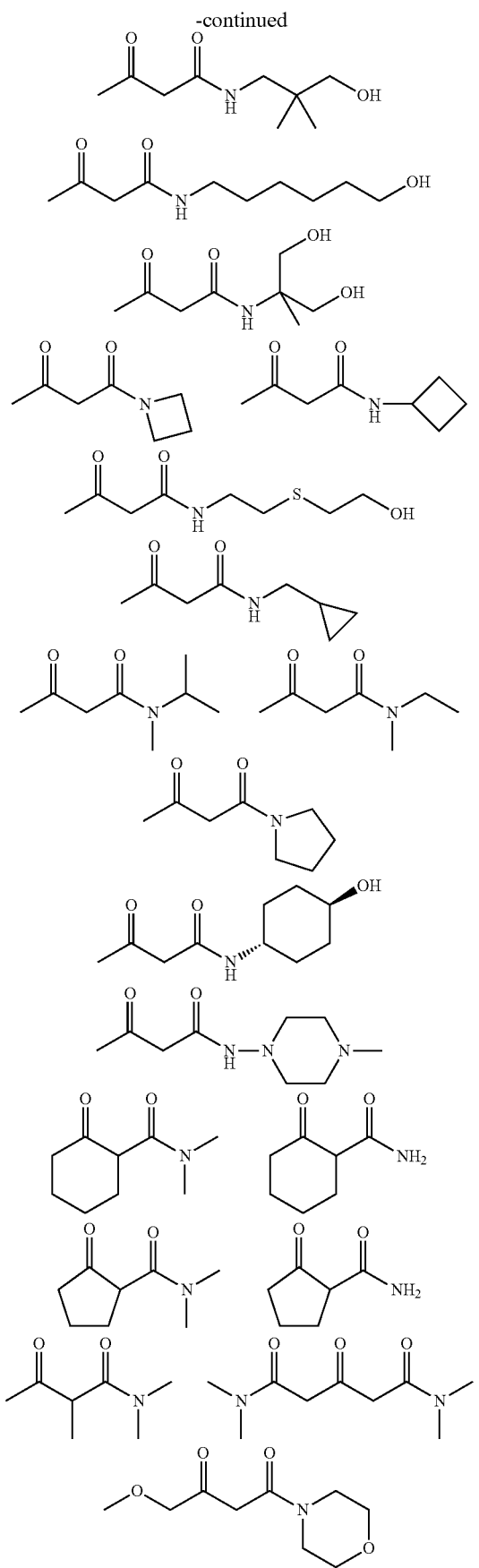
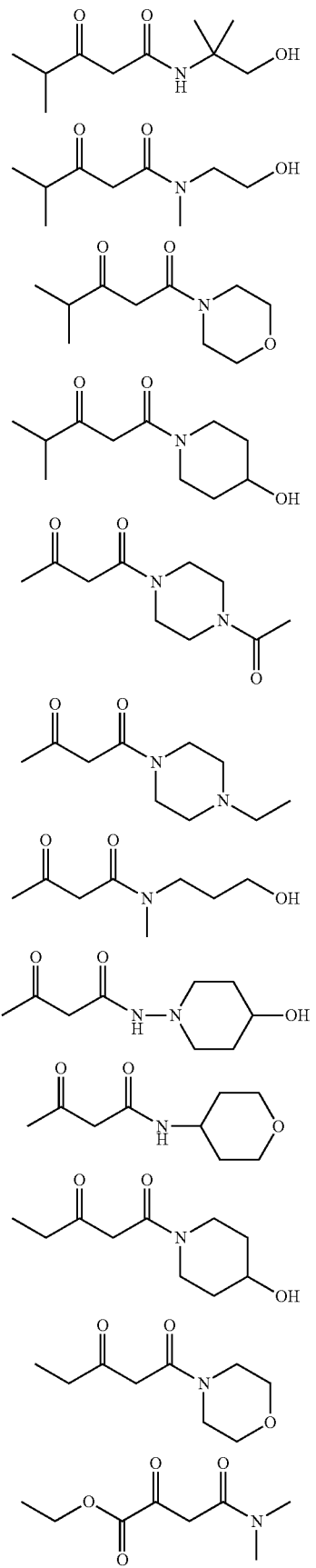

27
-continued
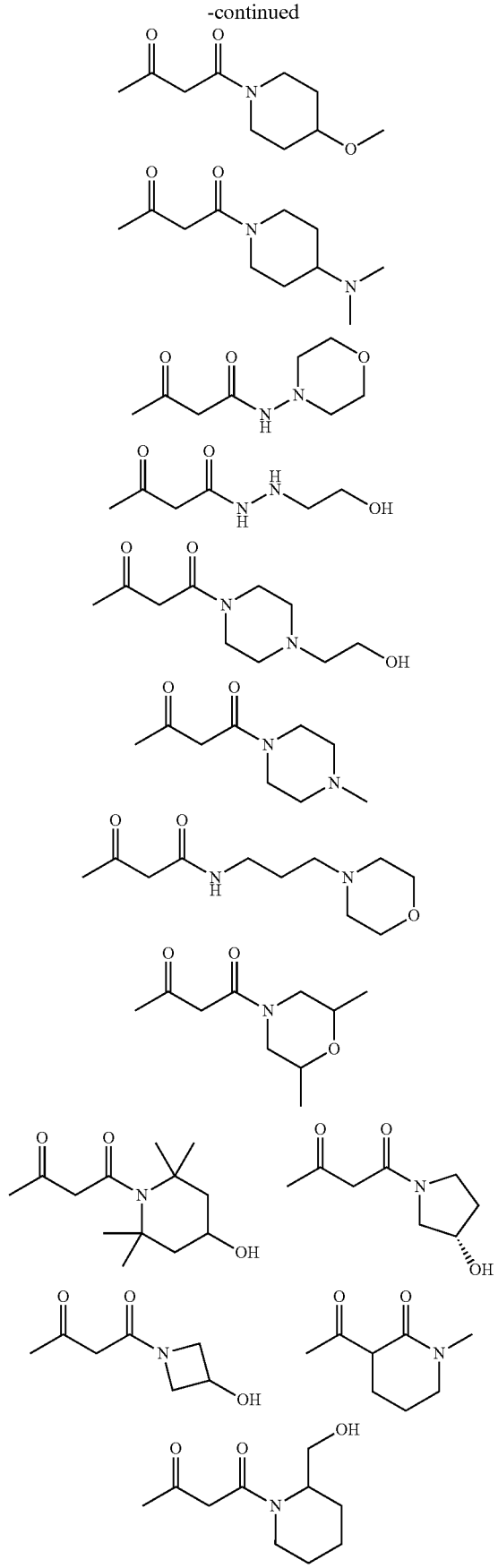
28
-continued
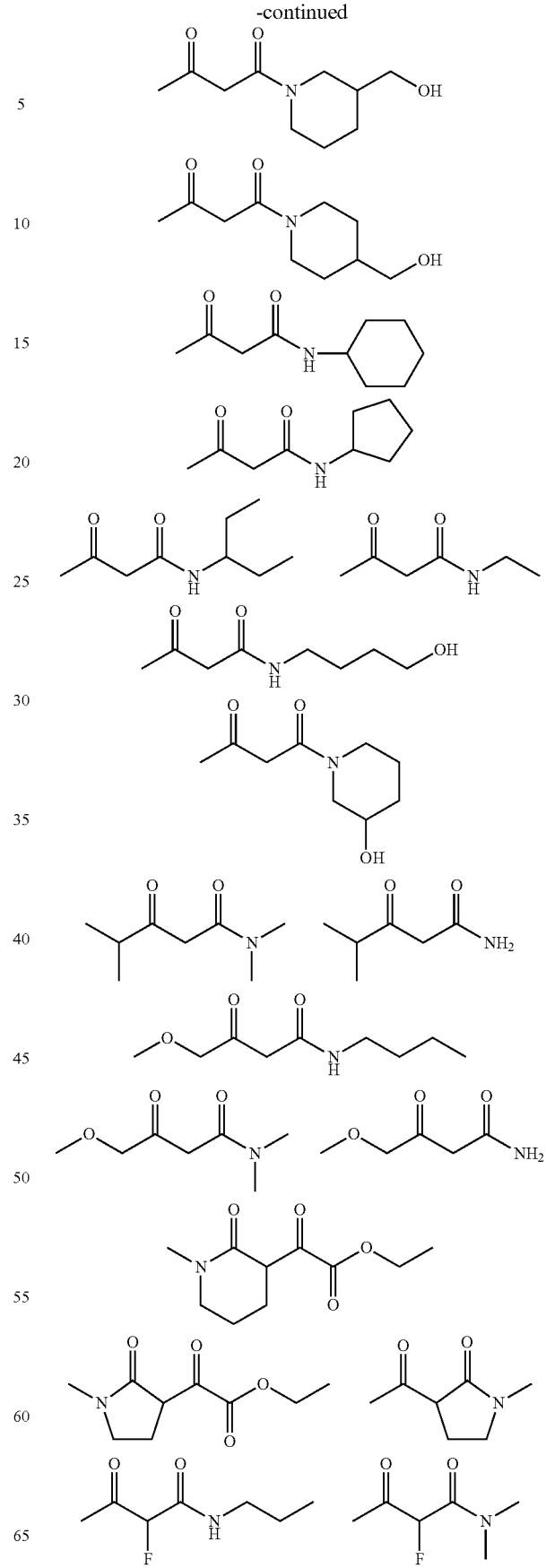

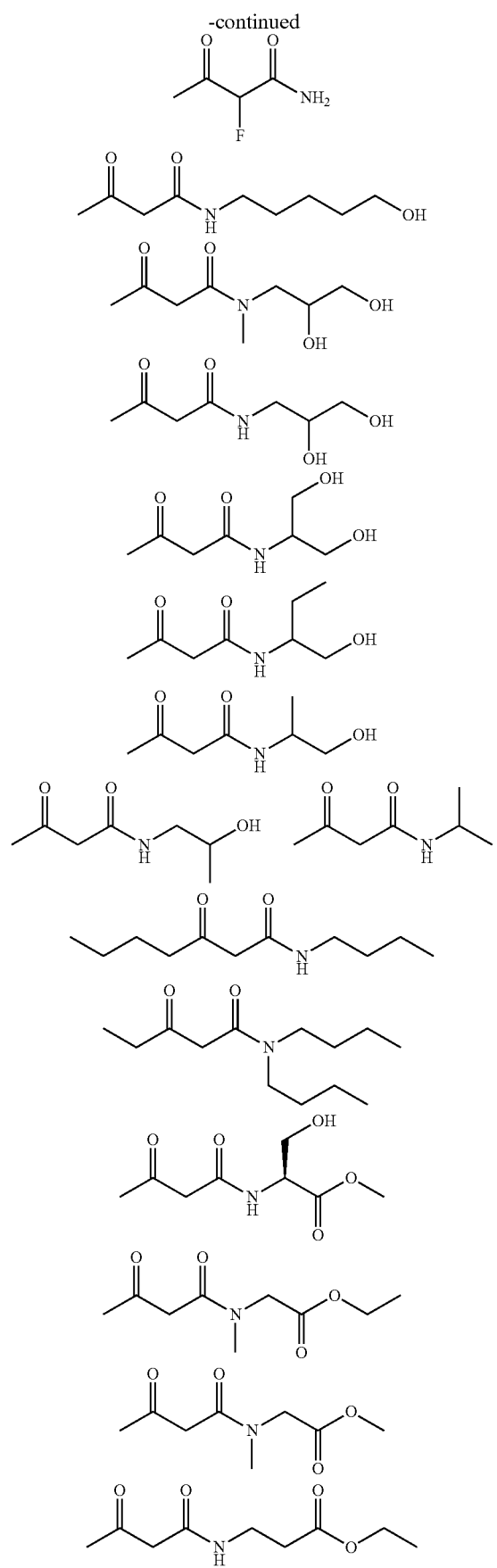
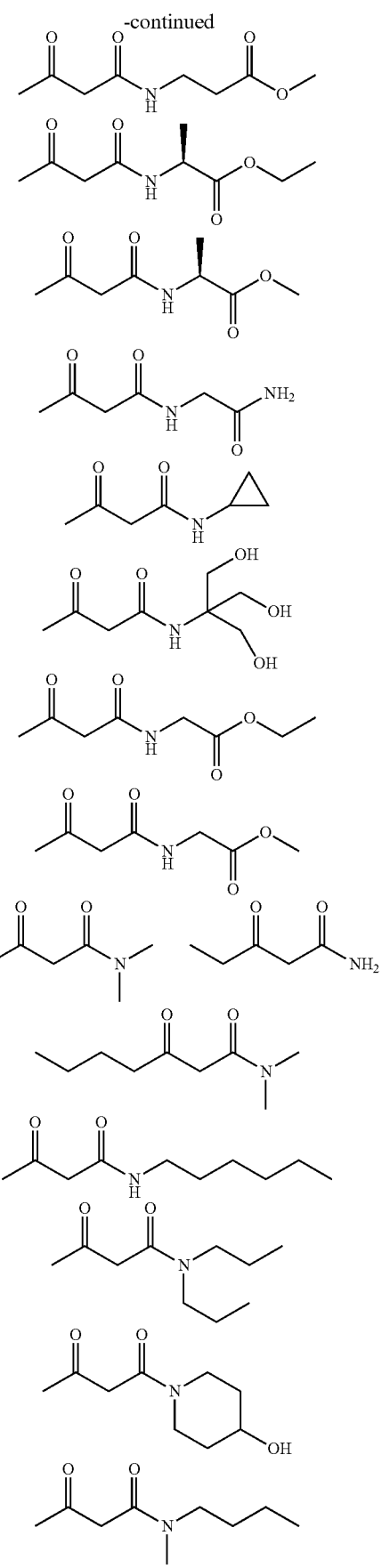

-continued
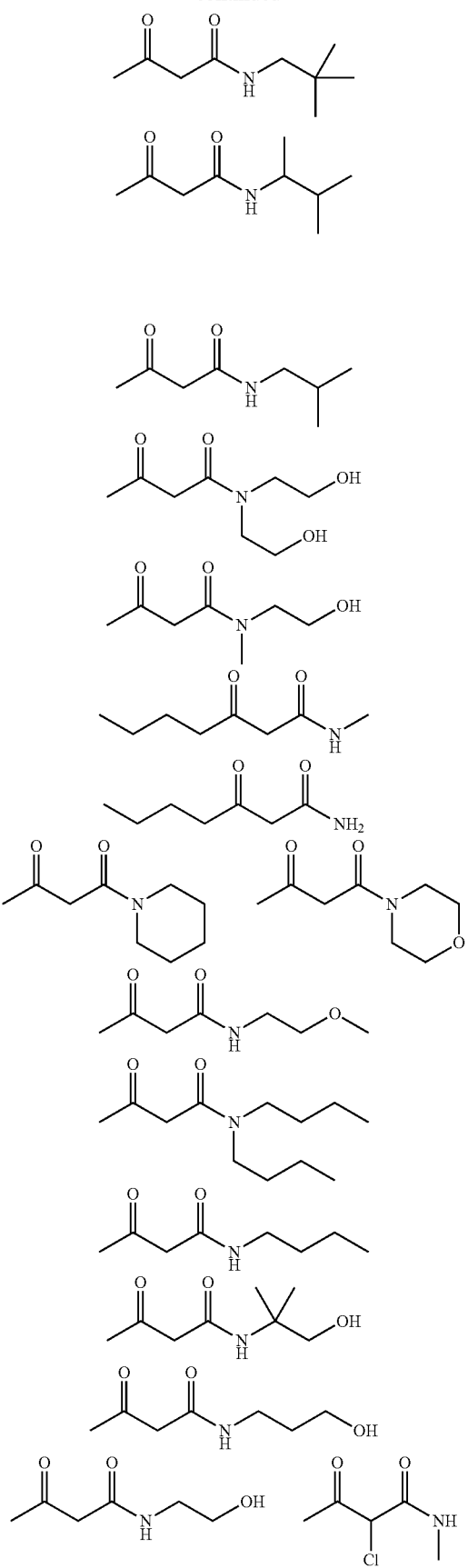
-continued
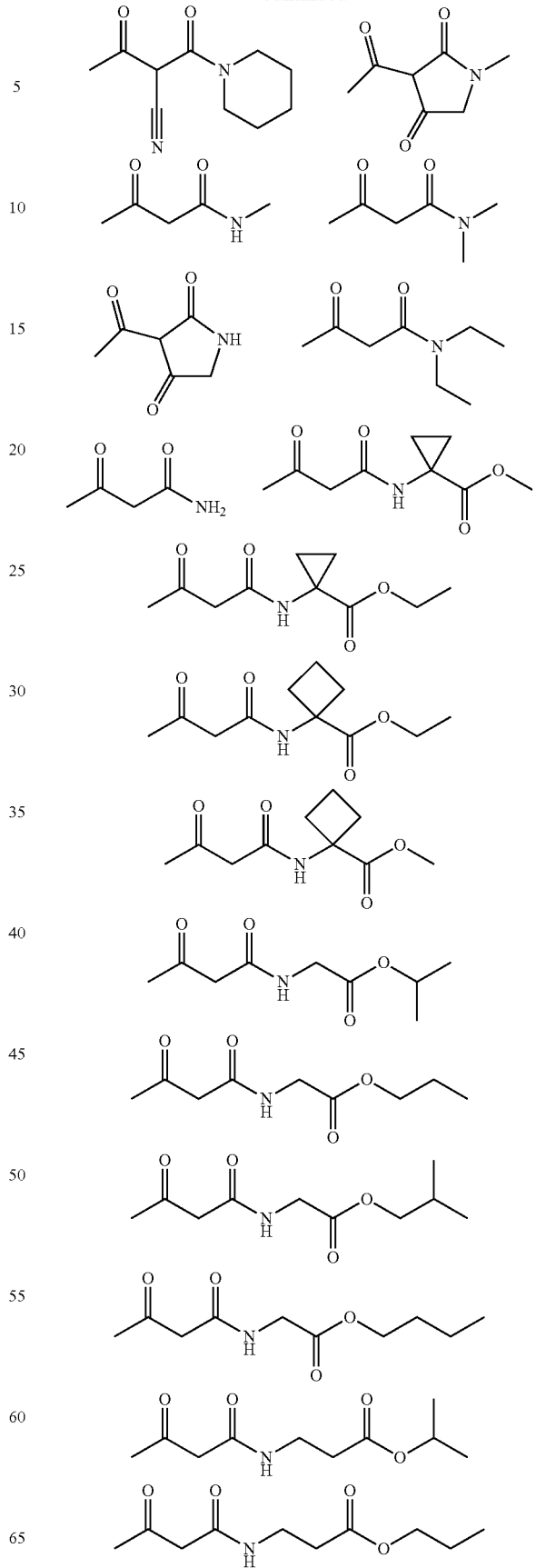

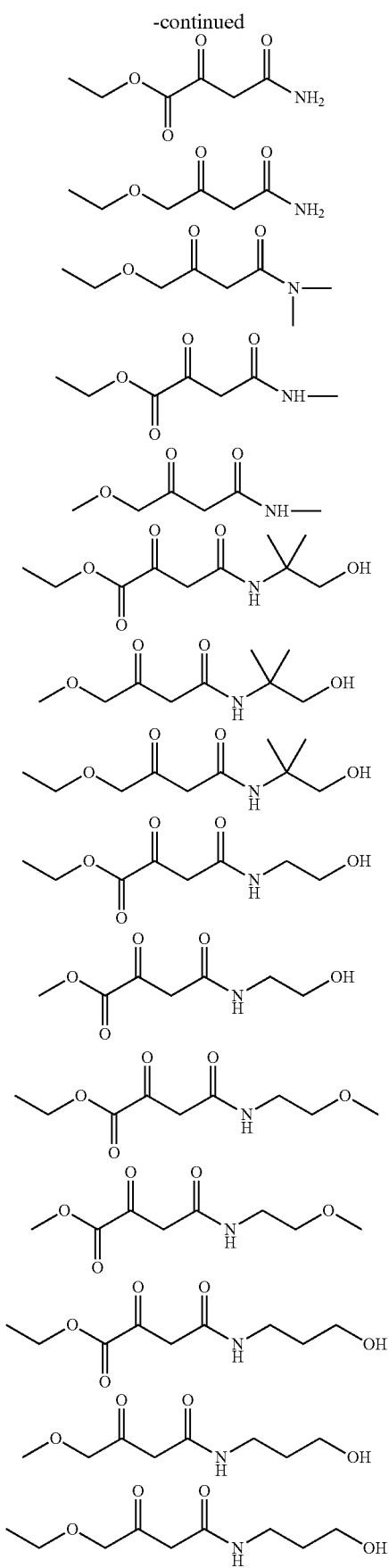
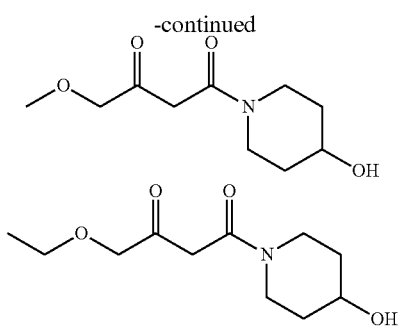

The iron(III)-β-ketoamide complex compounds, in particular of the general formula (II), can be present in the form or various isomers. Isomeric forms include, for example, regioisomers which differ in the position of the ligands relative to one another, including so-called optical isomers that have an image/mirror image relationship to one another. If asymmetric carbon atoms are present, the ligands can be present in the form or optical isomers which have a image/mirror image relationship to one another, and include pure enantiomers, mixtures of the enantiomers, in particular racemates. Enantiomerically pure ligands can be obtained, as is known to the person skilled in the art, by optical resolution methods, such as reaction with chiral reagents to form diastereomers, separation of the diastereomers and release of the enantiomers.

Furthermore, in particular the following are preferred embodiments of the invention:

(In the present invention, the digits 1-6 in "1-6C" or "$C_{1-6}$", or "1-4" in "1-4C" or "$C_{1-4}$" etc. in each case signify the number of the carbon atoms of the subsequent hydrocarbon group designations).

$R_1$ is selected from the group consisting of:
1-6C-alkyl, (i.e. alkyl with 1 to 6 carbon atoms),
3-6C-cycloalkyl,
3-6C-cycloalkyl-1-4C-alkyl,
1-4C-alkoxy-1-4C-alkyl,
hydroxy-1-4C-alkyl,
fluoro-1-4C-alkyl;

$R_2$ is selected from the group consisting of:
H,
1-6C-alkyl,
3-6C-cycloalkyl,
fluoro-1-4C-alkyl,
halogen,
cyano;

or $R_1$ and $R_2$ together form a propylene (—$CH_2$—$CH_2$—$CH_2$), butylene (—$CH_2$—$CH_2$—$CH_2$—$CH_2$—), azabutylene or oxabutylene group;

$R_3$ and $R_4$ are the same or different and are respectively selected from the group consisting of:
H,
1-6C-alkyl,
3-6C-cycloalkyl,
3-6C-cycloalkyl-1-4C-alkyl,
1-4C-alkoxy-1-4C-alkyl,
1-3C-alkoxy-carbonyl-1-6C-alkyl,
hydroxy-1-4C-alkyl,
fluoro-1-4C-alkyl;

or $R_3$ and $R_4$ together form an ethylene (—$CH_2$—$CH_2^+$, propylene (—$CH_2$—$CH_2$—$CH_2^+$, hydroxypropylene, preferably 2-hydroxypropylene, 3-methylpropylene, butylene (—$CH_2$—$CH_2$—$CH_2$—$CH_2$—), 2-hydroxybutylene, 2-methoxybutylene, isobutylene, pentylene (—$CH_2$—

$CH_2-CH_2-CH_2-CH_2-$), hydroxypentylene, preferably 3-hydroxypentylene, methoxypentylene, preferably 3-methoxypentylene, ethoxypentylene, preferably 3-ethoxypentylene, propoxypentylene, preferably 3-propoxypentylene, isopropoxypentylene, preferably 3-isopropoxypentylene, cyclopropoxypentylene, preferably 3-cyclopropoxypentylene, azapentylene in particular $-CH_2-CH_2-NH-CH_2-CH_2-$, or an oxapentylene group, in particular $-CH_2-CH_2-O-CH_2-CH_2-$
or pharmaceutically acceptable salts thereof.

Preferably, the aforementioned substituent groups are defined as follows:
1-6C-alkyl preferably includes straight-chained or branched alkyl groups with 1 to 6 carbon atoms. Examples therefor can be methyl, ethyl, n-propyl, iso-propyl, n-butyl, iso-butyl, sec-butyl, tert-butyl n-pentyl, iso-pentyl, neo-pentyl, n-hexyl, iso-hexyl and neo-hexyl.
3-6C-Cycloalkyl preferably includes cycloalkyl 1 to 6 carbon atoms, such as cyclopropyl, cyclobutyl, cyclopentyl, cyclohexyl.
3-6C-cycloalkyl-1-4C-alkyl preferably includes a 1-6C-alkyl group described above, substituted with a 3-6C-cycloalkyl group described above. Examples therefor can be a cyclopropylmethyl, cyclopentylmethyl and cyclohexylmethyl group.
1-3C-alkoxy-carbonyl-1-6C-alkyl, preferably includes a 1-6C-alkyl group described above, which is linked to a carbonyl group which is present with a 1-3C alkoxy group as a carboxylic acid ester. Examples therefor can be methoxycarbonylmethyl, ethoxycarbonylmethyl, methoxycarbonylethyl, ethoxycarbonylethyl and isopropoxycarbonylmethyl.
1-4C-alkoxy preferably includes a 1-4C-alkoxy group, in which an oxygen atom is connected to a straight or branched alkyl chain with 1-4 carbon atoms. Examples of this group can be methoxy, ethoxy, propoxy and isobutoxy.
1-4C-alkoxy-1-4C-alkyl preferably includes a 1-4C-alkoxy group described above, which is substituted with a 1-4C-alkyl group described above. Examples of this group can be methoxyethyl, ethoxypropyl, methoxypropyl, isobutoxymethyl.
Hydroxy-1-4C-alkyl includes a 1-4C-alkyl group described above, which is substituted with a hydroxy group. Examples therefor can be hydroxyethyl, hydroxybutyl and hydroxyisopropyl.
Fluoro-1-4C-alkyl includes a 1-4C-alkyl group described above, which is substituted with one to three fluorine atoms. Examples therefor can by trifluoromethyl and trifluoroethyl.
Halogen signifies F, Cl, Br, I.

The groups and residues can also contain chiral centers. In that case, all possible entantiomer mixtures and the pure enantiomers are then included.
Particularly preferably:
$R_1$ is selected from the group consisting of:
  1-6C-alkyl,
  1-4C-alkoxy-1-4C-alkyl,
  hydroxy-1-4C-alkyl;
$R_2$ is selected from the group consisting of:
  H,
  1-6C-alkyl; and
$R_3$ and $R_4$ are the same or different and are respectively selected from the group consisting of:
  H,
  1-6C-alkyl,
  1-4C-alkoxy-1-4C-alkyl,
  1-3C-alkoxy-carbonyl-1-6C-alkyl,
  hydroxy-1-4C-alkyl;
or $R_3$ and $R_4$ together form a butylene ($-CH_2-CH_2-CH_2-CH_2-$)—, pentylene ($-CH_2-CH_2-CH_2-CH_2-CH_2-$), hydroxypentylene, azapentylene or oxapentylene group.
Particularly preferably:
$R_1$ is selected from the group consisting of:
  1-6-C-alkyl;
$R_2$ is selected from the group consisting of:
  H,
  1-6C-alkyl;
and
$R_3$ and $R_4$ are the same or different and are respectively selected from the group consisting of:
  H,
  1-6C-alkyl,
  1-4C-alkoxy-1-4C-alkyl,
  1-3C-alkoxy-carbonyl-1-6C-alkyl,
  hydroxy-1-4C-alkyl;
or $R_3$ and $R_4$ together form a pentylene ($-CH_2-CH_2-CH_2-CH_2-CH_2-$), hydroxypentylen, preferably 3-hydroxypentylene or oxapentylene group, as described above.

Particularly preferred complex compounds of the general formula (II) are described in the examples.

The invention further relates to a method for the preparation of the iron(III) complex compounds according to the invention which comprises the reaction of a β-ketoamide with an iron(III) salt.

β-ketoamide include, in particular, those of the formula (III):

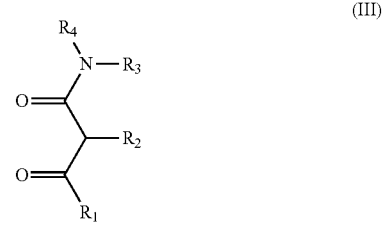

wherein $R_1$ to $R_4$ are defined as above.

Examples of suitable iron(III) salts include: iron(III) chloride, iron(III) acetate, iron(III) sulfate, iron(III) nitrate and iron(III) acetylacetonate, among which iron(III) chloride is preferred.

Another preferred method is shown in the following scheme:

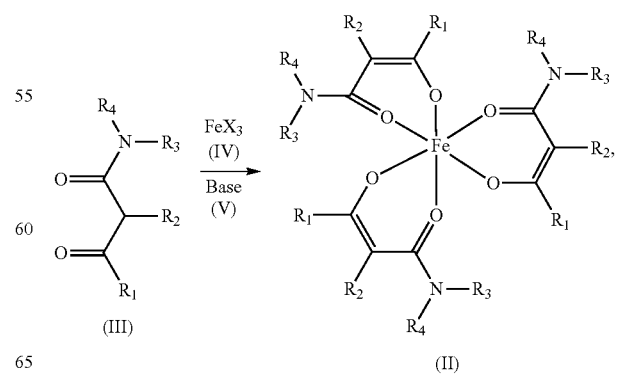

wherein $R_1$ to $R_4$ are defined as above, X is an anion such as halogenide, such as chloride, a carboxylate, such as acetate, sulfate, nitrate and acetylacetonate and base is a common organic or inorganic base.

In the method according to the invention, preferably 3-5 eq ligand (III), using suitable iron(III) salts (IV) (in this case Fe(III) chloride, Fe(III) acetate, Fe(III) sulfate and Fe(III) acetylacetonate are particularly suitable), are reacted under standard conditions to form the corresponding complexes of the general formula (II). In this case, the synthesis is carried out under the pH conditions optimal for complex formation. The optimum pH value is set by adding a base (V); in this case, the use of sodium carbonate, sodium hydrogencarbonate, sodium methanolate, potassium carbonate, potassium hydrogencarbonate or potassium methanolate is particularly suitable.

The ligands (III) required for the preparation of the complexes are either commercially available or were prepared according to the following synthesis method. For this purpose, two different synthesis processes were used. For ligands of the general formula $R_1$=methyl, $R_2$=H the commercially available diketone (3) was reacted under standard conditions with the corresponding amine (4) to form the ligand of the general formula (III).

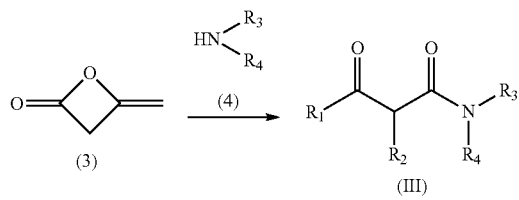

For the other ligands of the general formula (III), the appropriate ketoester (5) was reacted under standard conditions with the corresponding amine (6).

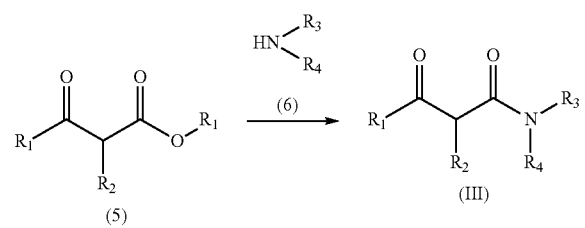

wherein $R_1$ to $R_4$ are respectively defined as above.

Pharmaceutically acceptable salts of the compounds according to the invention in which the iron(III) complex formally carries a positive charge include, for example, salts with suitable anions, such as carboxylates, sulfonates, sulfates, chlorides, bromides, iodides, phosphates, tartates, methanesulfonates, hydroxethanesulfonates, glycinates, maleates, propionates, fumarates, tulouenesulfonates, benzene sulfonates, trifluoroacetates, naphthalenedisulfonates-1,5, salicylates, benzoates, lactates, salts of malic acid, salts of 3-hydroxy-2-naphthoic acid-2, citrates and acetates.

Pharmaceutically acceptable salts of the compounds according to the invention in which the iron(III) complex formally carries a negative charge include, for example, salts with suitable pharmaceutically acceptable bases, such as, for example, salts with alkaline or alkaline-earth hydroxides, such as NaOH, KOH, Ca(OH)$_2$, Mg(OH)$_2$ etc., amine compounds such as ethylamine, diethylamine, triethylamine, ethyldiisopropylamine, ethanolamine, diethanolamine, triethanolamine, methylglucamine, dicyclohexylamine, dimethylaminoethanol, procaine, dibenzylamine, N-methylmorpholine, arginine, lysine, ethylenediamine, N-methylpiperidin, 2-amino-2-methyl-propanol-(1), 2-amino-2-methyl-propandiol-(1,3), 2-amino-2-hydroxyl-methyl-propandiol-(1,3) (TRIS) etc.

The water-solubility or the solubility in physiological saline solution and thus, optionally, also the efficacy of the compounds according to the invention can be significantly influenced by salt formation in general, specifically by the choice of the counterion.

Preferably, the compounds according to the invention constitute neutral complex compounds.

Advantageous Pharmacological Effects:

Surprisingly, the inventors found that the iron(III) β-ketoamide complex compounds which are the subject matter of the present invention and which are represented, in particular, by the general structural formula (II), are stable bioavailable iron complexes and suitable for use as a medicament for the treatment and prophylaxis of iron deficiency symptoms and iron deficiency anemias the symptoms accompanying them.

The medicaments containing the compounds according to the invention are suitable for use in human and veterinary medicine.

The compounds according to the invention are thus also suitable for preparing a medicament for the treatment of patients suffering from symptoms of an iron deficiency anemia, such as, for example: fatigue, listlessness, lack of concentration, low cognitive efficiency, difficulties in finding the right words, forgetfulness, unnatural pallor, irritability, acceleration of heart rate (tachycardia), sore or swollen tongue, enlarged spleen, desire for strange foods (pica), headaches, lack of appetite, increased susceptibility to infections or depressive moods.

The iron(III) complex compounds according to the invention are furthermore suitable for the treatment of iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), iron deficiency anemia caused by menstruation, iron deficiency anemia caused by injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemias, restless leg syndrome caused by iron deficiency anemias, iron deficiency anemias in the case of cancer, iron deficiency anemias caused by chemotherapies, iron deficiency anemias triggered by inflammation (AI), iron deficiency anemias in the case of congestive cardiac insufficiency (CHF; congestive heart failure), iron deficiency anemias in the case of chronic renal insufficiency stage 3-5 (CDK 3-5; chronic kidney diseases stage 3-5), iron deficiency anemias triggered by chronic inflammation (ACD), iron deficiency anemias in the case of rheumatoid arthritis (RA), iron deficiency anemias in the case of systemic lupus erythematosus (SLE) and iron deficiency anemias in the case of inflammatory bowel diseases (IBD).

Administration can take place over a period of several months until the iron status is improved, which is reflected, for example, by the hemoglobin level, transferrin saturation and the serum ferritin level of the patients, or until the desired improvement of the state of health affected by iron deficiency anemia.

The preparation according to the invention can be taken by children, adolescents and adults.

The applied compounds according to the invention can in this case be administered both orally as well as parentally. Oral administration is preferred.

The compounds according to the invention and the aforementioned combinations of the compounds according to the invention with other active substances or medicines can thus be used, in particular, for the preparation of medicaments for the treatment of iron deficiency anemia, such as iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), menstruation, injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemia, restless leg syndrome.

The application according to the invention leads to an improvement of the iron, hemoglobin, ferritin and transferrin levels, which, in particular in children and adolescents, but also in adults, is accompanied by an improvement in short-term memory tests (STM), long-term memory tests (LTM), Ravens' progressive matrices test, in the Wechsler adult intelligence scale (WAIS) and/or in the emotional coefficient (Baron EQ-i, YV test, youth version), or to an improvement of the neutrophile level, the antibody levels and/or lymphocyte function.

Furthermore, the present invention relates to pharmaceutical compositions comprising one or more of the compounds according to the invention, in particular according to the formula (II), as well as optionally one or more further pharmaceutically effective compounds, as well as optionally one or more pharmacologically acceptable carriers and/or auxiliary substances and/or solvents.

These are common pharmaceutical carriers, auxiliary substances or solvents. The above-mentioned pharmaceutical compositions are suitable, for example, for intravenous, intraperitoneal, intramuscular, intravaginal, intrabuccal, percutaneous, subcutaneous, mucocutaneous, oral, rectal, transdermal, topical, intradermal, intragasteral or intracutaneous application and are provided, for example, in the form of pills, tablets, enteric-coated tablets, film tablets, layer tablets, sustained release formulations for oral, subcutaneous or cutaneous administration (in particular as a plaster), depot formulations, dragees, suppositories, gels, salves, syrup, granulates, suppositories, emulsions, dispersions, microcapsules, microformulations, nanoformulations, liposomal formulations, capsules, enteric-coated capsules, powders, inhalation powders, microcrystalline formulations, inhalation sprays, epipastics, drops, nose drops, nose sprays, aerosols, ampoules, solutions, juices, suspensions, infusion solutions or injection solutions etc.

Preferably, the compounds according to the invention as well as pharmaceutical compositions containing such compounds are applied orally, although other forms, such as parentally, in particular intravenously, are also possible.

For this purpose, the compounds according to the invention are preferably provided in pharmaceutical compositions in the form of pills, tablets, enteric-coated tablets, film tablets, layer tablets, sustained release formulations for oral administration, depot formulations, dragees, granulates, emulsions, dispersions, microcapsules, microformulations, nanoformulations, liposomal formulations, capsules, enteric-coated capsules, powders, microcrystalline formulations, epipastics, drops, ampoules, solutions, suspensions, infusion solutions or injection solutions.

The compounds according to the invention can be administered in pharmaceutical compositions which may contain various organic or inorganic carrier and/or auxiliary materials as they are customarily used for pharmaceutical purposes, in particular for solid medicament formulations, such as, for example, excipients (such as saccharose, starch, mannitol, sorbitol, lactose, glucose, cellulose, talcum, calcium phosphate, calcium carbonate), binding agents (such as cellulose, methylcellulose, hydroxypropylcellulose, polypropyl pyrrolidone, gelatine, gum arabic, polyethylene glycol, saccharose, starch), disintegrating agents (such as starch, hydrolyzed starch, carboxymethylcellulose, calcium salt of carboxymethylcellulose, hydroxypropyl starch, sodium glycol starch, sodium bicarbonate, calcium phosphate, calcium citrate), lubricants (such as magnesium stearate, talcum, sodium laurylsulfate), a flavorant (such as citric acid, menthol, glycin, orange powder), preserving agents (such as sodium benzoate, sodium bisulfite, methylparaben, proylparaben), stabilizers (such as citric acid, sodium citrate, acetic acid and multicarboxylic acids from the titriplex series, such as, for example, diethylenetriaminepentaacetic acid (DTPA), suspending agents (such as methycellulose, polyvinyl pyrrolidone, aluminum stearate), dispersing agents, diluting agents (such as water, organic solvents), beeswax, cocoa butter, polyethylene glycol, white petrolatum, etc.

Liquid medicament formulations, such as solvents, suspensions and gels usually contain a liquid carrier, such as water and/or pharmaceutically acceptable organic solvents. Furthermore, such liquid formulations can also contain pH-adjusting agents, emulsifiers or dispersing agents, buffering agents, preserving agents, wetting agents, gelatinizing agents (for example methylcellulose), dyes and/or flavoring agents. The compositions may be isotonic, that is, they can have the same osmotic pressure as blood. The isotonicity of the composition can be adjusted by using sodium chloride and other pharmaceutically acceptable agents, such as, for example, dextrose, maltose, boric acid, sodium tartrate, propylene glycol and other inorganic or organic soluble substances. The viscosity of the liquid compositions can be adjusted by means of a pharmaceutically acceptable thickening agent, such as methylcellulose. Other suitable thickening agents include, for example, xanthan gum, carboxymethylcellulose, hydroxypropylcellulose, carbomer and the like. The preferred concentration of the thickening agent will depend on the agent selected. Pharmaceutically acceptable preserving agents can be used in order to increase the storage life of the liquid composition. Benzyl alcohol can be suitable, even though a plurality of preserving agents including, for example, paraben, thimerosal, chlorobutanol and benzalkonium chloride can also be used.

The active substance can be administered, for example, with a unit dose of 0.001 mg/kg to 500 mg/kg body weight, for example 1 to 4 times a day. However, the dose can be increased or reduced depending on the age, weight, condition of the patient, severity of the disease or type of administration.

EXAMPLES

The invention is illustrated in more detail by the following examples. The examples merely constitute exemplifications, and the person skilled in the art is capable of extending the specific examples to other compounds claimed. The designation of the names of the examples were defined and determined using the computer program ACD/Name Version 12.

Starting Compounds:

The starting compounds used in the examples were obtained as follows.

A. N,N-diethyl-3-oxobutaneamide

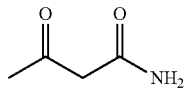

Commercially available: Fluka 00405

B. N,N-diethyl-3-oxobutaneamide

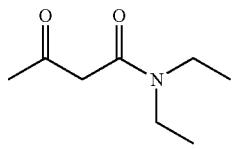

Commercially available: Aldrich 165093

C. N,N-dimethyl-3-oxobutaneamide

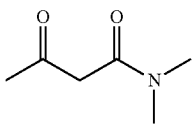

Commercially available: Aldrich 407054

D. N-methyl-3-oxobutaneamide

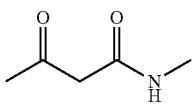

Commercially available: Acros 25544

E. 2-chloro-N-methyl-3-oxobutaneamide

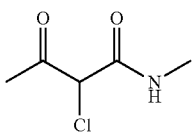

Commercially available: Aurora Fine Chemicals Ltd. Kafd-00164

F. 1-(piperidin-1-yl)-butane-1,3-dione

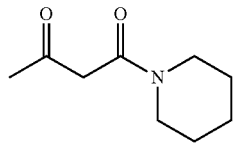

A solution of 25 g (0.294 mol) piperidin in 100 ml tert.-butyl-methylether was added dropwise to a solution of 26.25 g (0.310 mol) diketene in 200 ml tert.-butyl-methylether at −5 to 0° C. After stirring for 1 hour at −1° C., no starting material was detected anymore by thin-layer chromatography. The reaction mixture was spun off and the residue was distilled under vacuum. 49.55 g of product was obtained as a slightly yellow liquid.

IR (in substance, cm$^{-1}$): 3001, 2936, 2856, 1719, 1631, 1584, 1486, 1441, 1389, 1355, 1302, 1255, 1219, 1159, 1137.
Elemental analysis: C, 63.51; H, 8.94; N, 8.36.
LC-MS: 170 (M+H), 192 (M+Na)
$^1$H-NMR (CDCl$_3$, 400 MHz): δ [ppm]=35 (4H), 3.3 (2H), 2.2 (3H), 1.6 (2H), 1.5 (4H).

G. N,N-bis-(2-hydroxyethyl)-3-oxobutaneamide

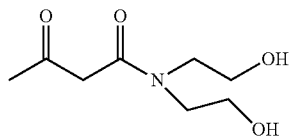

A solution of 52.53 g (0.50 mol) diethanolamine in 100 ml MeOH was added dropwise to a solution of 40.00 g (0.48) diketene in 100 ml MeOH at 0° C. After stirring for 1 hour at 0° C., no starting material was detected anymore by thin-layer chromatography. The reaction mixture was spun off and the residue was purified by means of column chromatography. 81.32 g of product was obtained as a slightly yellow oil.

IR (in substance, cm$^{-1}$): 3381, 2941, 2885, 1718, 1626, 1481, 1432, 1361, 1312, 1212, 1053.
Elemental analysis: C, 50.62; H, 8.05; N, 7.28.
$^1$H-NMR (CDCl$_3$, 400 MHz): δ [ppm]=2.2 (3H), 3.5 (4H), 3.7 (6H), 4.15 (1H), 4.35 (1H).

H. N-butyl-N-methyl-3-oxobutaneamide

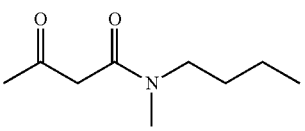

14.1 ml (0.12 mol) N-n-butylmethylamine was added dropwise to a solution of 10.00 g (0.12 mol) diketene in 500 ml MeOH at 0° C. After stirring for 6 hours at 0° C., no starting material was detected anymore by thin-layer chromatography. The reaction mixture was spun off and the residue was purified by means of column chromatography. 11.61 g of product was obtained as a slightly yellow oil.

IR (in Substance, cm$^{-1}$): 2958, 2932, 2873, 1721, 1635, 1593, 1493, 1381, 1358, 1307, 1228, 1209, 1144.

LC-MS: 172 (M+H).

$^1$H-NMR (CDCl$_3$, 400 MHz): δ [ppm]=0.9 (3H), 1.3 (2H), 1.5 (2H), 1.9 (1H), 2.2 (2H), 2.9 (3H), 3.2 (1H), 3.3 (1H), 3.5 (1H).

I. 1-(4-hydroxypiperidin-1-yl)-butane-1,3-dione

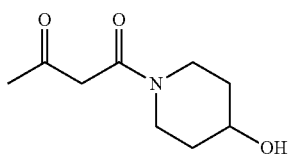

A solution of 25.30 g (0.25 mol) 4-hydroxy-piperidin in 50 ml MeOH was added dropwise to a solution of 20.00 g (0.24) diketene in 50 ml MeOH at 0° C. After stirring for 1 hour at 0° C., no starting material was detected anymore by thin-layer chromatography. The reaction mixture was spun off and the residue was purified by means of column chromatography. 42.54 g (96% yield) of a slightly yellow oil was obtained.

IR (in substance, cm$^{-1}$): 3401, 2928, 2869, 1717, 1617, 1448, 1360, 1307, 1268, 1206, 1158, 1074, 1026.

CHN elemental analysis: C, 57.98; H, 8.69; N, 7.32.

LC-MS: 186 (M+H).

$^1$H-NMR (CDCl$_3$, 400 MHz): δ [ppm]=1.5 (2H), 1.8 (2H), 2.2 (3H), 3.2 (2H), 3.6 (3H), 3.9 (2H).

J. 3-oxo-N,N-dipropylbutaneamide

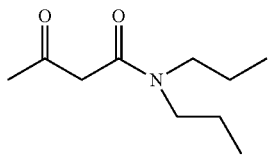

A solution of 27.80 g (0.28 mol) N,N-di-n-propylamine was added dropwise to a solution of 20.00 g (0.24) diketene in 100 ml MeOH at 0° C. After stirring for 3 hours at 0° C., no starting material was detected anymore by thin-layer chromatography. The reaction mixture was spun off and the residue was purified by means of column chromatography. 38.05 g of product was obtained as a slightly yellow oil.

IR (in substance, cm$^{-1}$): 2964, 2934, 2876, 1721, 1634, 1589, 1490, 1456, 1430, 1392, 1381, 1359, 1301, 12444, 1101.

Elemental analysis: C, 64.28; H, 10.17; N, 7.36.

$^1$H-NMR (CDCl$_3$, 400 MHz): δ [ppm]=0.9 (6H), 1.6 (4H), 1.9 (1H), 2.3 (2H), 3.1 (2H), 3.3 (2H), 3.5 (2H).

K. N-hexyl-3-oxobutaneamide

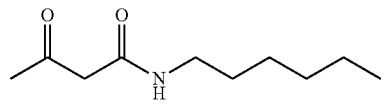

A solution of 27.83 g (0.28 mol) N-n-hexylamine was added dropwise to a solution of 20.00 g (0.24) diketene in 100 ml MeOH at 0° C. After stirring for 4 hours at 0° C., no starting material was detected anymore by thin-layer chromatography. The reaction mixture was spun off, and the obtained solid was taken up in 200 ml n-hexane, filtrated off and dried overnight under vacuum. 22.53 g of product was obtained as a white solid.

IR (in substance, cm$^{-1}$): 3272, 3098, 2956, 2921, 2872, 2853, 1728, 1709, 1644, 1563, 1467, 1419, 1363, 1347, 1336, 1190, 1167.

Elemental analysis: C, 64.85; H, 10.28; N, 7.62.

$^1$H-NMR (CDCl$_3$, 400 MHz): δ [ppm]=0.9 (3H), 1.3 (6H), 1.5 (2H), 2.2 (3H), 3.2 (2H), 3.4 (2H), 6.9 (1H).

L. Ethyl-N-(3-oxobutanoyl)glycinate (3-oxo-butyrylamino)ethyl acetate)

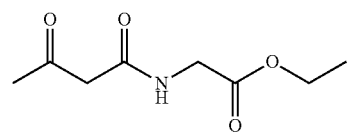

A solution of 20.00 g (0.24 mol) diketene in 250 ml toluene was added dropwise at 0° C. to a solution of 33.21 g (0.24 mol) glycine ethyl ester hydrochloride (amino acetic ester hydrochloride). 40.00 g (0.48 mol) NaHCO$_3$ were then added and the reaction mixture was stirred further at room temperature overnight. Since no starting material could be detected anymore by thin-layer chromatography, the reaction mixture was spun off, and the obtained solid was taken up in 100 ml diethylether, stirred for a short period of time, filtrated off and dried overnight under vacuum. 40.00 g of product was obtained as a white solid.

IR (in substance, cm$^{-1}$): 3346, 1750, 1708, 1669, 1538, 1399, 1360, 1320, 1278, 1198, 1165, 1024.

Elemental analysis: C, 51.57; H, 7.05; N, 7.55.

LC-MS: 210 (M+Na), 188 (M+H).

$^1$H-NMR (CDCl$_3$, 400 MHz): δ [ppm]=1.2 (3H), 2.2 (3H), 3.4 (2H), 4.0 (2H), 4.2 (2H), 7.4 (1H).

M. 3-oxoheptaneamide

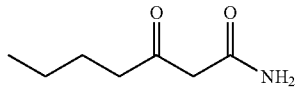

0.4 mol (63.7 ml) 3-oxo-heptanoic acid methylester and 400 ml 7 N ammonia solution was stirred for three hours at 100° C. in a pressure reactor. After cooling off, the solvents were distilled off on a rotavap, the raw products were taken up in 200 ml water and 40 ml ethanol and set to about pH 3 with 40 ml 32% HCl. The reaction mixture was heated to 90° C. for 4 hours and then again concentrated to dryness in the rotavap, taken up in 600 ml dichloromethane and washed 3 times with 100 ml water. The organic phase was distilled off and the raw product recrystallized from 100 ml toluene. The product was filtrated off and dried in a vacuum drying cabinet at 50° C. 3.5 g of the title compound was obtained.

IR (in substance, cm$^{-1}$): 3368, 3178, 2956, 2932, 2872, 1703, 1651, 1619, 1466, 1439, 1408, 1376, 1345, 1306, 1221, 1183, 1125, 1058, 716, 663.

Elemental analysis: C, 58.38; H, 9.12; N, 9.90.

LC-MS: 144 (M+H).

$^1$H-NMR (DMSO-d$_6$, 400 MHz): δ [ppm]=14.5 (s, 1H), 7.45 (s, 1H), 7.01 (s, 1H), 4.92 (s, 1H), 2.06 (t, 2H), 1.47-1.38 (m, 3H), 1.31-1.18 (m, 2H), 0.88-0.81 (m, 3H); keto tautomer (86%), δ=7.45 (s, 1H), 7.01 (s, 1H), 3.23 (s, 2H), 2.49 (t, 2H), 1.47-1.38 (m, 2H), 1.31-1.18 (m, 2H), 0.88-0.81 (m, 3H).

N. N-methyl-3-oxoheptaneamide

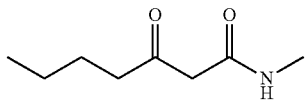

0.378 mol (60.2 ml) 3-oxo-heptanoic acid methylester, 400 ml 33% methylamine solution in ethanol and 40 ml water were stirred for 48 hours at 80° C. in a round-bottomed flask with a reflux condenser. After cooling off, the solvents were distilled off on a rotavap, the raw products were taken up in 200 ml water and 40 ml ethanol and set to about pH 3 with 40 ml 32% HCl. The reaction mixture was heated to 90° C. for 24 hours and then again concentrated to dryness in the rotavap. The raw product heated with 150 ml to reflux, filtrated hot and the filtrate was left to cool off. The product was filtrated off and dried in a vacuum drying cabinet at 50° C. 5.9 g of the title compound was obtained.

IR (in substance, cm$^{-1}$): 3368, 3178, 2956, 2932, 2872, 1703, 1651, 1619, 1466, 1439, 1408, 1376, 1345, 1306, 1221, 1183, 1125, 1058, 716, 663.

Elemental analysis: C, 60.22; H, 9.69; N, 8.75.

$^1$H-NMR (DMSO-d$_6$, 400 MHz): δ [ppm]=keto tautomer (ca. 90%), enol tautomer*(ca. 10%), =8.21*/7.81*(m, 1H), 7.94 (s, 1H), 6.12*/4.91*(s, 1H), 3.25 (s, 2H), 2.69*/2.61*(d, 3H), 2.57 (d, 3H), 2.50-2.46 (m, 2H), 2.06*(t, 2H), 1.45-1.38 (m, 2H), 1.31-1.18 (m, 2H), 0.88-0.81 (m, 3H)

(*enol tautomer probably present as E-Z isomer of the amide bond)

O. N,N-dimethyl-3-oxoheptaneamide

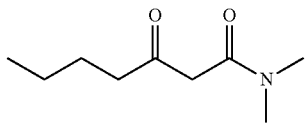

0.632 mol (100 ml) methyl-3-oxoheptanoate (3-oxo-heptanoic acid methylester) and 227 ml 33% dimethylamine solution in ethanol (approx. 1.26 mol dimethylamine) was stirred for 4 hours at 110° C. in a pressure reactor. After cooling off, the solvents were distilled off on a rotavap, the raw product was taken up in 40 ml water, 30 ml 32% HCl and 40 ml ethanol and stirred for 24 hours at 100° C. The mixture was again concentrated to dryness by evaporation, taken up again in 300 ml acetic ester and filtrated, the solvents were then distilled off on the rotavap. 26 g of raw product was purified over 500 g silica gel 60 (mobile solvent: acetic ester: hexane 1:1, flow 50 ml/min, fraction size: 100 ml, product: fractions 20-35), the product was obtained as a mobile oil. 17.8 g of the title compound was obtained.

IR (in substance, cm$^{-1}$): 2957, 2932, 2873, 1717, 1639, 1597, 1501, 1465, 1396, 1366, 1302, 1262, 1197, 1142, 1058, 933, 776, 726, 692, 645, 612.

Elemental analysis: C, 62.12; H, 9.965; N, 8.17.

$^1$H-NMR (DMSO-d$_5$, 400 MHz): δ [ppm]=enol tautomer (28%), δ=15.1 (s, 1H), 5.32 (s, 1H), 3.3-2.4 (m, 6H), 2.13 (t, 2H), 1.51-1.39 (m, 2H), 1.34-1.18 (m, 2H), 0.89-0.82 (m, 3H); keto tautomer (72%), δ=3.57 (s, 2H), 2.88 (s, 3H), 2.80 (s, 3H), 2.50-2.48 (m, 2H), 1.51-1.39 (m, 2H), 1.34-1.18 (m, 2H), 0.89-0.82 (m, 3H).

P. 3-oxopentaneamide

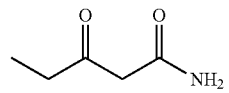

0.8 mol (100 ml) methyl-3-oxovalerate (3-oxo-pentanoic acid methylester) and 220 ml 7 N ammonia solution in methanol was stirred for 4 hours at 110° C. in a pressure reactor. After cooling off, the solvents were distilled off on a rotavap, the raw product was taken up in 100 ml ethanol and filtrated. The filtrate was concentrated, the residue was dissolved in 40 ml dimethylether and left to stand at +5° C. for 2 days. The product, which had crystallized in fine needles, was filtrated off and dried in a vacuum drying cabinet at 50° C. 7.10 g of the title compound was obtained.

IR (in substance, cm$^{-1}$): 3370, 3177, 2974, 2937, 2878, 1705, 1651, 1620, 1440, 1384, 1355, 1301, 1268, 1189, 1109, 1043, 999, 911, 863, 804, 740, 659.

Elemental analysis: C, 51.48; H, 7.924; N, 12.28.

$^1$H-NMR (DMSO-d$_6$, 400 MHz): δ [ppm]=enol tautomer (12%), δ=14.5 (s, 1H), 7.45 (s, 1H), 7.01 (s, 1H), 4.93 (s, 1H), 2.09 (q, 2H), 1.00 (t, 3H); keto tautomer (88%), δ=7.45 (s, 1H), 7.01 (s, 1H), 3.24 (s, 2H), 2.5 (q superposed, 2H), 0.90 (t, 3H).

Q. N,N-dimethyl-3-oxopentaneamide

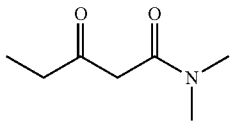

0.8 mol (100 ml) methyl-3-oxovalerate (3-oxo-pentanoic acid methylester) and 250 ml 33% dimethylamine solution in ethanol (approx. 1.4 mol dimethylamine) was stirred for 4 hours at 110° C. in a pressure reactor. After cooling off, the solvents were distilled off on a rotavap, the raw products were taken up in 40 ml water, 30 ml 32% HCl and 40 ml ethanol and stirred for 24 hours at 100° C. The mixture was again concentrated to dryness by evaporation, taken up again in 300 ml acetic ester and filtrated. The filtrate was concentrated to dryness by evaporation and the product was completely dried under an oil-pump vacuum. 25.8 g of the title compound was obtained.

IR (in substance, cm$^{-1}$): 2976, 2939, 1717, 1637, 1500, 1459, 1396, 1376, 1357, 1298, 1262, 1198, 1142, 1107, 1055, 967, 912, 775, 647, 611.

Elemental analysis: C, 54.78; H, 8.724; N, 9.20.

$^1$H-NMR (DMSO-d$_6$, 400 MHz): δ [ppm]=enol tautomer (12%), δ=15.1 (s, 1H), 5.31 (s, 1H), 2.89 (s, 3H), 2.81 (s, 3H), 2.15 (q, 2H), 1.04 (t, 3H); keto tautomer (87%), δ=3.57 (s, 2H), 2.89 (s, 3H), 2.81 (s, 3H), 2.49 (q, 2H), 0.91 (t, 3H).

R. 3-oxo-2-(piperidin-1-ylcarbonyl)butanenitrile

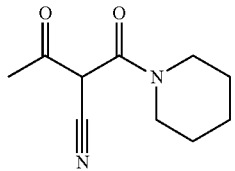

In a nitrogen atmosphere, 45.6 (0.30 mol) 1-cyanoacetylpiperidin was provided in 800 ml THF (dry). 18.7 g (0.47 mol) NaH (60% mineral oil suspension) was added such that the inner temperature did not exceed 10° C. (cooling with an ice/NaCl bath). This was followed by stirring for 30 min at 0-10° C. 20 ml (0.28 mol) acetylchloride were dosed in in such a way that the inner temperature did not exceed 10° C. The reaction mixture was subsequently stirred for 1 hour at 45° C. Then, 40 ml acetic acid were added slowly, the reaction mixture was put on 2.0 l ice water and 50 ml HCl (20% m/m) were dosed in. The mixture was shaken out with 500 ml toluene, the organic phase was separated, dried over 120 g Na$_2$SO$_4$ and filtrated. The solution was concentrated at 40° C./80 mbar on the rotavap to form an oil and was cooled with a mixture of ice and common salt. The precipitated solid was filtrated off, washed with 50 ml cold toluene, and dried for at least 15 hours at 50° C./<100 mbar. 35.1 g of product was obtained as a solid.

IR (in substance, cm$^{-1}$): 3009, 2943, 2863, 2206, 2147, 1763, 1659, 1573, 1483, 1455, 1275, 1229, 1131, 1022, 969.

Elemental analysis: C, 60.22; H, 9.69; N, 8.75.

$^1$H-NMR (CDCl$_3$, 400 MHz): δ [ppm]=1.56-1.67 (m, 6H), 2.27 (s, 3H), 3.66 (t, 4H), 17.17 (br. s, 1H).

S. N-butyl-3-oxobutaneamide

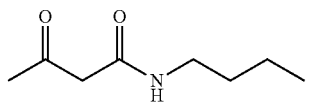

14.64 g (0.2 mol) n-butylamine and 200 mg DMAP were provided in 60 ml THP (dry) and 16.8 g (0.2 mol) diketene was dosed in at −5 to 5° C. The reaction mixture was then stirred for 2 hours at 20-25° C. and then concentrated on the rotavap. The residue was dried for at least 15 hours at 50° C./<100 mbar. 16.0 g of product was obtained.

IR (in substance, cm$^{-1}$): 3271, 3097, 2959, 2928, 2867, 1714, 1644, 1561, 1459, 1421, 1357, 1227, 1163, 1000, 968, 759, 724, 656, 619.

$^1$H-NMR (CDCl$_3$, 400 MHz): δ [ppm]=0.86-0.94 (m, 3H), 1.26-1.71 (m, 4H), 2.23 (s, 3H), 3.23 (q, 2H), 3.36 (s, 2H), 7.00 (br. s, 1H).

T. N,N-dibutyl-3-oxobutaneamide

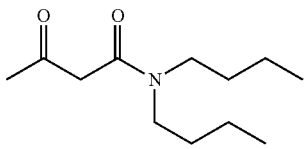

16.8 g (0.20 mol) diketene was provided in 60 ml THF under nitrogen and the solution was cooled to approximately −10° C. by means of an ice/NaCl mixture. 25.6 g (0.20 mol) di-n-butylamine were then dosed in in such a way that the inner temperature did not exceed 0° C. The reaction mixture was subsequently stirred for 1 hour at −10 to 0° C., and then for 2 hours at 20-25° C. The solvent of the reaction mixture was distilled off on the rotavap at 50° C./<100 mbar. 45.9 g of product was obtained as an oil.

10 g each of this raw product was put on 200 g silica gel and eluted with 2 l acetic ester/n-hexane (2:1 v/v). The eluate was concentrated to form an oil on the rotavap at 50° C. 7<100 mbar and dried further for at least 15 hours under high vacuum at 20-25° C. 31.5 g of product was obtained as an oil.

IR (in substance, cm$^{-1}$): 2958, 2932, 2873, 1722, 1635, 1590, 1490, 1458, 1431, 1392, 1372, 1292, 1226, 1144, 1113, 1037, 1007, 931, 774, 732, 683.

$^1$H-NMR (CDCl$_3$, 400 MHz): δ [ppm]/keto tautomer β=0.87-0.92 (m, 3H), 1.25-1.31 (m, 2H), 1.47-1.50 (m, 2H), 2.23 (s, 3H), 3.26-3.30 (m, 2H), 3.45 (s, 2H); enol tautomer β=0.87-0.92 (m, 3H), 1.25-1.31 (m, 2H), 1.47-1.50 (m, 2H), 1.91 (m, 3H), 3.13-3.17 (m, 2H), 5.00 (s, 1H), 14.95 (br. s, 1H).

U. Not Awarded

V. N,N-dibutyl-3-oxopentanamide

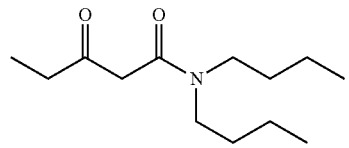 [SMILES: CCCCN(CCCC)C(=O)CC(=O)CC]

0.16 mol (20 ml) of methyl 3-oxovalerate (3-oxo-pentanoic acid methyl ester) and 0.415 mol (70 ml) of dibutylamine were stirred for 3 h at 130° C., where methanol formed was removed via a distillation bridge. Thereafter, excess dibutylamine was distilled on a rotary evaporator, the crude product taken up in 40 ml water and 90 ml of ethanol, with 3 ml 20% HCl adjusted to pH 3 and stirred for 1 h at 50° C. The mixture was again evaporated to dryness, dissolved again in 200 ml ethyl acetate and washed 3 times with 100 ml of water. The organic phase was dried over Na$_2$SO$_4$ and after filtration evaporated in a rotary evaporator to dryness. After drying, 31.8 g of the title compound were obtained.

IR (neat, cm$^{-1}$): 2959, 2933, 2874, 1721, 1631, 1589, 1490, 1458, 1429, 1393, 1374, 1320, 1292, 1250, 1223, 1188, 1144, 1111, 1061, 940, 914, 800, 775, 732, 689, 635.

CHN-Elemental analysis: C, 68.22; H, 11.336; N, 6.51.

LC-MS: M+H$^+$228.5; M+Na$^+$250.5.

1H-NMR (DMSO-d$_6$, 400 MHz): Enol-Tautomer (40%), δ=15.1 (s, 1H), 5.31 (s, 1H), 2.89 (s, 3H), 2.81 (s, 3H), 2.15 (q, 2H), 1.04 (t, 3H); Keto-Tautomer (60%), δ=3.57 (s, 2H), 2.89 (s, 3H), 2.81 (s, 3H), 2.49 (q, 2H), 0.91 (t, 3H).

W. 2-Fluoro-N,N-dimethyl-3-oxobutanamide

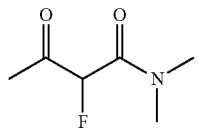

0.2 mol (25 ml) of ethyl 2-fluoroacetoacetat and 107 ml 33% dimethylamine in ethanol (0.6 mol dimethylamine) were stirred for 3 h at 70° C. The reaction mixture was evaporated to dryness and 27 g of crude product chromatographed over 350 g silica gel with ethyl acetate/methanol 9/1. 13.4 g of the title compound were obtained.

IR (neat, cm$^{-1}$): 2942, 1729, 1650, 1501, 1403, 1358, 1260, 1217, 1176, 1151, 1072, 962, 829, 705, 681, 632, 611.

CHN-Elemental analysis: C, 47.99; H, 6.70; N, 9.05.

LC-MS: M+H$^+$148.2; M+Na$^+$170.2.

1H-NMR (DMSO-d$_6$, 400 MHz): δ=5.96 (d (J=48 Hz), 1H), 3.03 (d (J=1.4 Hz), 3H), 2.86 (d (J=1.3 Hz), 3H), 2.18 (d (J=4.0 Hz), 3H).

X. 2-Fluoro-3-oxo-N-propylbutanamide

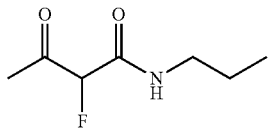

0.8 mol (65.8 ml) of n-propylamine were added dropwise within 0.5 h to 0.2 mol (25 ml) of ethyl 2-fluoroacetoacetat. The reaction mixture was heated and then held for 2 h at 60° C. Then it was evaporated to dryness, dissolved in 50 ml water and 60 ml ethanol and adjusted with 32% HCl to pH 3. It was again evaporated, dissolved in 300 ml ethyl acetate, filtered and again evaporated to dryness. 17 g of crude product was chromatographed over 800 g silica gel with ethyl acetate/hexane 1/1. After drying, 14 g of the title compound were obtained.

IR (neat, cm$^{-1}$): 3325, 2967, 2938, 2878, 1736, 1665, 1535, 1460, 1441, 1421, 1359, 1277, 1235, 1210, 1179, 1150, 1089, 963, 892, 818, 617.

CHN-Elemental analysis: C, 50.61; H, 7.19; N, 8.58.

LC-MS: M+H$^+$, 162.7; M+Na$^+$184.6.

1H-NMR (DMSO-d$_6$, 400 MHz): δ=8.47 (s (broad), 1H), 5.49 (d (J=49 Hz), 1H), 3.05 (m, 2H), 2.22 (d (J=3.1 Hz), 3H), 2.18 (d (J=4.0 Hz), 3H); 1.42 (sextet, 2H); 0.81 (t, 3H).

Y 4-Methoxy-N,N-dimethyl-3-oxobutaneamide

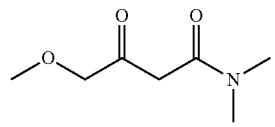

0.17 mol (25 g) of methyl 4-methoxy-acetoacetate and 91 ml 33% dimethylamine in ethanol (about 0.51 mol dimethylamine) were stirred in a pressure reactor for 4 h at 110° C. The reaction mixture was then evaporated to dryness and 27 g of crude product chromatographed over 350 g silica gel with ethyl acetate/methanol 9/1. After drying, 12.4 g of the title compound were obtained.

LC-MS: M+H$^+$, 160.7; M+Na$^+$, 182.6.

1H-NMR (DMSO-d$_6$, 400 MHz): Enol-Tautomer (21%), δ=15.1 (s, 1H), 5.48 (s, 1H), 3.90 (s, 2H), 3.30 (s, 3H), 3.0-2.8 (m, 6H); Keto-Tautomer (79%), δ=4.10 (s, 2H), 3.55 (s, 2H), 3.27 (s, 3H), 2.90 (s, 3H), 2.81 (s, 3H).

Z. N,N,4-Trimethyl-3-oxopentanamide

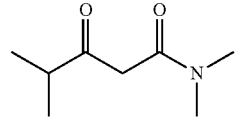

0.69 mol (100 g) of 4-methyl-3-oxovaleric acid methyl ester and 309 ml 33% dimethylamine in ethanol (about 1.73 mol dimethylamine) were stirred in a pressure reactor for 2 hours at 110° C. After cooling, the solvents were distilled on a rotary evaporator. After drying, 93 g of the title compound were obtained.

IR (neat, cm$^{-1}$): 2969, 2934, 2875, 1714, 1630, 1597, 1502, 1467, 1396, 1384, 1359, 1322, 1263, 1207, 1162, 1142, 1073, 1047, 972, 927, 892, 782, 725, 701, 650, 614.

CHN-Elemental analysis: C, 59.51; H, 9.60; N, 8.47.

LC-MS: M+H$^+$, 158.5; M+Na$^+$, 180.2.

1H-NMR (DMSO-d$_6$, 400 MHz): Enol-Tautomer (19%), δ=15.18 (s, 1H), 5.28 (s, 1H), 2.87 (s, 3H), 2.80 (s, 3H), 2.35 (heptet, 1H), 1.05 (d, 6H); Keto-Tautomer (81%), δ=3.62 (s, 2H), 2.87 (s, 3H), 2.80 (s, 3H), 2.68 (heptet, 1H), 1.00 (d, 6H).

AA. 4-Methyl-1-(morpholin-4-yl)-pentane-1,3-dione

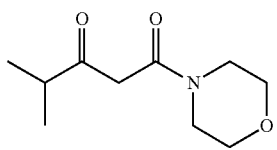

0.351 mol (49.6 ml) of 4-methyl-3-oxovaleric acid methyl ester and 0.369 mol (32.3 ml) morpholine were stirred for 14 hours at 110° C. in a Dean-Stark apparatus. 8 ml methanol were collected. Subsequently, the excess starting materials was distilled off for 3 h on a rotary evaporator (80° C. water bath, 2 mbar). The crude product was dissolved in 500 ml toluene and extracted with 50 ml of 1 M NaOH and 3 times with 50 ml water, and the organic phase was concentrated on a rotary evaporator to dryness. After drying, 62.2 g of the title compound were obtained.

IR (neat, cm$^{-1}$): 2969, 2929, 2858, 1713, 1636, 1587, 1460, 1436, 1385, 1361, 1301, 1272, 1243, 1190, 1166, 1113, 1069, 1050, 1036, 984, 964, 929, 886, 850, 779, 733, 700, 660, 619.

CHN-Elemental analysis: C, 58.04; H, 8.24; N, 6.95.

LC-MS: M+H$^+$, 200 9; M+Na$^+$, 222.8.

1H-NMR (DMSO-d$_6$, 400 MHz): Enol-Tautomer (16%), δ=14.7 (s, 1H), 5.37 (s, 1H), 3.57-3.28 (m, 8H), 2.36 (heptet, 1H), 1.06 (d, 6H); Keto-Tautomer (84%), δ=3.70 (s, 2H), 3.57-3.28 (m, 8H), 2.67 (heptet, 1H), 1.00 (d, 6H).

AB. 4-Methoxy-1-(morpholin-4-yl)butane-1,3-dione

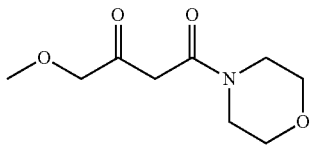

0.346 mol (50.5 g) of methyl 4-methoxy-acetoacetate and 0.363 mol (31.6 g) of morpholine was stirred for 20 h at 110° C. in a Dean-Stark apparatus. There were further added 0.069 mol (6.02 g) of morpholine and stirred further 3 hours. Subsequently, the excess starting materials were distilled off on a rotary evaporator. 67.3 g of crude product was chromatographed over 600 g silica gel with ethyl acetate/ethanol 9/1. There were 36.9 g of the title compound.

IR (neat, cm$^{-1}$): 2921, 2857, 2361, 1729, 1633, 1590, 1438, 1362, 1303, 1272, 1244, 1199, 1111, 1069, 1038, 1019, 984, 965, 939, 920, 849, 778, 718, 681, 631.

LC-MS: M+H$^+$, 202.7; M+Na$^+$, 224.6.

1H-NMR (DMSO-d$_6$, 400 MHz): δEnol-Tautomer (14%), δ=14.8 (s, 1H), 5.55 (s, 1H), 3.91 (s, 2H), 3.60-3.32 (m, 8H), 3.30 (s, 3H); Keto-Tautomer (86%), δ=4.11 (s, 2H), 3.60 (s, 2H), 3.60-3.32 (m, 8H), 3.28 (s, 3H).

AC. 3-Acetyl-1-methylpyrrolidin-2-one

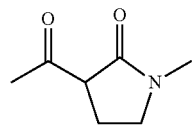

20.40 g (0.20 mol) of diisopropylamine were placed in 200 ml dry THF under nitrogen and 80 ml n-butyl lithium in hexane (2.5 M) were added dropwise. It was allowed to stir for 20 minutes and then 20.00 g (0.20 mol) of 1-methyl-2-pyrrolidinone were added dropwise at −78° C. After stirring the reaction mixture for 1 hour 17.64 g (0.20 mol) of dry ethyl acetate were added at −78° C. The reaction mixture was warmed to room temperature and stirred for 14 hours. The THF was removed on a rotary evaporator under reduced pressure and the residue was taken up in 80 ml of 6 N HCl. The acidic aqueous phase was saturated with NaCl and extracted 5 times with 300 ml ethyl acetate. The combined organic layers were dried over Na$_2$SO$_4$, and the solvent was removed on a rotary evaporator. The remaining yellow oil was purified by column chromatography. This gave 5.10 g product as a light yellow oil.

IR (neat, cm$^{-1}$): 3495, 2929, 2885m 1714, 1674, 1500, 1433, 1403, 1358, 1297, 1262, 1166, 1107, 989, 763, 712.

$^1$H-NMR (CDCl$_3$, 400 MHz): δ [ppm]=1.95 (1H), 2.30 (3H), 2.45 (1H), 2.75 (3H), 3.25 (1H), 3.35 (1H), 3.5 (1H).

AD. Ethyl (1-methyl-2-oxopyrrolidin-3-yl)(oxo)acetate

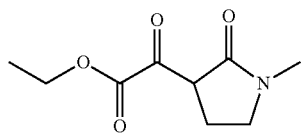

13.20 g of 60% NaH (in paraffin oil) (0.33 mol) was added to 100 ml of dry diethyl ether. With vigorous stirring, 19.83 g (0.20 mol) of N-methylpyrrolidone were added. Then within one hour 121.30 g (0.83 mol) of diethyl oxalate were added dropwise. After the addition the suspension was heated to 40° C. and stirred for 21 hours. The reaction mixture was then cooled in an ice bath, mixed with 66 ml 5M HCl and the resulting 2-phase mixture was filtered once. Then the two phases were separated, and the aqueous phase was extracted twice with 100 ml diethyl ether. The combined ethereal phases were dried over Na$_2$SO$_4$ and concentrated on a rotary evaporator to dryness. The oily residue was cooled to −80° C. and mixed with 200 ml diethyl ether. The resulting brown solid was filtered off and recrystallized from heptane. This gave 5.2 g product as white needles.

IR (neat, cm$^{-1}$): 3342, 2977, 2939, 1723, 1658, 1581, 1498, 1469, 1448, 1373, 1344, 1307, 1269, 1196, 1160, 1117, 1094, 1024, 977, 903, 876, 819, 783, 737, 701, 675.

$^1$H-NMR (CDCl$_3$, 400 MHz): δ [ppm]=1.26 (3H), 2.83 (3H), 2.94 (2H), 3.37 (2H), 4.21 (2H), 11.80 (1H).

AE. Ethyl (1-methyl-2-oxopiperidin-3-yl)(oxo)acetate

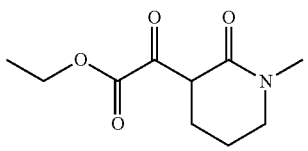

20.4 g of diisopropylamine (0.1 mol) were dissolved in 200 ml of dry THF under nitrogen and cooled in a freezing mixture. 80 ml n-butyllithium in hexane (2.5 M, 0.2 mol) were added dropwise slowly. After the addition it was allowed to stir for 60 minutes and then 22.6 g N-methyl-2-piperidone (0.2 mol) were added dropwise. The reaction mixture was stirred for another 20 min in the freezing mixture. In a second flask, 87.7 g diethyl oxalate (0.6 mol) in 100 ml of dry THF were cooled in a freezing mixture and the cooled reaction mixture was cannulated with stirring in small portions to it. It was left overnight under stirring to warm to room temperature. The THF was removed on a rotary evaporator and the residue was taken up in 80 ml half concentrated hydrochloric acid. The aqueous phase was extracted five times with 300 ml ethyl acetate, the combined organic phases were dried over sodium sulfate and concentrated on a rotary evaporator to dryness. The excess diethyl oxalate was removed by distillation (2-3 mbar, 80° C.) and 45 g of crude product were obtained. 10.4 g product was obtained as white crystals with a melting point of 23° C. after crystallization from diethyl ether/n-hexane.

IR (neat, cm$^{-1}$): 2981, 2935, 1721, 1610, 1503, 1449, 1393, 1371, 1331, 1304, 1247, 1223, 1193, 1095, 1081, 1028, 995, 944, 895, 860, 794, 758, 722, 671, 628.

$^1$H-NMR (CDCl$_3$, 400 MHz): δ [ppm]=14.00 (1H), 4.20 (2H), 3.25 (2H), 2.90 (3H), 2.65 (2H), 1.73 (2H), 1.23 (3H).

AF. 3-Acetyl-1-methyl-piperidin-2-one

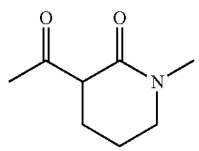

20.6 g of diisopropylamine (0.2 mol) were placed in 200 ml of dry THF under nitrogen and cooled to −80° C. 80 ml n-butyllithium in hexane (2.5 M, 0.2 mol) were slowly added dropwise. After the addition it was allowed to stir for 15 min and then 22.6 g N-methyl-2-piperidone (0.2 mol) were added dropwise. The reaction mixture was stirred for 30 min and then 17.6 g of dry ethyl acetate (0.2 mol) was added. The reaction mixture with stirring overnight was allowed to warm to room temperature. The THF was removed on a rotary evaporator and the residue was taken up in 80 ml 6M HCl. The aqueous phase was extracted five times with 100 ml ethyl acetate. The combined organic layers were dried over sodium sulfate and the solvent was removed on a rotary evaporator. The product (keto form:enol form=1:1) was fractionated by distillation at 0.6 mbar and obtained as a yellowish liquid (bp 70° C.).

IR (neat, cm$^{-1}$): 3506, 2940, 2865, 1715, 1632, 1597, 1498, 1463, 1443, 1401, 1386, 1354, 1330, 1310, 1252, 1203, 1160, 1118, 1081, 983, 952, 887, 762, 686, 651, 606.

Enol form:
$^1$H-NMR (CDCl$_3$, 400 MHz): δ [ppm]=1.81 (2H), 1.92 (3H), 2.38 (2H), 2.96 (3H), 3.30 (2H), 14.8 (1H).

Keto form:
$^1$H-NMR (CDCl$_3$, 400 MHz): δ [ppm]=1.81 (3H), 2.14 (1H), 2.34 (3H), 2.99 (3H), 3.30 (2H), 3.48 (1H).

AG. Ethyl 4-(dimethylamino)-2,4-dioxobutanoate

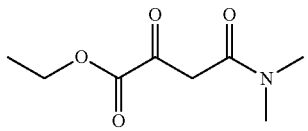

10.2 g of diisopropylamine (0.1 mol) were dissolved in 100 ml of dry THF under nitrogen and cooled in a freezing mixture. 40 ml n-butyllithium in hexane (2.5 M, 0.1 mol) were slowly added dropwise. When the addition was completed it was allowed to stir for 60 minutes and then 8.7 g N,N-dimethylacetamide (0.1 mol) were added dropwise. The reaction mixture was stirred for another 20 min in the freezing mixture. In a second flask, 43.7 g of diethyl oxalate (0.3 mol) in 50 ml of dry THF were cooled in a freezing mixture and the cooled reaction mixture was cannulated with stirring in small portions to it. It was left overnight under stirring to warm to room temperature. The THF was removed on a rotary evaporator and the residue was taken up in 80 ml half concentrated hydrochloric acid. The aqueous phase was extracted five times with 150 ml ethyl acetate, the combined organic phases dried over sodium sulfate and concentrated on a rotary evaporator to dryness. The excess diethyl oxalate was removed by distillation (2-3 mbar, 80° C.) and 17 g of crude product were obtained. 5.5 g product was obtained as white crystals with a melting point of 28° C. after crystallization from n-hexane.

IR (neat, cm$^{-1}$): 2984, 2941, 1738, 1620, 1507, 1467, 1393, 1370, 1355, 1313, 1260, 1170, 1126, 1016, 927, 860, 823, 772, 723, 628.

$^1$H-NMR (CDCl$_3$, 400 MHz): δ [ppm]=1.38 (3H), 3.06 (6H), 4.33 (2H), 6.25 (1H)

AH. 1-(Morpholin-4-yl)butane-1,3-dione

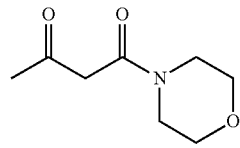

33 ml (0.38 mol) of morpholine were added dropwise at −5 to 0° C. to a solution of 30 g of diketene (0.36 mol) in 300 ml tetrahydrofuran. After 1 h stirring at 0° C. no more starting material was detected by thin layer chromatography. The reaction mixture was evaporated and the residue purified by column chromatography. This gave 49.48 g (0.29 mol, 81% yield) of a white solid.

IR (neat, cm$^{-1}$): 2965, 2918, 2858, 1718, 1633, 1587, 1488, 1436, 1359, 1303, 1273, 1245, 1220, 1112.

CHN-Elemental analysis: C, 56.03; H, 7.62; N, 8.12.

LC-MS: 172 (M+H), 194 (M+Na).

$^1$H-NMR (CDCl$_3$, 400 MHz): δ [ppm]=3.6 bis 3.3 (10H), 2.2 (3H).

AI. N-(2-Methoxyethyl)-3-oxobutanamide

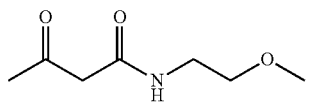

33 ml (0.38 mol) methoxyethylamine were added dropwise to a solution of 30 g of diketene (0.36 mol) in 300 ml tetrahydrofuran at −5 to 0° C. After 1 h stirring at 0° C. no more starting material was detected by thin layer chromatography. The reaction mixture was evaporated and the residue purified by column chromatography. This gave 47.15 g (0.30 mol, 83% yield) of a white solid.

IR (neat, cm$^{-1}$): 3291, 3095, 2978, 2922, 2887, 2851, 1709, 1643, 1560, 1417, 1356, 1344, 1297, 1195, 1166, 1122, 1092.

¹H-NMR (CDCl₃, 400 MHz): δ [ppm]=7.1 (1H), 3.4 bis 3.3 (9H), 2.2 (3H).

AJ. N-Cyclopropyl-3-oxobutanamide

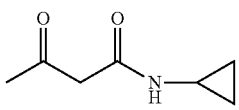

26 ml (0.38 mmol) cyclopropylamine was added dropwise to a solution of 30 g of diketene (0.36 mol) in 300 ml tetrahydrofuran at −5 to 0° C. After 1 h stirring at 0° C. no more starting material was detected by thin layer chromatography. The reaction mixture was evaporated and the residue purified by column chromatography. This gave 43.83 g (0.31 mol, 87% yield) of a white solid.

IR (neat, cm⁻¹): 3266, 3082, 3017, 2953, 2922, 1724, 1666, 1636, 1450, 1421, 1358, 1338, 1221, 1193, 1161, 1014.
LC-MS: 140 (M−H).
¹H-NMR (CDCl₃, 400 MHz): δ [ppm]=7.2 (1H), 3.4 (2H), 2.7 (1H), 2.2 (3H), 0.7 (2H), 0.5 (2H).

AK. 3-Oxo-N-(propan-2-yl)butanamide

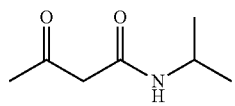

32 ml (0.38 mmol) of isopropylamine were added dropwise to a solution of 30 g of diketene (0.36 mol) in 300 ml tetrahydrofuran at −5 to 0° C. After 1 h stirring at 0° C. no more starting material was detected by thin layer chromatography. The reaction mixture was evaporated and the residue purified by column chromatography. This gave 40.36 g (0.28 mol, 79% yield) of a white solid.

IR (neat, cm⁻¹): 3254, 3088, 2975, 2925, 1725, 1633, 1561, 1459, 1422, 1350, 1334, 1314, 1289, 1190, 1160, 1133.
¹H-NMR (CDCl₃, 400 MHz): δ [ppm]=6.9 (1H), 4.0 (1H), 3.3 (2H), 2.2 (3H), 1.1 (6H).

AL. N-(2-Hydroxyethyl)-3-oxobutanamide

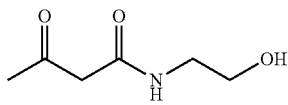

23 ml (0.38 mmol) of ethanolamine were added dropwise to a solution of 30 g of diketene (0.36 mol) in 300 ml tetrahydrofuran at −5 to 0° C. After 1 h stirring at 0° C. no more starting material was detected by thin layer chromatography. The reaction mixture was evaporated and the residue purified by column chromatography. This gave 41.44 g (0.29 mol, 80% yield) as a white solid.

IR (neat, cm⁻¹): 3273, 3097, 2973, 2938, 2880, 1710, 1646, 1558, 1494, 1465, 1420, 1362, 1347, 1312, 1297, 1215, 1190, 1166, 1052, 1038.

CHN-Elemental analysis: C, 49.13; H, 7.76; N, 9.71.
LC-MS: 145 (M), 127 (M−H2O).
¹H-NMR (CDCl₃, 400 MHz): δ [ppm]=7.5 (1H), 3.7 (2H), 3.4 (4H), 2.2 (3H).

AM. N-(3-hydroxypropyl)-3-oxobutanamide

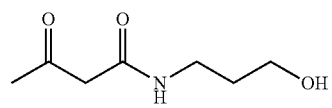

28 ml (0.38 mmol) of 3-amino-1-propanol were added dropwise to a solution of 30 g of diketene (0.36 mol) in 300 ml tetrahydrofuran at −5 to 0° C. After 1 h stirring at 0° C. no more starting material was detected by thin layer chromatography. The reaction mixture was evaporated and the residue purified by column chromatography. This gave 47.15 g (0.30 mol, 83% yield) of a white solid.

IR (neat, cm⁻¹): 3295, 3090, 2940, 2877, 1715, 1643, 1545, 1470, 1416, 1358, 1324, 1213, 1160, 1056, 963.
LC-MS: 182 (M+Na), 160 (M+H), 142 (M−OH).
¹H-NMR (CDCl₃, 400 MHz): δ [ppm]=7.4 (1H), 3.6 (3H), 3.3 (4H), 2.2 (3H), 1.6 (2H).

AN. N-(4-Hydroxybutyl)-3-oxobutanamide

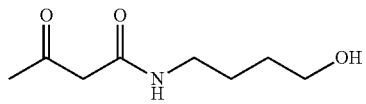

A solution of 22 ml (0.24 mol) of 4-amino-1-butanol in 50 ml tetrahydrofuran was added dropwise to a solution of 20 g of diketene (0.24 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 35.43 g (0.21 mol, 86% yield) of a white solid.

IR (neat, cm⁻¹): 3273, 3098, 2933, 2866, 1712, 1644, 1555, 1418, 1361, 1344, 1322, 1188, 1167, 1060.
¹H-NMR (CDCl₃, 400 MHz): δ [ppm]=7.4 (1H), 3.6 (2H), 3.3 (2H), 3.2 (2H), 3.1 (1H), 2.22 (3H), 1.5 (4H).

AO-1. N-(5-Hydroxypentyl)-3-oxobutanamide

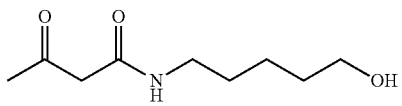

A solution of 39 g (0.38 mol) of 5-amino-1-pentanol in 300 ml tetrahydrofuran was added dropwise to a solution of 30 g of diketene (0.36 mol) in 300 ml tetrahydrofuran at −5 to 0° C. After 1 h stirring at 0° C. no more starting material was detected by thin layer chromatography. The reaction mixture was evaporated and the residue purified by column chromatography. This gave 52.70 g (0.28 mol, 79% yield) as a white solid.

IR (neat, cm$^{-1}$): 3269, 3096, 2928, 2855, 1725, 1711, 1643, 1418, 1361, 1340, 1190, 1166, 1060, 1007.

LCMS: 188 (M+H).

$^1$H-NMR (CDCl$_3$, 400 MHz): δ [ppm]=7.2 (1H), 3.6 (2H), 3.4 (2H), 3.2 (2H), 2.8 (1H), 2.2 (3H), 1.5 (4H), 1.3 (2H).

AO-2. N-(1-Hydroxy-2-methylpropan-2-yl)-3-oxobutanamide

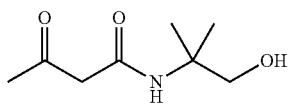

A solution of 33.40 g (0.38 mol) 2-amino-2-methyl-1-propanol in 300 ml of tetrahydrofuran was added dropwise to a solution of 30 g of diketene (0.36 mol) in 300 ml of tetrahydrofuran at −5 to 0° C. After 1 h stirring at 0° C. no more starting material was detected by thin layer chromatography. The reaction mixture was evaporated and the residue purified by column chromatography. This gave 50.00 g (0.29 mol, 81% yield) of a white solid.

IR (neat, cm$^{-1}$): 3308, 2973, 2932, 1714, 1646, 1545, 1456, 1412, 1359, 1331, 1267, 1160, 1057.

CHN-Elemental analysis: C, 54.99; H, 8.67; N, 8.42.

LCMS: 172 (M−H).

$^1$H-NMR (CDCl$_3$, 400 MHz): δ [ppm]=7.1 (1H), 4.6 (1H), 3.5 (2H), 3.3 (2H), 2.2 (3H), 1.3 (3H).

AP. N-(2-Hydroxyethyl)-N-methyl-3-oxobutanamide

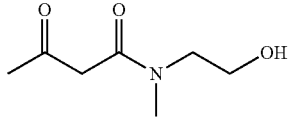

A solution of 30 ml (0.38 mol) 2-(methylamino)ethanol in 300 ml tetrahydrofuran was added dropwise to a solution of 30 g of diketene (0.36 mol) in 300 ml tetrahydrofuran at −5 to 0° C. After 1 h stirring at 0° C. no more starting material was detected by thin layer chromatography. The reaction mixture was evaporated and the residue purified by column chromatography. This gave 41.46 g (0.26 mol, 73% yield) of a white solid.

IR (neat, cm$^{-1}$): 3407, 2934, 1717, 1620, 1491, 1401, 1357, 1308, 1161, 1121, 1050, 928, 861, 778.

LCMS: 159 (M), 141 (M−H2O).

$^1$H-NMR (CDCl$_3$, 400 MHz): δ [ppm]=3.7 (3H), 3.5 (2H), 3.3 (1H), 3.0 (2H), 2.9 (1H), 2.2 (3H).

AQ. N-(2-Hydroxypropyl)-3-oxobutanamide

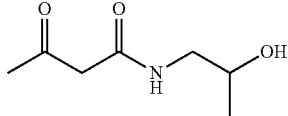

19 ml (0.24 mol) 1-amino-2-propanol were added dropwise to a solution of 20 g of diketene (0.24 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 29.50 g (0.19 mol, 78% yield) of a colorless oil.

IR (neat, cm$^{-1}$): 3307, 3088, 2972, 2930, 1714, 1643, 1545, 1415, 1359, 1326, 1161, 1134, 1090.

$^1$H-NMR (CDCl$_3$, 400 MHz): δ [ppm]=7.4 (1H), 3.9 (1H), 3.8 (1H), 3.3 (2H), 3.1 (2H), 2.2 (3H), 1.1 (3H).

AR. N-(1-Hydroxypropan-2-yl)-3-oxobutanamide

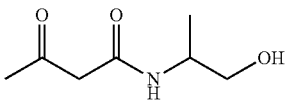

19 ml (0.24 mol) of 2-amino-1-propanol were added dropwise to a solution of 20 g of diketene (0.24 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 27.12 g (0.17 mol, 71% yield) of a colorless oil.

IR (neat, cm$^{-1}$): 3295, 3083, 2974, 2935, 2877, 1714, 1640, 1544, 1454, 1413, 1358, 1324, 1220, 1160, 1095, 1050, 992.

$^1$H-NMR (CDCl$_3$, 400 MHz): δ [ppm]=7.2 (1H), 4.0 (1H), 3.9 (1H), 3.6 (1H), 3.4 (2H), 2.2 (3H), 1.1 (3H).

AS. N-(1-Hydroxybutan-2-yl)-3-oxobutanamide

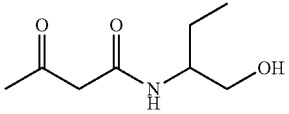

34 ml (0.36 mol) of 2-amino-1-butanol were added dropwise to a solution of 30 g of diketene (0.36 mol) in 300 ml tetrahydrofuran at −5 to 0° C. After 1 h stirring at 0° C. no more starting material was detected by thin layer chromatography. The reaction mixture was evaporated and the residue purified by column chromatography. This gave 46.97 g (0.27 mol, 76% yield) of a colorless oil.

IR (neat, cm$^{-1}$): 3294, 3085, 2986, 2936, 2878, 1714, 1640, 1544, 1461, 1414, 1358, 1218, 1160, 1089, 1052.

$^1$H-NMR (CDCl$_3$, 400 MHz): δ [ppm]=7.2 (1H), 3.8 (1H), 3.6 (1H), 3.5 (1H), 3.4 (1H), 3.3 (1H), 2.2 (3H), 1.5 (1H), 1.4 (1H), 0.8 (3H).

AT. N-(2,3-Dihydroxypropyl)-3-oxobutanamide

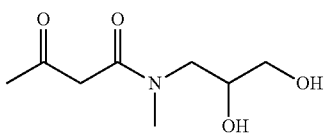

A solution of 22.5 g (0.21 mol) 3-methylamino-1,2-propanediol in 200 ml of tetrahydrofuran was added dropwise to a solution of 18 g of diketene (0.21 mol) in 200 ml of tetrahydrofuran at −5 to 0° C. After 1 h stirring at 0° C. no more starting material was detected by thin layer chromatography. The reaction mixture was evaporated and the residue purified by column chromatography. This gave 32.00 g (0.17 mol, 79% yield) of a colorless oil.

IR (neat, cm$^{-1}$): 3385, 2931, 1716, 1616, 1492, 1403, 1358, 1310, 1162, 1103, 1040, 925.

LC-MS: 212 (M+Na), 190 (M+H), 172 (M−OH).

$^1$H-NMR (CDCl$_3$, 400 MHz): δ [ppm]=3.9 (1H), 4.8 bis 3.3 (8H), 3.1 (3H), 2.3 (3H).

AU. 1-(3-Hydroxypiperidin-1-yl)butane-1,3-dione

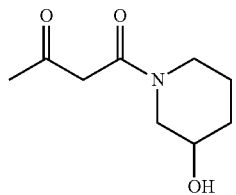

A solution of 36.10 g (0.36 mol) of 3-hydroxypiperidine in 300 ml tetrahydrofuran was added dropwise to a solution of 30 g of diketene (0.36 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 53.53 g (0.29 mol, 81% yield) of a white solid.

IR (neat, cm$^{-1}$): 3340, 1716, 1618, 1596, 1485, 1462, 1437, 1410, 1360, 1343, 1319, 1279, 1263, 1185, 1159, 1138, 1001, 921, 858.

$^1$H-NMR (CDCl$_3$, 400 MHz): δ [ppm]=3.8 (2H), 3.6 bis 3.2 (5H), 2.9 (1H), 2.2 (3H), 1.8 (2H), 1.6 (1H), 1.4 (1H).

AV. 1-[4-(Hydroxymethyl)piperidin-1-yl]butane-1,3-dione

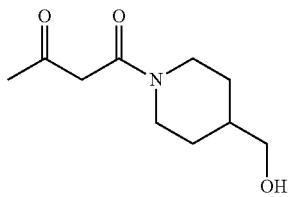

A solution of 25 g (0.22 mol) of 4-piperidine methanol in 200 ml tetrahydrofuran was added dropwise to a solution of 18 g of diketene (0.2 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 35.40 g (0.18 mol, 83% yield) of a colorless oil.

IR (neat, cm$^{-1}$): 3401, 3003, 2918, 2860, 1718, 1618, 1447, 1358, 1313, 1270, 1200, 1158, 1089, 1036, 987, 956.

$^1$H-NMR (CDCl$_3$, 400 MHz): δ [ppm]=4.5 (1H), 3.7 (1H), 3.4 (2H), 3.3 (2H), 2.9 (1H), 2.6 (1H), 2.5 (1H), 2.2 (3H), 1.7 (3H), 1.1 (2H).

AW. 1-[3-(Hydroxymethyl)piperidin-1-yl]butane-1, 3-dione

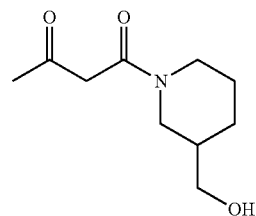

A solution of 25 g (0.22 mol) of 3-piperidinemethanol in 200 ml tetrahydrofuran was added dropwise to a solution of 18 g of diketene (0.2 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 31.50 g (0.16 mol, 74% yield) of a colorless oil.

IR (neat, cm$^{-1}$): 3411, 2926, 2859, 1717, 1618, 1442, 1358, 1308, 1262, 1222, 1183, 1160, 1036, 855.

$^1$H-NMR (CDCl$_3$, 400 MHz): δ [ppm]=4.1 (1H), 3.6 bis 3.2 (7H), 2.9 (1H), 2.2 (3H), 1.7 (3H), 1.3 (2H).

AX. 1-[2-(Hydroxymethyl)piperidin-1-yl]butane-1, 3-dione

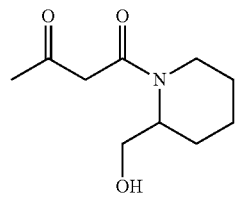

A solution of 25 g (0.22 mol) 2-piperidinemethanol in 200 ml tetrahydrofuran was added dropwise to a solution of 18 g of diketene (0.2 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 32.40 g (0.17 mol, 76% yield) of a colorless oil.

IR (neat, cm$^{-1}$): 3403, 2936, 1717, 1612, 1442, 1357, 1309, 1267, 1226, 1158, 1139, 1049.

¹H-NMR (CDCl₃, 400 MHz): δ [ppm]=4.7 (1H), 4.4 (1H), 3.9 bis 3.7 (2H), 3.6 bis 3.3 (3H), 2.2 (3H), 1.7 bis 1.3 (6H).

AY. 1-[(3S)-3-Hydroxypyrrolidin-1-yl]butane-1,3-dione

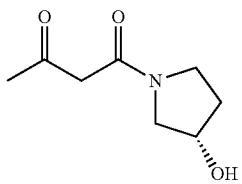

A solution of 21.8 g (0.25 mol) (S)-3-pyrrolidinol in 200 ml tetrahydrofuran was added dropwise to a solution of 20 g of diketene (0.24 mol) in 200 ml of tetrahydrofuran at −5 to 0° C. added. After 1 h stirring at 0° C. no more starting material was detected by thin layer chromatography. The reaction mixture was evaporated and the residue purified by column chromatography. This gave 31.35 g (0.18 mol, 77% yield) of a colorless oil.

IR (neat, cm⁻¹): 3390, 2948, 1717, 1616, 1438, 1383, 1357, 1224, 1188, 1160, 1102, 988, 871.

¹H-NMR (CDCl₃, 400 MHz): δ [ppm]=4.4 (1H), 4.1 (1H), 3.6 bis 3.3 (5H), 2.2 (3H), 2.0 bis 1.8 (3H).

AZ. 1-[4-(2-Hydroxyethyl)piperazin-1-yl]butane-1,3-dione

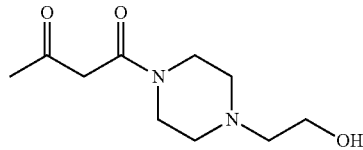

A solution of 32.5 g (0.25 mol) 1-(2-hydroxyethyl)piperazine in 100 ml tetrahydrofuran was added dropwise to a solution of 20 g of diketene (0.24 mol) in 200 ml of tetrahydrofuran at −5 to 0° C. After 1 h stirring at 0° C. no more starting material was detected by thin layer chromatography. The reaction mixture was evaporated and the residue purified by column chromatography. This gave 36.10 g (0.17 mol, 71% yield) of a colorless oil.

IR (neat, cm⁻¹): 3412, 2922, 2812, 1717, 1628, 1441, 1357, 1305, 1156, 1051, 1001, 875.

LC-MS: 237 (M+Na), 215 (M+H).

¹H-NMR (CDCl₃, 400 MHz): δ [ppm]=3.6 (4H), 3.5 (2H), 3.4 (2H), 2.7 (1H), 2.6 (2H), 2.5 (4H), 2.2 (3H).

AAA. 1-(4-Methylpiperazin-1-yl)butane-1,3-dione

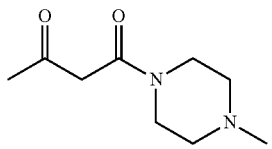

28 ml (0.25 mol) 1-(2-hydroxyethyl)piperazine was added dropwise to a solution of 20 g of diketene (0.24 mol) in 300 ml tetrahydrofuran at −5 to 0° C. After 1 h stirring at 0° C. no more starting material was detected by thin layer chromatography. The reaction mixture was evaporated and the residue purified by column chromatography. This gave 33.70 g (0.18 mol, 77% yield) of a colorless oil.

IR (neat, cm⁻¹): 2938, 2847, 2792, 1719, 1633, 1586, 1488, 1440, 1338, 1358, 1291, 1257, 1141, 1050, 1001, 778.

LC-MS: 207 (M+Na), 185 (M+H).

¹H-NMR (CDCl₃, 400 MHz): δ [ppm]=3.6 (2H), 3.5 (2H), 3.4 (2H), 2.4 (4H), 2.3 (3H), 2.2 (3H).

AAB. N-(3-Hydroxypropyl)-N-methyl-3-oxobutanamide

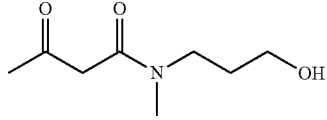

A solution of 20 g (0.23 mol) of 3-methylamino-1-propanol in 50 ml tetrahydrofuran was added dropwise to a solution of 18 g of diketene (0.21 mol) in 200 ml tetrahydrofuran −5 to 0° C. After 1 h stirring at 0° C. no more starting material was detected by thin layer chromatography. The reaction mixture was evaporated and the residue purified by column chromatography. This gave 29.2 g (0.17 mol, 79% yield) of a colorless oil.

IR (neat, cm⁻¹): 3407, 2936, 1718, 1622, 1493, 1402, 1358, 1310, 1161, 1128, 1058, 945.

LC-MS: 156 (M−OH), 174 (M+H), 196 (M+Na).

¹H-NMR (CDCl₃, 400 MHz): δ [ppm]=3.8 bis 3.4 (7H), 2.9 (3H), 2.2 (3H), 1.7 (2H).

AAC. N-(trans-4-Hydroxycyclohexyl)-3-oxobutanamide

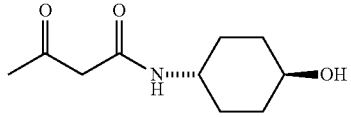

A solution of 28.8 g (0.25 mol) trans-4-aminocyclohexanol in 200 ml tetrahydrofuran was added dropwise to a solution of 20 g of diketene (0.24 mol) in 200 ml tetrahydrofuran at −5 to 0° C. After 1 h stirring at 0° C. no more starting material was detected by thin layer chromatography. The reaction mixture was evaporated and the residue is recrystallized from 200 ml of ethyl acetate. This gave 33.6 g (0.17 mol, 71% yield) of a colorless solid.

IR (neat, cm⁻¹): 3274, 2940, 2859, 1716, 1639, 1543, 1450, 1423, 1338, 1221, 1136, 1098, 1058, 1009, 963, 948, 900.

LC-MS: 200 (M+H), 222 (M+Na).

¹H-NMR (CDCl₃, 400 MHz): δ [ppm]=6.9 (1H), 3.7 (1H), 3.6 (1H), 3.3 (2H), 2.5 (1H), 2.2 (3H), 1.9 (4H), 1.4 bis 1.1 (4H).

AAD.
N-(3-Hydroxy-2,2-dimethylpropyl)-3-oxobutanamide

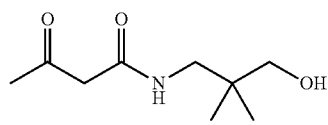

A solution of 32.2 g (0.31 mol) of 3-amino-2,2-dimethyl-propan-1-ol in 60 ml tetrahydrofuran was added dropwise to a solution of 25 g of diketene (0.30 mol) in 200 ml tetrahydrofuran at −5 to 0° C. After 1 h stirring at 0° C. no more starting material was detected by thin layer chromatography. The reaction mixture was evaporated and the residue is recrystallized from 150 ml of ethyl acetate. This gave 40.6 g (0.21 mol, 73% yield) of a colorless solid.

IR (neat, cm⁻¹): 3253, 3099, 2957, 2873, 1724, 1637, 1581, 1476, 1453, 1428, 1358, 1325, 1162, 1035, 995, 785.

LC-MS: (M+H), (M+Na).

¹H-NMR (CDCl₃, 400 MHz): δ [ppm]=7.5 (1H), 3.8 (1H), 3.4 (2H), 3.1 (4H), 2.3 (3H), 0.8 (6H).

AAE. 1-[4-(Dimethylamino)piperidin-1-yl]butane-1,3-dione

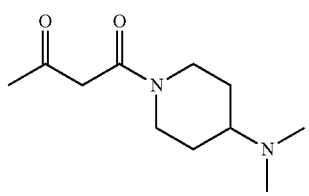

20 g (0.16 mol) of 4-piperidine-dimethylamine were added dropwise to a solution of 12.5 g of diketene (0.15 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 23.9 g (0.11 mol, 76% yield) of a colorless oil.

IR (neat, cm⁻¹): 3270, 2930, 2863, 2721, 1719, 1633, 1585, 1492, 1448, 1389, 1360, 1270, 1238, 1198, 1154, 1060, 1040, 958, 873, 775.

LC-MS: 213 (M+H), 235 (M+Na).

¹H-NMR (CDCl₃, 400 MHz): δ [ppm]=4.5 (1H), 3.7 (1H), 3.5 (2H), 3.0 (1H), 2.6 (1H), 2.3 (1H), 2.2 (9H), 1.8 (2H), 1.3 (2H).

AAF. 1-(4-Methoxypiperidin-1-yl)butane-1,3-dione

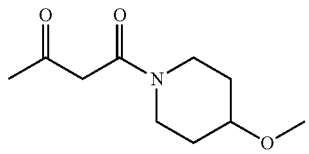

15 g (0.13 mol) of 4-methoxy-piperidine were added dropwise to a solution of 10.4 g of diketene (0.12 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 17.0 g (0.085 mol, 71% yield) of a colorless oil.

IR (neat, cm⁻¹): 2930, 2863, 1720, 1635, 1586, 1488, 1445, 1390, 1359, 1270, 1188, 1097, 1077, 1067, 1024, 939, 904.

LC-MS: 200 (M+H), 223 (M+Na).

¹H-NMR (CDCl₃, 400 MHz): δ [ppm]=3.8 bis 3.2 (8H), 2.2 (3H), 1.8 (4H), 1.5 (2H).

AAG. 1-(2,6-Dimethylmorpholin-4-yl)butane-1,3-dione

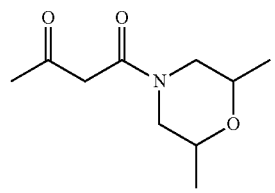

23 ml (0.19 mol) of 2,6-dimethylmorpholine were added dropwise to a solution of 15 g of diketene (0.18 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 26.5 g (0.13 mol, 74% yield) of a colorless oil.

IR (neat, cm⁻¹): 3683, 2974, 2863, 1720, 1635, 1440, 1377, 1359, 1322, 1246, 1223, 1171, 1139, 1083, 1035, 966, 839.

LC-MS: 200 (M+H), 223 (M+Na).

¹H-NMR (CDCl₃, 400 MHz): δ [ppm]=4.4 (1H), 4.0 (1H), 3.6 bis 3.3 (3H), 2.8 (1H), 2.4 (1H), 2.3 (1H), 2.2 (3H), 1.1 (6H).

AAH. N-(Morpholin-4-yl)-3-oxobutanamide

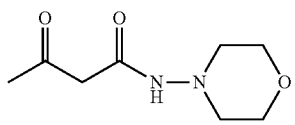

18 ml (0.19 mol) of 4-Aminomorpholine were added dropwise to a solution of 15 g of diketene (0.18 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 26.1 g (0.14 mol, 78% yield) of a colorless oil.

IR (neat, cm$^{-1}$): 3095, 2940, 2841, 1711, 1677, 1625, 1591, 1504, 1448, 1380, 1358, 1302, 1263, 1193, 1163, 1109, 1073, 1038, 912, 869.

LC-MS: 187 (M+H), 210 (M+Na).

$^1$H-NMR (DMSO, 400 MHz): δ [ppm]=3.8 bis 3.3 (6H), 2.8 bis 2.5 (4H), 2.2 (3H), 2.1 (1H).

AAI. 1-(Morpholin-4-yl)pentane-1,3-dione

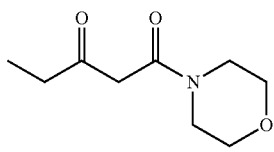

50.0 g (384 mmol) of 3-oxovaleric acid methyl ester and 35.1 g (403 mmol) of morpholine were heated for 9 h at 110° C., whereby the methanol formed was removed via a distillation bridge. The reaction mixture was then freed of volatile constituents on a rotary evaporator and purified by column chromatography (silica gel, eluent: gradient of ethyl acetate to ethanol). The pure product fractions were freed from solvent on a rotary evaporator and yielded 39.7 g (60%) of a viscous, colorless, clear oil.

IR (neat, cm$^{-1}$): 2973, 2858, 1716, 1633, 1437, 1359, 1301, 1272, 1247, 1171, 1111, 1068, 1032, 961, 850, 584.

Elemental analysis: C, 57.26; H, 8.00; N, 7.96.

LC-MS: 186.7 (M+H$^+$), 208.7 (M+Na$^+$).

$^1$H-NMR (CDCl$_3$, 400 MHz): 3.59-3.46 (8H), 3.33 (2H), 2.48 (2H), 0.98 (3H).

AAJ. 1-(4-Hydroxypiperidin-1-yl)pentane-1,3-dione

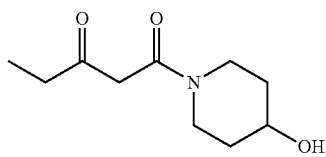

59.0 g (583 mmol) of 4-hydroxypiperidine and 79.7 g (612 mmol) of 3-oxovaleric acid methyl ester were heated for 9 h at 110° C., and the resulting methanol was removed via a distillation bridge. The reaction residue was freed from volatiles on a rotary evaporator, taken up in ethanol, and filtered through 600 ml of strongly acidic ion exchanger (Dowex® HCR-W2), concentrated again and purified by column chromatography (silica gel, eluent's gradient from ethyl acetate to ethanol). The pure product fractions were freed from solvent on a rotary evaporator and yielded 63.6 g (55%) of a viscous, clear, colorless oil.

IR (neat, cm$^{-1}$): 2940, 2877, 1715, 1616, 1449, 1369, 1299, 1171, 1108, 1077, 1059, 1018, 978, 930, 583.

LC-MS: 186.8 (M+H$^+$); 208.7 (M+Na$^+$).

$^1$H-NMR (CDCl$_3$, 400 MHz): 3.85 (2H), 3.60-3.51 (1H), 3.47 (2H), 3.23 (1H), 3.18-3.07 (2H), 2.47 (2H), 1.75 (2H), 1.42 (2H), 0.96 (3H).

AAK. N-Butyl-3-oxoheptanamide

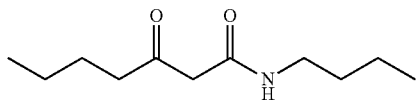

0.9 mol (150 ml) of methyl 3-oxoheptanoate and 2.7 mol (270 ml) butylamine, were stirred 5 h at 100° C. in the pressure vessel. Thereafter, excess butylamine was distilled off on a rotary evaporator, the crude product was taken up in water/ethanol, and adjusted with concentrated HCl to pH 3. The mixture was again evaporated to dryness, taken up again in ethyl acetate and filtered. The filtrate was washed with 1 M HCl and water. The organic phase was dried over Na$_2$SO$_4$ and after filtration evaporated in a rotary evaporator to dryness. The crude product was dissolved in 100 ml diethyl ether and crystallized at 5° C. The product was filtered off and dried. There were obtained 36.0 g of the title compound.

IR (neat, cm$^{-1}$): 3268, 3098, 2958, 2931, 2873, 1723, 1707, 1641, 1563, 1466, 1455, 1434, 1416, 1377, 1350, 1337, 1255, 1227, 1176, 1159, 1125, 1098, 1065, 1013, 969, 904, 881, 774, 734, 716, 650.

CHN-Elemental analysis: C, 66.77; H, 10.62; N, 6.93.

LC-MS: M+H$^+$, 200.6; M+Na$^+$, 222.7.

$^1$H-NMR (DMSO-d$_6$, 400 MHz): Enol-Tautomer (12%), δ [ppm]=14.16 (s, 1H), 7.82 (m, 1H), 4.92 (s, 1H), 3.1-3.0 (m, 2H), 2.06 (t, 2H), 1.5-1.3 (m, 4H), 1.3-1.2 (m, 4H), 0.88-0.82 (m, 6H); Keto-Tautomer (88%), δ=7.97 (m, 1H), 3.24 (s, 2H), 3.02 (q, 2H), 2.47 (t, 2H), 1.5-1.3 (m, 4H), 1.3-1.2 (m, 4H), 0.88-0.81 (m, 6H).

AAL. 1-(4-Hydroxypiperidin-1-yl)-4-methylpentane-1,3-dione

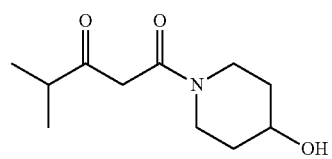

0.351 mol (49.6 ml) of 4-methyl-3-oxovaleric acid methyl ester and 0.369 mol (37.3 g) of 4-hydroxypiperidine were stirred for 6 h at 120° C. in a Dean-Stark apparatus. 12 ml of methanol were collected. Subsequently, the excess starting materials were distilled off for 3 h on a rotary evaporator (80° C. water bath, 2 mbar). 71 g of the title compound were obtained.

IR (neat, cm$^{-1}$): 2934, 2873, 1712, 1619, 1449, 1384, 1364, 1330, 1300, 1267, 1225, 1187, 1166, 1117, 1071, 1025, 979, 955, 930, 846, 808, 777, 733, 693.

CHN-Elemental analysis: C, 50.13; H, 7.514; N, 5.89.

LC-MS: M+H$^+$, 214.9; M+Na$^+$, 239.9.

$^1$H-NMR (DMSO-d$_6$, 400 MHz): Enol-Tautomer (15%), δ [ppm]=5.39 (s, 1H), 4.49 (s (broad), 1H), 3.9-2.9 (m, 5H), 2.6-2.5 (m, 1H), 1.75-1.11 (m, 4H), 1.06 (d, 6H); Keto-Tautomer (85%), δ=4.73 (s (broad), 1H), 3.67 (s, 2H), 3.9-2.9 (m, 5H), 2.68 (heptet, 1H), 1.75-1.11 (m, 4H), 1.00 (d, 6H).

AAM.
N-(2-Hydroxyethyl)-N,4-dimethyl-3-oxopentanamide

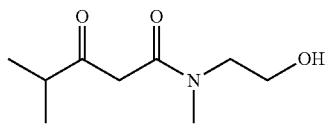

0.351 mol (50 ml) of 4-methyl-3-oxovaleric acid methyl ester and 0.369 mol (29.5 ml) 2-(methylamino)ethanol were stirred for 15 h at 120° C. in a Dean-Stark apparatus. 12 ml of methanol were collected. Subsequently, the excess starting materials 2 h were distilled off on a rotary evaporator (80° C. water bath, 1 mbar). There were obtained 64 g of the title compound.

IR (neat, cm$^{-1}$): 2969, 2934, 2875, 1713, 1621, 1491, 1466, 1401, 1384, 1358, 1303, 1265, 1211, 1120, 1072, 1048, 996, 926, 892, 862, 784, 726, 692, 615.

CHN-Elemental analysis: C, 52.00; H, 6.84; N, 6.01.

LC-MS: M+H$^+$, 188.7; M+Na$^+$, 210.6.

$^1$H-NMR (DMSO-d$_6$, 400 MHz): E/Z-Isomerie im Verhältnis ca. 45/55; Enol-Tautomer (20%), δ [ppm]=5.31, 5.28 (s, 1H), 3.55-3.42 (m, 2H), 3.42-3.25 (m, 2H), 3.0-2.8 (m, 3H), 2.4-2.3 (m, 1H), 1.07 (d, 6H); Keto-Tautomer (80%), δ=3.70, 3.66 (s, 2H), 3.55-3.42 (m, 2H), 3.42-3.25 (m, 2H), 2.94, 2.83 (s, 3H), 2.71, 2.70 (heptett, 1H), 1.02, 1.01 (d, 6H).

AAN. N,N,2-Trimethyl-3-oxobutanamide

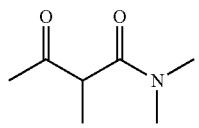

0.318 mol (50 ml) of ethyl 2-methylacetoacetic acid ester (ethyl 2-methyl-3-oxo-butanoate) (technical 90%) and 143 ml 33% dimethylamine in ethanol (about 0.795 mol dimethylamine) were stirred in a pressure reactor for 8 hours at 130° C. After cooling the reaction mixture was concentrated on a rotary evaporator, the residue was dissolved in 400 ml ethyl acetate and extracted 5 times with 150 ml of water. The combined water phases were evaporated in a rotary evaporator to dryness. 18.8 g of the title compound were obtained.

IR (neat, cm$^{-1}$): 2984, 2938, 1721, 1632, 1497, 1451, 1396, 1355, 1312, 1265, 1214, 1180, 1145, 1078, 1041, 952, 795, 770, 734, 689, 635, 623.

CHN-Elemental analysis: C, 71.21; H, 7.81; N, 6.39; O, 14.59.

LC-MS: M+H$^+$, 144.6; M+Na$^+$, 166.6.

$^1$H-NMR (DMSO-d$_6$, 400 MHz): δ [ppm]=3.92 (q, 1H); 3.03 (s, 3H); 2.84 (s, 3H); 2.06 (s, 3H); 1.12 (d, 3H).

AAO. N,N-Dimethyl-2-oxocyclohexancarboxamide

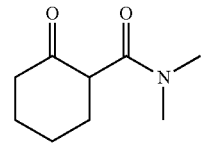

0.313 mol (50 ml) of ethyl cyclohexanone-2-carboxylate and 140 ml 33% dimethylamine in ethanol (about 0.78 mol dimethylamine) were stirred in a pressure reactor for 12 hours at 110° C. After cooling the reaction mixture was concentrated on a rotary evaporator, the residue was dissolved in 500 ml ethyl acetate and the organic phase was washed with 200 ml of 1 M NaOH and 3×50 ml water. The organic phase was then evaporated on a rotary evaporator to dryness. 46 g of the crude product was dissolved in 100 ml tert-butyl methyl ether and cooled to 0° C. Precipitated product was filtered off and dried, 3.6 g of the title compound were obtained.

IR (neat, cm$^{-1}$): 2939, 2867, 1691, 1639, 1496, 1454, 1442, 1429, 1409, 1396, 1342, 1316, 1287, 1261, 1208, 1155, 1130, 1096, 1067, 1038, 1012, 959, 923, 897, 870, 853, 808, 769, 696, 659, 623.

CHN-Elemental analysis: C, 71.21; H, 7.81; N, 6.39; O, 14.59.

LC-MS: M+H$^+$, 170.6; M+Na$^+$, 192.8.

$^1$H-NMR (DMSO-d$_6$, 400 MHz): δ [ppm]=3.86 (dd, 1H), 2.82 (s, 3H), 2.81 (s, 3H), 2.54-2.22 (m, 2H), 2.0-1.5 (m, 6H).

AAP. N,N-Dimethyl-2-oxocyclopentancarboxamide

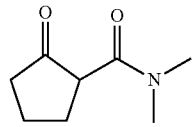

0.337 mol (50 ml) of ethyl 2-oxocyclopentanecarboxylate and 152 ml 33% dimethylamine solution in ethanol were stirred in a pressure reactor for 4 h at 110° C. The reaction mixture was then evaporated to dryness and the crude product was purified over 400 g silica gel with ethyl acetate/hexane 1/1. 17.7 g of the title compound were obtained.

IR (neat, cm$^{-1}$): 2955, 2884, 1735, 1634, 1494, 1455, 1396, 1320, 1260, 1198, 1167, 1140, 1101, 1059, 1025, 1004, 983, 946, 915, 904, 833, 752, 689, 623.

LC-MS: M+H$^+$, 156.7; M+Na$^+$, 178.6.

1H-NMR (DMSO-d$_6$, 400 MHz): δ [ppm]=3.72 (t, 1H); 3.03 (s, 3H); 2.83 (s, 3H); 2.3-1.4 (m, 6H).

AAQ. N-Cyclopentyl-3-oxobutanamide

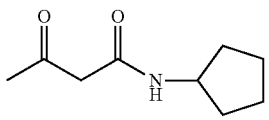

A solution of 21.3 g (0.25 mol) cyclopentylamine in 50 ml tetrahydrofuran was added dropwise at −5 to 0° C. to a solution of 20 g of diketene (0.24 mol) in 200 ml tetrahydrofuran. After 1 h stirring at 0° C. no more starting material was detected by thin layer chromatography. The reaction mixture was evaporated and the residue is recrystallized from 100 ml of ethyl acetate. This gave 31.4 g (0.19 mol, 78% yield) as a white solid.

IR (neat, cm$^{-1}$): 3256, 3083, 2947, 2919, 2868, 1719, 1647, 1626, 1556, 1422, 1357, 1197, 1161, 999.

LC-MS: 170 (M+H).

$^{1}$H-NMR (CDCl$_{3}$, 400 MHz): δ [ppm]=6.9 (1H), 4.2 (1H), 3.3 (2H), 2.2 (3H), 1.9 (2H), 1.6 (4H), 1.4 (2H).

AAR. 1-(Pyrrolidin-1-yl)butane-1,3-dione

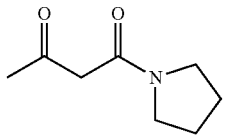

A solution of 21 ml (0.25 mol) of pyrrolidine in 50 ml tetrahydrofuran was added dropwise to a solution of 20 g of diketene (0.24 mol) in 200 ml tetrahydrofuran at −5 to 0° C. After 1 h stirring at 0° C. no more starting material was detected by thin layer chromatography. The reaction mixture was evaporated and the residue was purified by column chromatography. This gave 29.9 g (0.19 mol, 81% yield) of an oil.

IR (neat, cm$^{-1}$): 2972, 2875, 1719, 1633, 1589, 1481, 1433, 1381, 1356, 1226, 1193, 1159, 934, 776.

LC-MS: 156 (M+H), 178 (M+Na).

$^{1}$H-NMR (CDCl$_{3}$, 400 MHz): δ [ppm]=3.2 (5H), 2.1 (3H), 1.7 (5H).

AAS. Methyl N-(3-oxobutanoyl)-L-serinate

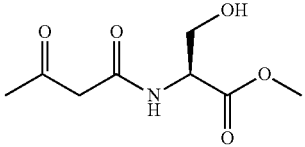

10.8 g (0.13 mol) of diketene, 20 g L-serine methyl ester hydrochloride (0.13 mol) and 21.6 g (0.26 mol, 2 eq) of NaHCO$_{3}$ were mixed in 1000 ml of THF at 0° C. Then the ice bath was removed and it was stirred further at room temperature. After 24 h stirring at room temperature, the reaction mixture was filtered and the residue was recrystallized from 100 ml of ethyl acetate. This gave 21.14 g (0.10 mol, 81% yield) as a white solid.

IR (neat, cm$^{-1}$): 3499, 3297, 2962, 1734, 1712, 1642, 1556, 1430, 1416, 1351, 1316, 1246, 1209, 1190, 1170, 1137, 1081, 1040, 978, 704.

LC-MS: 226 (M+Na), 187 (M−CH$_{3}$−H).

$^{1}$H-NMR (CDCl$_{3}$, 400 MHz): δ [ppm]=8.4 (1H), 5.1 (1H), 4.4 (1H), 3.7 bis 3.4 (7H), 2.1 (3H).

AAT. 1-(4-Acetylpiperazin-1-yl)butane-1,3-dione

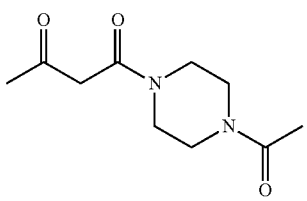

A solution of 20.8 g (0.17 mol) 1-acetylpiperazine in 50 ml tetrahydrofuran were added dropwise to a solution of 13 g of diketene (0.16 mol) in 200 ml tetrahydrofuran at −5 to 0° C. After 1 h stirring at 0° C. no more starting material was detected by thin layer chromatography. The reaction mixture was evaporated and the residue purified by column chromatography. This gave 27.2 g (0.13 mol, 83% yield) of a colorless oil.

IR (neat, cm$^{-1}$): 2919, 2864, 1718, 1631, 1422, 1358, 1307, 1284, 1248, 1159, 1063, 993.

LC-MS: 213 (M+H), 235 (M+Na).

$^{1}$H-NMR (CDCl$_{3}$, 400 MHz): δ [ppm]=3.6 (6H), 3.4 (3H), 3.3 (1H), 2.2 (3H), 2.1 (3H).

AAU. N-Cyclohexyl-3-oxobutanamide

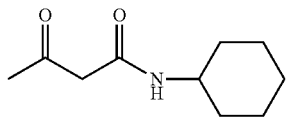

A solution of 23.6 g (0.24 mol) of cyclohexylamine in 50 ml tetrahydrofuran was added dropwise to a solution of 20 g of diketene (0.24 mol) in 200 ml tetrahydrofuran at −5 to 0° C. After 1 h stirring at 0° C. no more starting material was detected by thin layer chromatography. The reaction mixture was evaporated and the residue is recrystallized from 100 ml of ethyl acetate. This gave 30.0 g (0.16 mol, 69% yield) of a white solid.

IR (neat, cm$^{-1}$): 3259, 3088, 2929, 2852, 1716, 1648, 1627, 1560, 1449, 1427, 1359, 1346, 1193, 1162, 1105, 1001, 892, 751, 718.

LC-MS: 184 (M+H), 206 (M+Na).
¹H-NMR (CDCl₃, 400 MHz): δ [ppm]=6.9 (1H), 3.7 (1H), 3.3 (2H), 2.2 (3H), 1.9 (2H), 1.7 (2H), 1.6 (1H), 1.2 (2H), 1.1 (3H).

AAV. Methyl N-(3-oxobutanoyl)glycinate

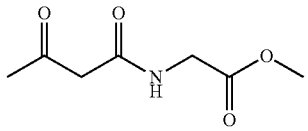

29.87 g (0.24 mol) of glycine methyl ester hydrochloride were added to a solution of 20.00 g (0.24 mol) of diketene in 250 ml toluene at 0° C. Then, 40.00 g (0.48 mol) NaHCO₃ were added and the reaction mixture was stirred overnight at room temperature. Since thin-layer chromatography detected no more starting material, the reaction mixture was filtered, evaporated and the residue purified by column chromatography. This gave 33.4 g (0.19 mol, 81% yield) oil.

IR (neat, cm⁻¹): 3346, 1750, 1708, 1669, 1538, 1399, 1360, 1320, 1278, 1198, 1165, 1024.
LC-MS: 174 (M+H), 196 (M+Na).
¹H-NMR (CDCl₃, 400 MHz): δ [ppm]=7.5 (1H), 4.0 (2H), 3.7 (3H), 3.4 (2H), 2.2 (3H).

AAW. N-(2-Methylpropyl)-3-oxobutanamide

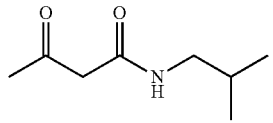

A solution of 18.20 g (0.25 mol) isobutylamine in 50 ml tetrahydrofuran was added dropwise to a solution of 20 g of diketene (0.24 mol) in 200 ml tetrahydrofuran at −5 to 0° C. After 1 h stirring at 0° C. no more starting material was detected by thin layer chromatography. The reaction mixture was evaporated and the residue is recrystallized from 100 ml of ethyl acetate. This gave 26.93 g (0.17 mol, 72% yield) of a white solid.

IR (neat, cm⁻¹): 3269, 3098, 2964, 2875, 1711, 1640, 1574, 1473, 1414, 1355, 1328, 1271, 1190, 1160, 976, 823, 764, 727.
LC-MS: 158 (M+H), 180 (M+Na).
¹H-NMR (CDCl₃, 400 MHz): δ [ppm]=7.1 (1H), 4.3 (2H), 3.1 (2H), 2.2 (3H), 1.7 (1H), 0.9 (6H).

AAX. N-(Cyclopropylmethyl)-3-oxobutanamide

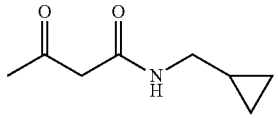

A solution of 15.1 g (0.22 mol) cyclopropylmethylamine in 50 ml tetrahydrofuran was added dropwise to a solution of 17 grams of diketene (0.20 mol) in 200 ml tetrahydrofuran at −5 to 0° C. After 1 h stirring at 0° C. no more starting material was detected by thin layer chromatography. The reaction mixture was evaporated and the residue is recrystallized from 100 ml of ethyl acetate. This gave 19.7 g (0.13 mol, 63% yield) of a white solid.

IR (neat, cm⁻¹): 3255, 3083, 3008, 2932, 1712, 1640, 1415, 1356, 1326, 1276, 1191, 1160, 1079, 1017, 830, 800, 775, 729.
LC-MS: 156 (M+H), 178 (M+Na).
¹H-NMR (CDCl₃, 400 MHz): δ [ppm]=7.0 (1H), 3.4 (2H), 3.1 (2H), 2.3 (3H), 0.9 (1H), 0.5 (2H), 0.1 (2H).

AAY. Ethyl 4-(morpholin-4-yl)-2,4-dioxobutanoate

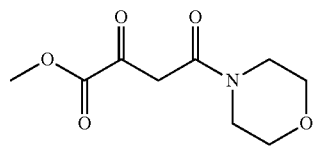

10.2 g of diisopropylamine (0.1 mol) was placed in 100 ml dry THF under nitrogen and cooled in a freezing mixture. 40 ml n-butyllithium in hexane (2.5 M, 0.1 mol) was slowly added dropwise. When the addition was completed the mixture was allowed to stir for 60 minutes and then acetylmorpholine 12.9 g (0.1 mol) was added dropwise. The reaction mixture was stirred for 20 min in the freezing mixture. In a second flask, 43.7 g of diethyl oxalate (0.3 mol) in 50 ml of dry THF was cooled in a freezing mixture and the cooled reaction mixture was cannulated with stirring in small portions to it. It was left overnight under stirring to warm to room temperature. The THF was removed on a rotary evaporator and the residue was taken up in 80 ml half concentrated hydrochloric acid. The aqueous phase was extracted five times with 150 ml ethyl acetate, and the combined organic phases were dried over sodium sulfate and concentrated on a rotary evaporator to dryness. The excess diethyl oxalate was removed by distillation (2-3 mbar, 80° C.). 5.0 g of product were obtained in the form of white crystals with a melting point of 60° C. after crystallization from PE (petrol ether).

IR (neat, cm⁻¹): 2998, 2980, 2915, 2873, 1722, 1632, 1585, 1489, 1446, 1396, 1375, 1271, 1236, 1136, 1113, 1072, 1054, 1019, 981, 917, 874, 858, 837, 825, 766, 723, 639.
¹H-NMR (CDCl₃, 400 MHz): δ [ppm]=1.35 (3H), 3.50-3.73 (8H), 4.33 (2H), 6.20 (1H), 14.32 (1H).

AAZ. Ethyl N-(3-oxobutanoyl)-L-alaninate

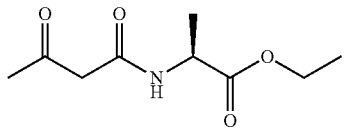

20.00 g (0.13 mol) of ethyl (2S)-2-aminopropanoate hydrochloride were added to a solution of 10.95 g (0.13 mol) of diketene in 500 ml toluene at 0° C. Then, 21.90 g (0.26 mol) NaHCO₃ was added and the reaction mixture was stirred overnight at room temperature. Since no more starting material was detected by thin-layer chromatography, the reaction mixture was filtered, evaporated and the residue purified by column chromatography. This gave 19.36 g (0.096 mol, 74% yield) of a colorless oil.

IR (neat, cm$^{-1}$): 3308, 2985, 1720, 1647, 1537, 1453, 1360, 1205, 1155, 1056, 1021.

$^1$H-NMR (CDCl$_3$, 400 MHz): δ [ppm]=7.4 (1H), 4.5 (1H), 4.1 (2H), 3.4 (2H), 2.2 (3H), 1.3 (3H), 1.2 (3H).

ABA. N-Cyclobutyl-3-oxobutanamide

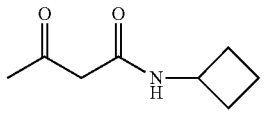

A solution of 20.00 g (0.28 mol) cyclobutylamine in 50 ml tetrahydrofuran was added dropwise to a solution of 22.00 g of diketene (0.26 mole) in 200 ml tetrahydrofuran at −5 to 0° C. After 1 h stirring at 0° C. no more starting material was detected by thin layer chromatography. The reaction mixture was evaporated and the residue is recrystallized from 100 ml of ethyl acetate. This gave 24.60 g (0.16 mol, 61% yield) of a white solid.

IR (neat, cm$^{-1}$): 3251, 3080, 2974, 2949, 1721, 1649, 1626, 1554, 1423, 1356, 1341, 1243, 1216, 1162, 994, 748, 717.

LC-MS: 156 (M+H), 178 (M+Na).

$^1$H-NMR (CDCl$_3$, 400 MHz): δ [ppm]=7.2 (1H), 4.3 (1H), 3.3 (2H), 2.3 (5H), 2.8 (2H), 2.6 (2H).

ABB. 1-(Azetidin-1-yl)-butane-1,3-dione

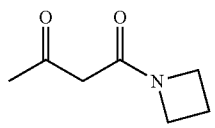

A solution of 18.00 g (0.31 mol) azetidine in 50 ml tetrahydrofuran was added dropwise to a solution of 25.00 g of diketene (0.30 mol) in 200 ml tetrahydrofuran at −5 to 0° C. After 1 h stirring at 0° C. no more starting material was detected by thin layer chromatography. The reaction mixture was evaporated and the residue is recrystallized from 100 ml of ethyl acetate. This gave 26.45 g (0.19 mol, 63% yield) of a white solid.

IR (neat, cm$^{-1}$): 3107, 2983, 2958, 2885, 1718, 1631, 1462, 1443, 1410, 1367, 1306, 1298, 1237, 1188, 1168, 1154, 1112, 1014, 851, 736.

LC-MS: 142 (M+H), 164 (M+Na).

$^1$H-NMR (CDCl$_3$, 400 MHz): δ [ppm]=4.1 (2H), 3.9 (2H), 3.1 (2H), 2.1 (5H).

ABC. Ethyl 1-(3-oxobutanoyl)-piperidine-4-carboxylate

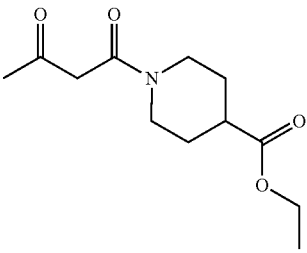 [SMILES: CCOC(=O)C1CCN(C(=O)CC(C)=O)CC1]

A solution of 18.70 g (0.12 mol) ethyl 4-piperidinecarboxylate in 50 ml tetrahydrofuran was added dropwise to a solution of 10.00 g of diketene (0.12 mol) in 200 ml tetrahydrofuran at −5 to 0° C. After 1 h stirring at 0° C. no more starting material was detected by thin layer chromatography. The reaction mixture was evaporated and the residue purified by column chromatography.

This gave 19.52 g (0.081 mol, 68% yield) of a colorless oil.

IR (neat, cm$^{-1}$): 2957, 2932, 2863, 1721, 1634, 1446, 1314, 1272, 1250, 1173, 1158, 1110, 1097, 1039, 939.

$^1$H-NMR (CDCl$_3$, 400 MHz): δ [ppm]=4.3 (1H), 4.1 (2H), 3.7 (1H), 3.5 (2H), 3.1 (1H), 2.9 (1H), 2.5 (1H), 2.2 (3H), 1.9 (2H), 1.6 (2H), 1.2 (3H).

ABD. 1-(4-Hydroxypiperidin-1-yl)-4-methoxybutane-1,3-dione

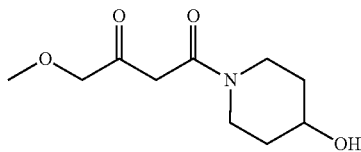

0.34 mol (48.7 g) of methyl 4-methoxy-acetoacetate and 0.36 mol (36.0 g) of 4-hydroxypiperidine were stirred for 5 h at 120° C. at a Dean-Stark apparatus. 45 g of the crude product was purified over 1 kg of silica gel with ethyl acetate/ethanol 9/1. 23.7 g of the title compound were obtained.

IR (neat, cm$^{-1}$): 2931, 1729, 1618, 1448, 1365, 1310, 1266, 1201, 1132, 1101, 1072, 1025, 977, 935, 809, 776, 716, 681.

LC-MS: M+H$^+$, 216.8; M+Na$^+$, 238.7.

$^1$H-NMR (DMSO-d$_6$, 400 MHz): Enol-Tautomer (14%), δ [ppm]=15.10 (s, 1H), 5.56 (s, 1H), 4.76 (d (J=4 Hz), 1H), 3.90 (s, 2H), 3.9-2.9 (m, 5H), 3.29 (s, 3H), 1.8-1.1 (m, 4H); Keto-Tautomer (86%), δ [ppm]=4.73 (d (J=4 Hz), 1H), 4.10 (s, 2H), 3.9-2.9 (m, 5H), 3.57 (s, 2H), 3.27 (s, 3H), 1.8-1.1 (m, 4H).

Testing Method:

The excellent Fe utilizations that can be accomplished through the Fe complexes according to the invention were measured by means of the following mouse model.

Male NMRI (SPF) mice (approximately 3 weeks old) were fed a low-iron diet (approx. 5 ppm iron) for approximately 3 weeks. The iron complexes were then administered to them by means of a stomach tube (2 mg iron/kg body weight/day)

for 2 times 5 days, with an interruption of 2 days (days 1-5 and 8-12). Utilization on day 15 was calculated from the hemoglobin increase and the body weight increase in accordance with the formula $$\text{Utilization (\%)} = \frac{\Delta \text{ iron utilization} * 100}{Fe\ Dos.} =$$
$$\frac{(Fe\ ut. - Fe\ ut.\ \text{Control}) * 100}{Fe\ Dos.} = [(Hb_{2(3)} * BW_{9(14)} - Hb_1 * BW_4) *$$
$$0.07 * 0.0034 - (Hb_{2(3)\ Control} * BW_{9(14)\ Control} -$$
$$Hb_{1\ Control} * BW_{4\ Control}) * 0.07 * 0.0034)] *$$
$$100/Fe\ Dos. = [(Hb_{2(3)} * BW_{9(14)} - Hb_1 * BW_4) * 0.000238 -$$
$$(Hb_{2(3)\ Control} * BW_{9(14)\ Control} - Hb_{1\ Control} * BW_{4\ Control}) * 0.000238] *$$
$$100/Fe\ Dos. =$$
$$(Hb_{2(3)} * BW_{9(14)} - Hb_1 * BW_4 - Hb_{2(3)\ Control} * BW_{9(14)\ Control} +$$
$$Hb_{1\ Control} * BW_{4\ Control}) * 0.0238/Fe\ Dos.$$

0.07=Factor for 70 ml blood per kg body weight (BW)
0.0034=Factor for 0.0034 g Fe/g Hb
$Hb_1$=Hemoglobin level (g/l) on day 1
$Hb_{2(3)}$=Hemoglobin level (g/l) on day 8 (or 15)
$BW_4$=body weight (g) on day 1
$BW_{9(14)}$=body weight (g) on day 8 (or 15)
$Hb_{1\ Control}$=average hemoglobin level (g/l) on day 1 in the control group,
$Hb_{2(3)\ Control}$=average hemoglobin level (g/l) on day 8 (or 15) in the control group,
$BW_{4\ Control}$=average body weight (g) on day 1 in the control group,
$BW_{9(14)\ Control}$=average body weight (g) on day 8 (or 15) in the control group,
Fe Dos.=entire administered iron (mg Fe) over 5 or 10 days,
Fe ut.=$(Hb_{2(3)}*BW_{9(14)}-Hb_1*BW_4)*0.07*0.0034$ (mg Fe)
ΔUtilization=Fe tot. utilized (examined group)−Fe ut. Control group, utilized from food, (mg Fe)

TABLE

| Example-No. | Utilization n 15 d (abs. %) |
|---|---|
| 1 | 61 |
| 2 | 41 |
| 3 | 95 |
| 4 | 90 |
| 5 | 61 |
| 6 | 57 |
| 7 | 41 |
| 8 | 69 |
| 9 | 54 |
| 10 | 45 |
| 11 | 75 |
| 12 | 35 |
| 13 | 71 |
| 14 | 68 |
| 15 | 68 |
| 16 | 60 |
| 17 | 48 |
| 18 | 81 |
| 19 | 73 |
| 20 | 77 |
| 21 | — |
| 22 | 78 |
| 23 | 88 |
| 24 | 70 |
| 25 | 60 |
| 26 | 64 |

TABLE-continued

| Example-No. | Utilization n 15 d (abs. %) |
|---|---|
| 27 | 88 |
| 28 | 73 |
| 29 | 79 |
| 30 | — |
| 31 | 71 |
| 32 | 81 |
| 33 | 69 |
| 34 | 32 |
| 35 | 44 |
| 36 | 79 |
| 37 | 34 |
| 38 | 77 |
| 39 | 66 |
| 40 | 87 |
| 41 | 68 |
| 42 | 30 |
| 43 | 75 |
| 44 | 73 |
| 45 | — |
| 46 | 78 |
| 47 | 61 |
| 48 | 53 |
| 49 | — |
| 50 | — |
| 51 | 78 |
| 52 | 84 |
| 53 | — |
| 54 | 76 |
| 55 | 84 |
| 56 | — |
| 57 | — |
| 58 | — |
| 59 | 80 |
| 60 | 80 |
| 61 | 73 |
| 62 | 68 |
| 63 | 71 |
| 64 | 79 |
| 65 | 73 |
| 66 | — |

"—" means: not determined.

PREPARATION EXAMPLES

Example 1

Tris-(3-oxobutaneamide)-iron(III) complex

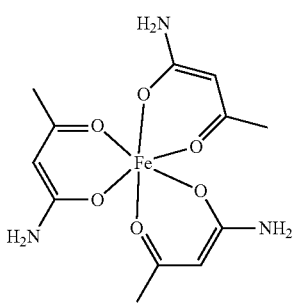

A solution of 24.00 g (0.15 mol) iron(III) chloride (anhydrous) in 400 ml ethanol was added dropwise to a solution of 45.00 g (0.45 mol) 3-oxobutaneamide in 400 ml ethanol. 37.46 g (0.45 mol) sodium bicarbonate was then added in portions. After 4 hours of stirring at room temperature, the reaction mixture was filtrated off, the filtrate spun off and the residue dried overnight in the drying cabinet at 50° C. 51.63 g of product was obtained as a black-red solid.

IR (in substance, cm$^{-1}$): 3317, 3187, 1618, 1569, 1507, 1415, 1328, 1194, 1092, 1034, 978, 935, 780.

Elemental analysis: C, 37.41; H, 5.78; N, 8.80.

Fe content 15.80% [m/m].

Example 2

Tris-(N,N-diethyl-3-oxobutaneamide)-iron(III) complex

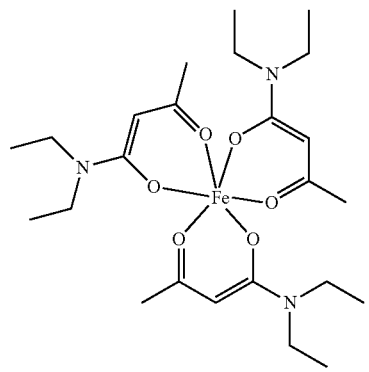

A solution of 1.00 g (6.17 mmol) iron(III) chloride (anhydrous) in 10 ml ethanol was added dropwise to a solution of 2.90 g (18.50 mmol) N,N-diethyl-3-oxobutaneamide in 30 ml ethanol. 3.11 g (37.00 mmol) sodium bicarbonate was then added in portions. After 2 hours of stirring at room temperature, the reaction mixture was filtrated off, the filtrate spun off and the residue dried overnight in the drying cabinet at 50° C. 3.50 g of product was obtained as a black-red oil.

IR (in substance, cm$^{-1}$): 2973, 2932, 1597, 1557, 1511, 1492, 1454, 1434, 1374, 1356, 1309, 1274, 1204, 1163, 1082, 1004, 962.

Elemental analysis: C, 53.54; H, 8.00; N, 7.88.

Fe content 9.63% [m/m].

Example 3

Tris-(N,N-dimethyl-3-oxobutaneamide)-iron(III) complex

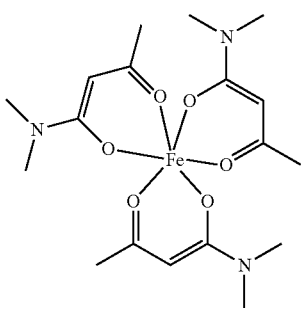

A solution of 3.00 g (18.50 mmol) iron(III) chloride (anhydrous) in 50 ml ethanol was added dropwise to a solution of 8.96 g (55.50 mmol, 80% in water) N,N-dimethyl-3-oxobutaneamide in 50 ml ethanol. 4.66 g (55.50 mmol) sodium bicarbonate was then added in portions. After 4 hours of stirring at room temperature, the reaction mixture is filtrated off, washed with 10 ml EtOH, the filtrate spun off and the residue dried overnight in the drying cabinet at 50° C. 8.37 g of product was obtained as a black-red oil.

IR (in substance, cm$^{-1}$): 2918, 1720, 1643, 1557, 1523, 1490, 1433, 1401, 1347, 1260, 1211, 1177, 1061, 1032, 989, 955.

Elemental analysis: C, 47.39; H, 6.70; N, 9.22.

Fe content 11.13% [m/m].

Example 4

Tris-(N-methyl-3-oxobutaneamide)-iron(III) complex

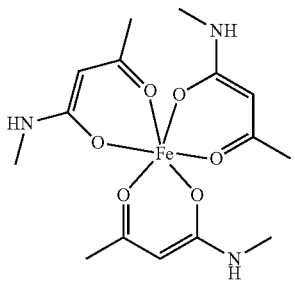

A solution of 3.00 g (18.50 mmol) iron(III) chloride (anhydrous) in 50 ml ethanol was added dropwise to a solution of 9.13 g (55.50 mmol, 80% in water) N-methyl-3-oxobutaneamide in 50 ml ethanol. 4.66 g (55.50 mmol) sodium bicarbonate was then added in portions. After 2 hours of stirring at room temperature, the reaction mixture was filtrated off, washed with 10 ml EtOH, the filtrate spun off and the residue dried overnight in the drying cabinet at 50° C. 7.98 g of product was obtained as a black-red solid.

IR (in substance, cm$^{-1}$): 3336, 3119, 2913, 1558, 1500, 1448, 1411, 1275, 1191, 1157, 1104, 1010, 959, 935, 779.

Elemental analysis: C, 42.23; H, 5.78; N, 9.70.

Fe content 12.46% [m/m].

Example 5

Tris(3-oxo-2-(piperidin-1-ylcarbonyl)butanenitrile)-iron(III) complex

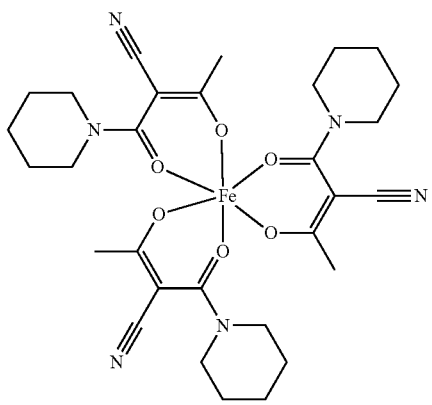

1.4 g (8.5 mmol) FeCl$_3$ (anhydrous) dissolved in 20 ml ethanol 99% were added to a solution of 5.0 g (25.7 mmol) 2,4-dioxo-3-cyanobutylpiperidin in 40 ml EtOH 99%. 2.2 g (25.6 mmol) NaHCO$_3$ were then added and this was followed by stirring for 1 hour at 20-25° C. The reaction mixture is filtrated, the filtrate concentrated to dryness on the rotavap at 50° C./<100 mbar, and the residue was dried in the vacuum drying cabinet for at least 15 hours at 50° C./<100 mbar. The obtained solid was suspended in 200 ml water for approx. 30 min with an Ultraturax, filtrated off and again dried in the vacuum drying cabinet for at least 15 hours at 50° C./<100 mbar. 5.3 g of product was obtained as an orange solid.

IR (in substance, cm$^{-1}$): 2936, 2858, 2197, 1594, 1532, 1506, 1439, 1387, 1270, 1217, 1169, 1145, 1072, 1020, 973, 905, 854, 755, 700, 653.

Elemental analysis: C, 57.0; H, 6.40; N, 12.60.
Fe content 8.30% [m/m].

Example 6

Tris-(2-chloro-N-methyl-3-oxobutaneamide)-iron(III) complex

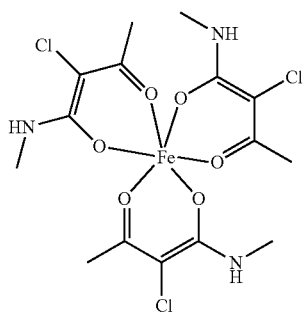

A solution of 1.00 g (6.17 mmol) iron(III) chloride anhydrous in 10 ml ethanol was added dropwise to a solution of 2.77 g (18.50 mmol) 2-chloro-N-methyl-3-oxobutaneamide in 30 ml ethanol. 1.55 g (18.50 mmol) sodium bicarbonate was then added in portions. After 2 hours of stirring at room temperature, the reaction mixture was filtrated off, washed with 10 ml EtOH, the filtrate spun off and the residue dried overnight in the drying cabinet at 50° C. 3.19 g of product was obtained as a violet solid.

IR (in substance, cm$^{-1}$): 3359, 2942, 1545, 1468, 1406, 1375, 1260, 1155, 1118, 1028, 935, 796, 748.

Elemental analysis: C, 33.42; H, 4.23; N, 7.74.
Fe content 10.72% [m/m].

Example 7

Tris(N-butyl-3-oxobutaneamide)-iron(III) complex

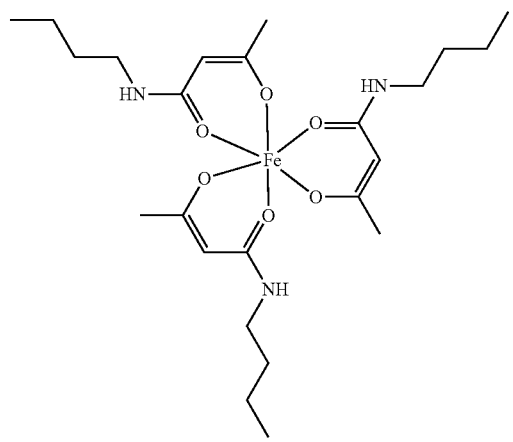

1.4 g (8.6 mmol) FeCl$_3$ (anhydrous) dissolved in 10 ml methanol were added to a solution of 5 g (31.8 mmol) N-n-butyl-3-oxo-butaneamide in 40 ml toluene. 4.4 g (52.4 mmol) NaHCO$_3$ and 2.2 g (15.5 mmol) Na$_2$SO$_4$ (anhydrous) were then added and this was followed by stirring for 1 hour at 20-25° C. The reaction mixture was filtrated, the filtrate concentrated to dryness on the rotavap at 50° C./<100 mbar, and the residue was dried in the vacuum drying cabinet for at least 15 hours at 50° C./<100 mbar. 5.0 g of product was obtained as a red solid.

IR (in substance, cm$^{-1}$): 2935, 1645, 1592, 1533, 1508, 1439, 1387, 1270, 1219, 1143, 1073, 1020, 973, 909, 855, 822, 699, 652.

Fe content 9.0% [m/m].

Example 8

Tris(N,N-dibutyl-3-oxobutaneamide)-iron(III) complex

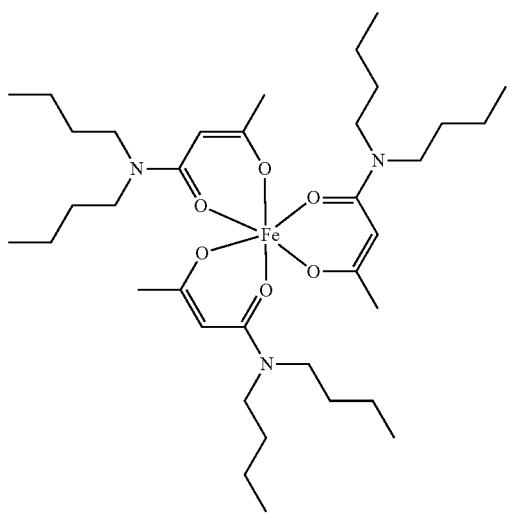

48.5 g (0.23 mol) N,N-dibutyl-3-oxo-butaneamide and 20.6 g (0.08 mol) FeCl$_3$×6H$_2$O were provided in 245 ml ethanol 96%. 14.1 g (0.13 mol) Na$_2$CO$_3$ (anhydrous) was added in several portions within approx. 5 min. The reaction container is cooled in the process with a water bath of approx. 20° C. The reaction mixture was stirred for 6 hours at 20-25° C., subsequently filtrated over a glass frit and concentrated to dryness on the rotavap at 50° C./<100 mbar. The oily product was dried for at least 15 hours at 20-25° C. under a high vacuum. 50 g of product was obtained as a red-brown oil.

IR (in substance, cm$^{-1}$): 2957, 2931, 2872, 1596, 1558, 1513, 1492, 1461, 1431, 1366, 1292, 1257, 1229, 1199, 1155, 1112, 1007, 956, 764.

CHN elemental analysis: C, 61.10; H, 9.60; N, 6.00.
Fe content 8.00% [m/m].

Example 9

Tris-(1-(piperidin-1-yl)-butane-1,3-dione)-iron(III) complex

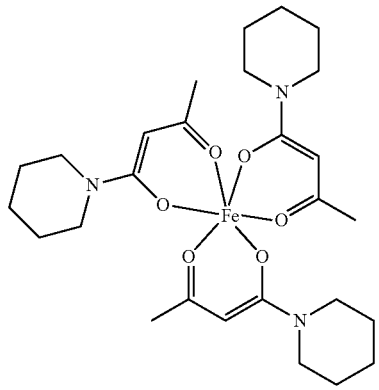

A solution of 1.00 g (6.17 mol) iron(III) chloride (anhydrous) in 10 ml ethanol was added dropwise to a solution of 3.13 g (18.50 mmol) 1-(piperidin-1-yl)-butane-1,3-dione in 40 ml ethanol. 6.26 g (74.00 mmol) sodium bicarbonate was then added in portions. After 2 hours of stirring at room temperature, the reaction mixture was filtrated off, washed with 10 ml EtOH, the filtrate spun off and the residue dried overnight in the drying cabinet at 50° C. 3.72 g of product was obtained as a black oil.

IR (in substance, cm$^{-1}$): 2930, 2852, 1594, 1556, 1509, 1483, 1461, 1442, 1374, 1347, 1256, 1231, 1205, 1022, 958.

Elemental analysis: C, 55.33; H, 7.49; N, 7.01.
Fe content 9.30% [m/m].

Example 10

Tris(3-oxoheptaneamide)-iron(III) complex

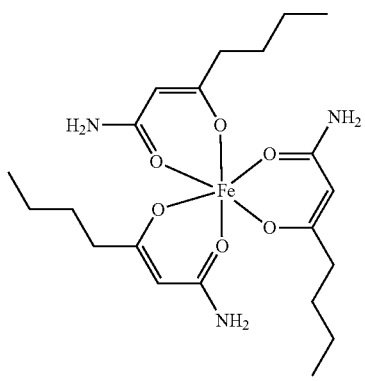

15 mmol (2.147 g) 3-oxoheptaneamide were dissolved in 50 ml ethanol (anhydrous) in a 100 ml Erlenmeyer flask with a drying tube, and 5 mmol (0.811 g) FeCl$_3$ (anhydrous) was added. 20 mmol (1.68 g) NaHCO$_3$ was added after 5 min and stirring was continued for another 2 hours. pH monitoring showed pH 3.78 after 2 hours (sample was filtrated and diluted with water; pH 2.78 after 0.5 hours; 3.19 after 1 hour; 3.56 after 1.5 hours). The reaction mixture was filtrated, the filtrate was concentrated on the rotavap and the product was dried under an oil pump vacuum. 2.25 g of product was obtained.

IR (in substance, cm$^{-1}$): 3318, 3195, 2956, 2930, 2870, 1715, 1617, 1564, 1507, 1458, 1355, 1192, 1093, 946, 780, 663.

Elemental analysis: C, 49.06; H, 7.45; N, 8.28.
Fe content 10.91% [m/m].

Example 11

Tris(N-methyl-3-oxoheptaneamide)-iron(III) complex

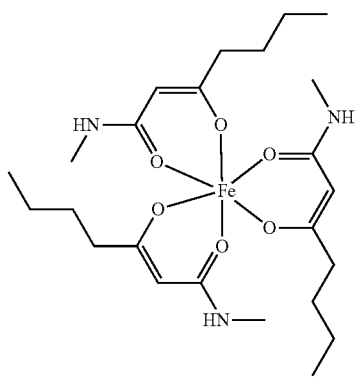

8.3 mmol (1.37 g) 3-oxoheptanoic acid methylamide were dissolved in 40 ml ethanol (anhydrous) in a 100 ml Erlenmeyer flask with a drying tube, and 2.8 mmol (0.447 g) FeCl$_3$ (anhydrous) was added. 11 mmol (0.927 g) NaHCO$_3$ was added, followed by stirring for 2.5 hours. pH monitoring showed pH 3.8 after 2.5 hours (sample was filtrated and diluted with water). The reaction mixture was filtrated, the filtrate was concentrated on the rotavap and the product was dried at 50° C. in the vacuum drying cabinet. 1.20 g of product was obtained.

IR (in substance, cm$^{-1}$): 3283, 3117, 2956, 2932, 2871, 1718, 1561, 1502, 1420, 1377, 1271, 1157, 1108, 1082, 967, 937, 886, 779, 649.

Elemental analysis: C, 52.2; H, 7.65; N, 7.61.

Fe content 9.14% [m/m].

Example 12

Tris-(N,N-bis-(2-hydroxyethyl)-3-oxobutaneamide)-iron(III) complex

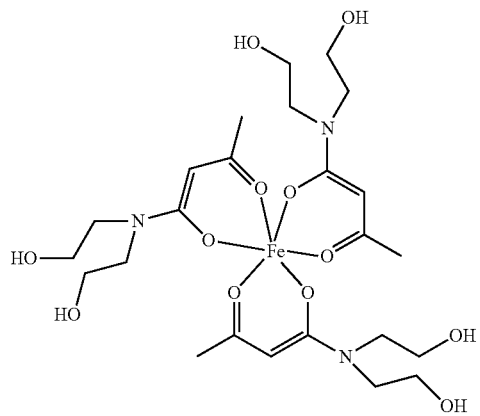

A solution of 1.00 g (6.17 mmol) iron(III) chloride (anhydrous) in 10 ml ethanol was added dropwise to a solution of 3.50 g (18.50 mmol) N,N-bis-(2-hydroxyethyl)-3-oxobutaneamide in 30 ml ethanol. 1.56 g (18.50 mmol) sodium bicarbonate was then added in portions. After 4 hours of stirring at room temperature, the reaction mixture was filtrated off, washed with 10 ml EtOH, the filtrate spun off and the residue dried overnight in the drying cabinet at 50° C. 4.19 g of product was obtained as a black oil.

IR (in substance, cm$^{-1}$): 3327, 2974, 2934, 2880, 1632, 1567, 1516, 1494, 1438, 1361, 1301, 1228, 1206, 1170, 1052.

Elemental analysis: C, 43.61; H, 7.46; N, 5.34.

Fe content 8.14% [m/m].

Example 13

Tris-(N-butyl-N-methyl-3-oxobutaneamide)-iron(III) complex

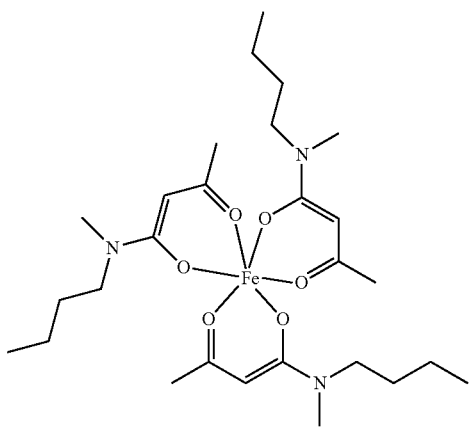

A solution of 0.50 g (3.08 mmol) iron(III) chloride (anhydrous) in 5 ml ethanol was added dropwise to a solution of 1.58 g (9.25 mmol) N-n-butyl-N-methyl-3-oxobutyramide in 15 ml ethanol. 0.78 g (9.25 mmol) sodium bicarbonate was then added in portions. After 4 hours of stirring at room temperature, the reaction mixture was filtrated off, washed with 10 ml EtOH, the filtrate spun off and the residue dried overnight in the drying cabinet at 50° C. 1.80 g of product was obtained as a black oil.

IR (in substance, cm$^{-1}$): 2956, 2930, 2871, 1598, 1557, 1515, 1492, 1464, 1353, 1308, 1230, 1211, 1088, 957.

Elemental analysis: C, 55.26; H, 8.25; N, 7.21.

Fe content 9.36% [m/m].

Example 14

Tris-(1-(4-hydroxypiperidin-1-yl)-butane-1,3-dione)-iron(III) complex

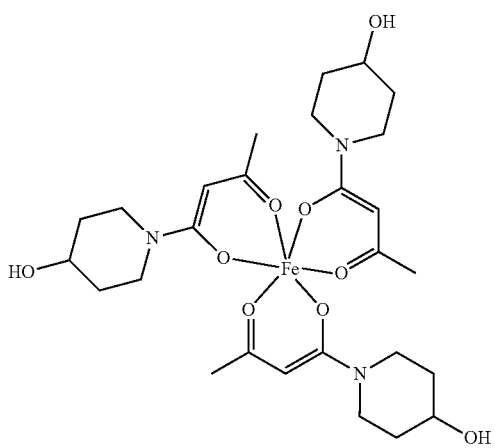

A solution of 1.00 g (6.17 mol) iron(III) chloride (anhydrous) in 10 ml ethanol was added dropwise to a solution of 3.43 g (18.51 mmol) 1-(4-hydroxypiperidin-1-yl)-butane-1, 3-dione in 30 ml ethanol. 3.11 g (37.00 mmol) sodium bicarbonate was then added in portions. After 4 hours of stirring at room temperature, the reaction mixture was filtrated off, washed with 10 ml EtOH, the filtrate spun off and the residue dried overnight in the drying cabinet at 50° C. 3.98 g of product was obtained as a brown solid.

IR (in substance, cm$^{-1}$): 3334, 2923, 2859, 1589, 1554, 1509, 1485, 1443, 1362, 1265, 1227, 1205, 1054, 1023, 954.

Elemental analysis: C, 51.47; H, 7.26; N, 6.37.

Fe content 8.28% [m/m].

Example 15

Tris-(3-oxo-N,N-dipropylbutaneamide)-iron(III) complex

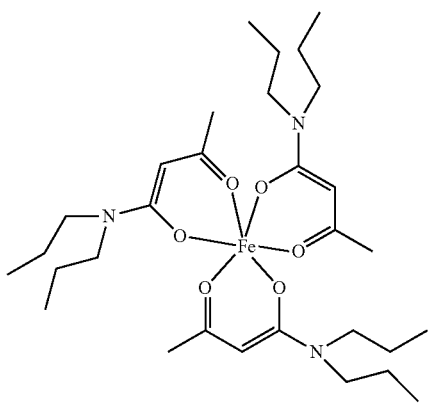

A solution of 0.50 g (3.08 mmol) iron(III) chloride (anhydrous) in 5 ml ethanol was added dropwise to a solution of 1.71 g (9.25 mmol) 3-oxo-N,N-di-n-propylbutaneamide in 20 ml ethanol. 1.56 g (18.50 mmol) sodium bicarbonate was then added in portions. After 2 hours of stirring at room temperature, the reaction mixture was filtrated off, washed with 10 ml EtOH, the filtrate spun off and the residue dried overnight in the drying cabinet at 50° C. 1.94 g of product was obtained as a brown oil.

IR (in substance, cm$^{-1}$): 2962, 2931, 2874, 1597, 1557, 1510, 1491, 1468, 1456, 1431, 1367, 1299, 1246, 1202, 1164, 1102, 1058, 996, 958.

Elemental analysis: C, 56.93; H, 8.73; N, 6.50.

Fe content 8.15% [m/m].

Example 16

Tris-(N-hexyl-3-oxobutaneamide)-iron(III) complex

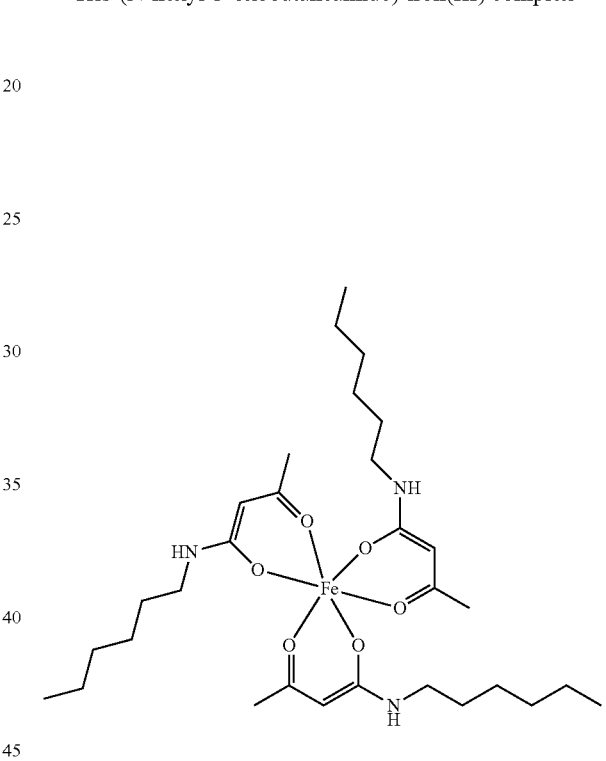

A solution of 1.00 g (6.17 mmol) iron(III) chloride (anhydrous) in 5 ml ethanol was added dropwise to a solution of 3.43 g (18.50 mmol) N-n-hexyl-3-oxobutaneamide in 25 ml ethanol. 3.12 g (37.00 mmol) sodium bicarbonate was then added in portions. After 4 hours of stirring at room temperature, the reaction mixture was filtrated off, washed with 10 ml EtOH, the filtrate spun off and the residue dried overnight in the drying cabinet at 50° C. 3.86 g of product was obtained as a brown oil.

IR (in substance, cm$^{-1}$): 3289, 2956, 2926, 2857, 1719, 1656, 1589, 1556, 1503, 1453, 1434, 1410, 1274, 1188, 1037, 1017, 960, 946.

Fe content 8.34% [m/m].

Example 17

Tris(N,N-dimethyl-3-oxoheptaneamide)-iron(III) complex

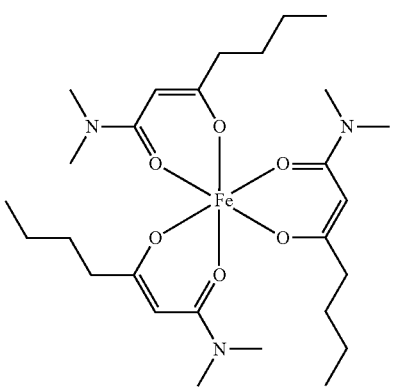

In analogy to the preceding examples, the tris(N,N-dimethyl-3-oxoheptaneamide)-iron(III) complex was prepared starting with iron(III) chloride and 3-oxo-heptanoic acid dimethylamide.

Example 18

Tris(3-oxopentaneamide)-iron(III) complex

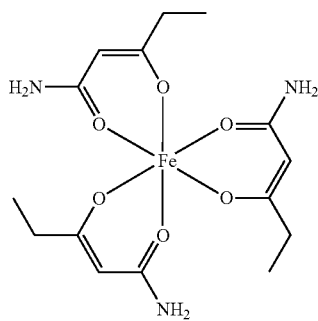

15.0 mmol (1.73 g) 3-oxopentaneamide were dissolved in 100 ml ethanol (anhydrous) in a 250 ml round-bottomed flask with a drying tube, and 5.0 mmol (0.811 g) FeCl$_3$ (anhydrous) was added. 20 mmol (1.68 g) NaHCO$_3$ was added, followed by stirring for 3 hours. pH monitoring showed pH 5.2 (sample was filtrated and diluted with water). The reaction mixture was filtrated, the filtrate was concentrated on the rotavap and the product was dried at 50° C. in the vacuum drying cabinet. 2.1 g of product was obtained.

IR (in substance, cm$^{-1}$): 3318, 3189, 2974, 2938, 2361, 1715, 1625, 1567, 1509, 1458, 1341, 1299, 1242, 1184, 1107, 1077, 1020, 952, 917, 804, 785.

Elemental analysis: C, 39.86; H, 5.821; N, 9.28.

Fe content 11.85% [m/m].

Example 19

Tris(N,N-dimethyl-3-oxopentaneamide)-iron(III) complex

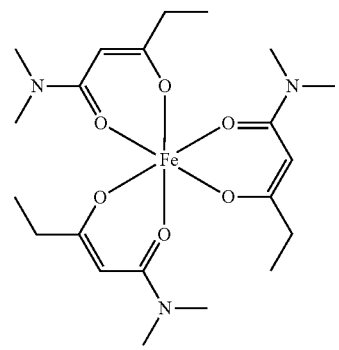

15.0 mmol (2.15 g) N,N-dimethyl-3-oxopentaneamide were dissolved in 75 ml ethanol (anhydrous) in a 100 ml round-bottomed flask with a drying tube, and 5.0 mmol (0.811 g) FeCl$_3$ (anhydrous) was added. 20 mmol (1.68 g) NaHCO$_3$ was added, followed by stirring for 1.5 hours. pH monitoring showed pH 4.2 (sample was filtrated and diluted with water). The reaction mixture was filtrated, the filtrate was concentrated on the rotavap and the product was dried at 50° C. in the vacuum drying cabinet. 2.4 g of product was obtained.

IR (in substance, cm$^{-1}$): 2965, 2933, 2871, 2362, 1720, 1596, 1553, 1526, 1492, 1428, 1402, 1371, 1352, 1311, 1259, 1197, 1175, 1061, 1020, 983, 932, 835, 798, 766, 718, 688.

Elemental analysis: C, 50.35; H, 7.307; N, 8.31.

Fe content 10.50% [m/m].

Example 20

Tris-(ethyl N-(3-oxobutanoyl)glycinate)-iron(III) complex (Tris((3-Oxo-butyrylamino)ethyl acetate) iron)

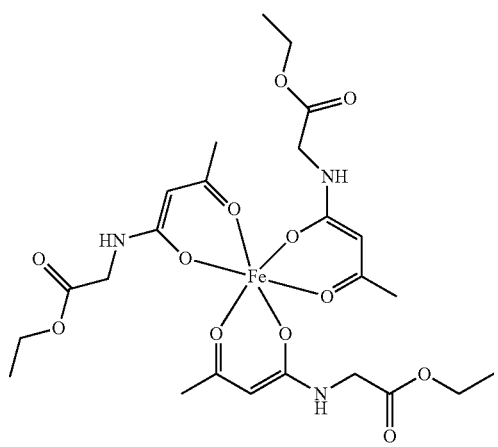

A solution of 0.50 g (3.08 mmol) iron(III) chloride (anhydrous) in 5 ml ethanol was added dropwise to a solution of 1.73 g (9.25 mmol) ethyl N-(3-oxobutanoyl)glycinate (or. (3-oxo-butyrylamino)ethyl acetate, respectively) in 20 ml ethanol. 1.56 g (18.50 mmol) sodium bicarbonate was then added in portions. After 2 hours of stirring at room temperature, the reaction mixture was filtrated off, washed with 10 ml EtOH, the filtrate spun off and the residue dried overnight in the drying cabinet at 50° C. 2.11 g of product was obtained as a brown oil.

IR (in substance, cm$^{-1}$): 3304, 2982, 2936, 1736, 1661, 1586, 1543, 1497, 1453, 1411, 1374, 1284, 1184, 1134, 1051, 1026.

Elemental analysis: C, 44.14; H, 6.11; N, 6.18.

Fe content 8.47% [m/m].

Example 21

Tris-(N,N-Dibutyl-3-oxopentanamide)-iron(III)-complex

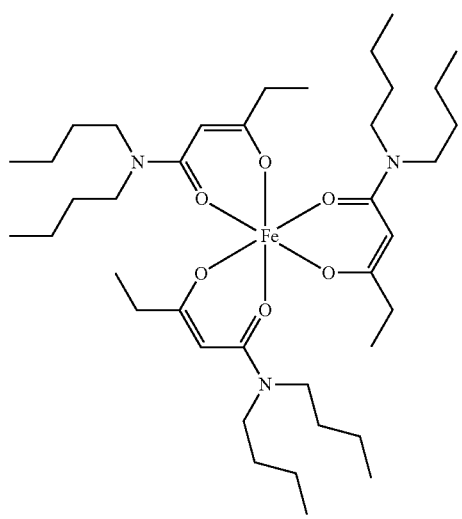

18 mmol (4.09 g) N,N-dibutyl-3-oxopentanamide were dissolved in 90 ml ethanol (anhydrous) and 6 mmol (0.811 g), FeCl$_3$ (anhydrous) was added. Then 5.93 ml sodium ethylate solution (21% m/m, about 18 mmol sodium ethylate) was added and it was stirred for 1 hour. The reaction mixture was filtered and the filtrate was concentrated on a rotary evaporator. The residue was dissolved in 120 ml dichloromethane, filtered again, the filtrate was evaporated and the product was dried in a vacuum oven at 50° C. This gave 4.0 g of the title compound.

IR (neat, cm$^{-1}$): 2957, 2931, 2872, 2359, 1721, 1634, 1596, 1556, 1513, 1491, 1461, 1429, 1393, 1366, 1316, 1291, 1254, 1225, 1190, 1155, 1112, 1079, 1062, 990, 926, 799, 767, 733, 711, 657.

CHN-Elemental analysis: C, 62.57; H, 9.64; N, 5.66.

Fe-content: 7.3% [m/m]

Example 22

Tris-(2-Fluoro-N,N-dimethyl-3-oxobutanamide)-iron(III)-complex

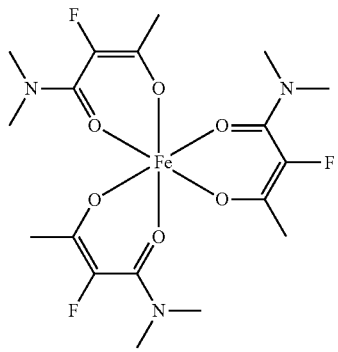

15 mmol (2.32 g) 2-fluoro-N,N-dimethyl-3-oxobutanamide were dissolved in 125 ml ethanol (anhydrous), and 4.86 ml sodium ethylate solution (21% m/m, about 15 mmol sodium ethoxide) were added. Then 5 mmol (0.811 g), FeCl$_3$ (anhydrous) was added and is was stirred for 2 h at 50° C. The reaction mixture was filtered after cooling, the filtrate was concentrated on a rotary evaporator and the product was dried in a vacuum oven at 50° C. This gave 2.5 g of the title compound.

IR (neat, cm$^{-1}$): 2937, 2361, 2341, 1737, 1656, 1573, 1477, 1419, 1402, 1361, 1332, 1259, 1209, 1145, 1051, 1020, 977, 894, 870, 736.

CHN-Elemental analysis: C, 38.59; H, 5.23; N, 7.15.

Fe-content: 9.96% [m/m]

Example 23

Tris-(2-Fluoro-3-oxo-N-propylbutanamide)-iron(III)-complex

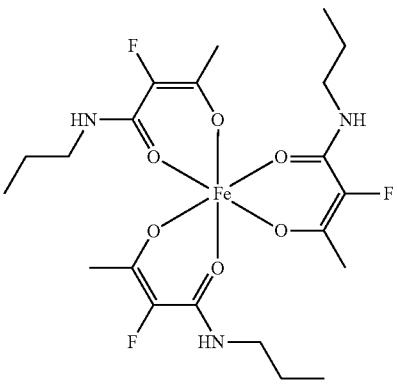

18 mmol (2.9 g) 2-fluoro-3-oxo-N-propylbutanamide and 6 mmol (0.972 g) FeCl$_3$ (anhydrous) were dissolved in 90 ml ethanol (anhydrous), and 2.78 ml sodium methylate solution (30% m/m, about 15 mmol sodium methoxide) were added. It was stirred for another 1 h, and the reaction solution was filtered. The filtrate was concentrated on a rotary evaporator and the product was dried in a vacuum oven at 50° C. This gave 3.14 g of the title compound.

IR (neat, cm$^{-1}$): 3306, 3090, 2966, 2936, 2876, 1736, 1674, 1602, 1549, 1522, 1459, 1438, 1382, 1275, 1246, 1160, 1114, 1088, 1050, 992, 958, 899, 821, 774, 744, 645.

CHN-Elemental analysis: C, 44.36; H, 6.08; N, 7.22.

Fe-content: 9.34% [m/m]

Example 24

Tris-(4-Methoxy-N,N-dimethyl-3-oxobutanamide)-iron(III)-complex

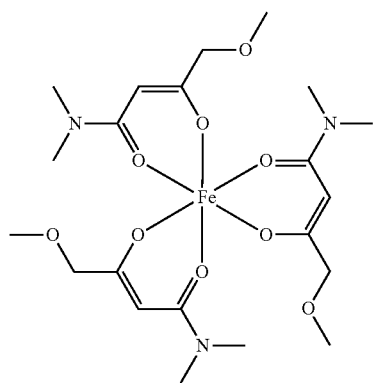

57 mmol (9.1 g) of 4-methoxy-N,N-dimethyl-3-oxobutanamide and 19 mmol (3.08 g) FeCl$_3$ (anhydrous) were dissolved in 260 ml ethanol (anhydrous), and 9.84 ml of sodium methoxide solution (30% m/m, about 53 mmol sodium methoxide) was added. It was stirred for another 1 h and the reaction solution was filtered. The filtrate was concentrated on a rotary evaporator and the product was dried in a vacuum oven at 50° C. This gave 10.5 g of the title compound.

IR (neat, cm$^{-1}$): 2930, 2822, 1730, 1603, 1568, 1497, 1424, 1402, 1368, 1331, 1260, 1200, 1174, 1109, 1059, 1023, 992, 959, 924, 862, 769, 736, 681.

CHN-Elemental analysis: C, 44.94; H, 6.66; N, 7.06.

Fe-content: 9.49% [m/m]

Example 25

Tris-(N,N,4-Trimethyl-3-oxopentanamide)-iron(III)-complex

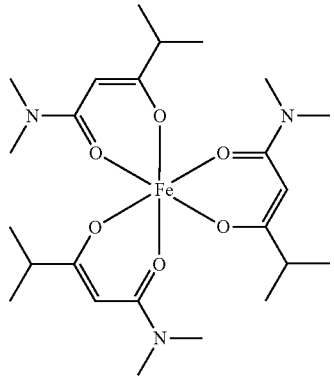

16 mmol (2.36 g) N,N,4-trimethyl-3-oxopentanamide and 5 mmol (0.811 g), FeCl$_3$ (anhydrous) were dissolved in 100 ml ethanol (anhydrous), and 2.78 ml sodium methoxide solution (30% m/m, about 15 mmol sodium methoxide) were added. It was stirred for another 1 h and the reaction solution was filtered. The filtrate was concentrated on a rotary evaporator and the product was dried in a vacuum oven at 50° C. This gave 2.6 g of the title compound.

IR (neat, cm$^{-1}$): 2958, 2927, 2868, 1720, 1593, 1556, 1526, 1502, 1487, 1402, 1378, 1359, 1311, 1260, 1198, 1176, 1157, 1083, 1006, 946, 891, 801, 773, 722, 678, 655.

CHN-Elemental analysis: C, 52.88; H, 7.91; N, 7.50.

Fe-content: 10.40% [m/m]

Example 26

Tris-(4-Methyl-1-(morpholin-4-yl)-pentane-1,3-dione)-iron(III)-complex

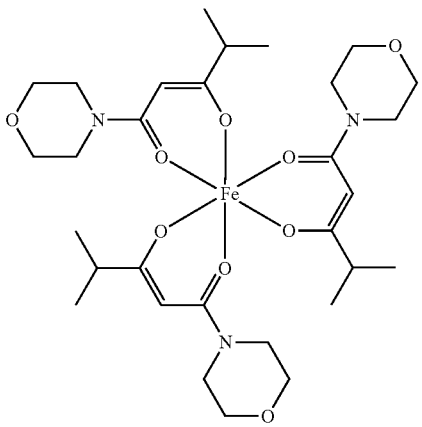

18 mmol (3.59 g) of 4-methyl-1-(morpholin-4-yl)pentane-1,3-dione and 6 mmol (0.973 g) FeCl$_3$ (anhydrous) were dissolved in 50 ml ethanol (anhydrous) and 3.00 ml sodium methylate solution (30% m/m, about 16 mmol sodium methylate) was added. It was stirred for another 1 h and the reaction solution was filtered. The filtrate was concentrated on a rotary evaporator and the product was dried in a vacuum oven at 50° C. This gave 4.0 g of the title compound.

IR (neat, cm$^{-1}$): 2964, 2924, 2857, 1714, 1678, 1640, 1549, 1516, 1478, 1459, 1439, 1384, 1371, 1357, 1313, 1300, 1273, 1244, 1189, 1159, 1114, 1087, 1065, 1018, 990, 947, 885, 851, 773, 717, 680.

CHN-Elemental analysis: C, 48.70; H, 6.84; N, 6.01.

Fe-content: 7.89% [m/m]

Example 27

Tris-(4-Methoxy-1-(morpholin-4-yl)butane-1,3-dione)-iron(III)-complex

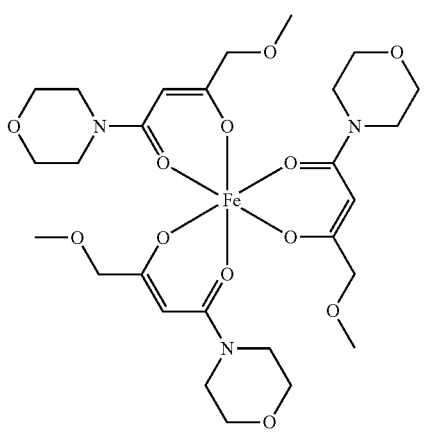

15 mmol (3.02 g) of 4-methoxy-1-(morpholin-4-yl)butane-1,3-dione and 5 mmol (0.811 g) FeCl$_3$ (anhydrous) were dissolved in 65 ml ethanol (anhydrous) and 2.59 ml sodium methylate solution (30% m/m, about 14 mmol sodium methylate) was added. It was stirred for another 1 h and the reaction solution was filtered. The filtrate was concentrated on a rotary evaporator and the product was dried in a vacuum oven at 50° C. This gave 3.66 g of the title compound.

IR (neat, cm$^{-1}$): 2969, 2897, 2856, 1732, 1640, 1597, 1563, 1514, 1441, 1383, 1301, 1273, 1246, 1197, 1110, 1065, 1017, 992, 961, 922, 863, 765, 730, 676.

CHN-Elemental analysis: C, 47.62; H, 6.90; N, 5.44.

Fe-content: 7.13% [m/m]

Example 28

Tris-(3-acetyl-1-methylpyrrolidin-2-one)-iron(III)-complex

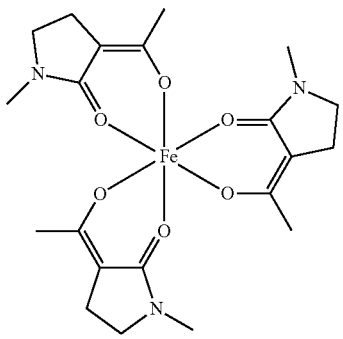

2.48 g (15.30 mmol) of iron(III)-chloride were dissolved in 700 ml of ethanol and 6.91 g (49.00 mmol) of 3-acetyl-1-methylpyrrolidine-2-one was added. 9.76 g 25% sodium methanolate solution (45.17 mmol) were diluted with 80 ml ethanol and added dropwise to the iron(III)-chloride solution. The reaction solution was stirred for 30 min and then filtered off. The filtrate was concentrated on a rotary evaporator to dryness and the residue is dried overnight at 50° C. under vacuum. This gave 7.4 g product as a violet powder.

IR (neat, cm$^{-1}$): 2915, 2866, 1677, 1601, 1553, 1497, 1476, 1443, 1401, 1365, 1344, 1267, 1182, 996, 964, 908, 746, 612.

Fe-content: 11.74% [m/m].

Example 29

Tris-(Ethyl (1-methyl-2-oxopyrrolidin-3-yl)(oxo) acetate)-iron(III)-complex

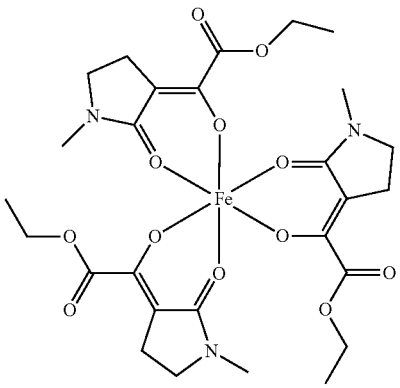

9.72 g of an iron ethoxide solution (2.22% Fe [m/m], 3.86 mmol) in ethanol were diluted in a nitrogen atmosphere with 40 ml of dry ethanol. 2.30 g (11.55 mmol) of ethyl (1-methyl-2-oxopyrrolidin-3-yl)(oxo)acetate were added to the solution and stirred at room temperature overnight. Then the solution was evaporated in a rotary evaporator to dryness and the residue dried at 50° C. overnight under vacuum. This gave 2.6 g product as a red solid.

IR (neat, cm$^{-1}$): 2933, 2896, 1719, 1704, 1607, 1500, 1477, 1455, 1407, 1395, 1367, 1350, 1303, 1270, 1207, 1170, 1107, 1031, 1008, 914, 869, 780, 743, 718, 633.

Elemental analysis: C, 47.90% H, 5.43% N, 6.11%.

Fe-content: 8.48% [m/m].

Example 30

Tris-(ethyl (1-methyl-2-oxopiperidin-3-yl)(oxo)acetate)-iron(III)-complex

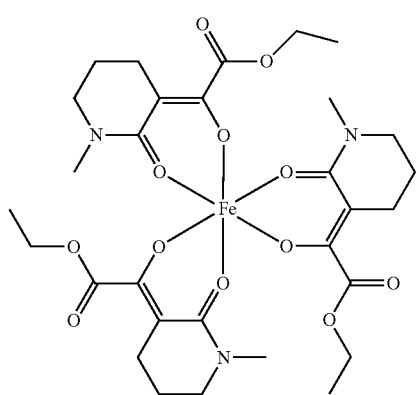

0.65 g (4.00 mmol) iron(III)-chloride were dissolved in 25 ml THF and 2.56 g (12.00 mmol) of ethyl (1-methyl-2-oxopiperidine-3-yl)(oxo)acetate were added. After 40 min stirring time 1.21 g (12.00 mmol) triethylamine was added and it was stirred for further 60 min at room temperature. Then 2.59 g 25% sodium methoxide solution (12.00 mmol) was added dropwise, and the solution was stirred for another 2 hours. The precipitated salt was filtered and the filtrate was concentrated on a rotary evaporator to dryness. The residue was dried for 1 day at 50° C. in a high vacuum. This gave 2.6 g product as a red solid.

IR (neat, cm$^{-1}$): 2939, 2863, 1724, 1610, 1573, 1538, 1480, 1402, 1364, 1308, 1256, 1219, 1195, 1101, 1079, 1060, 1016, 959, 920, 892, 858, 811, 764, 724, 692.

Elemental analysis: C, 51.62%, H, 6.23%, N, 5.90%.

Fe-content: 8.2% [m/m].

Example 31

Tris-(3-acetyl-1-methylpiperidin-2-one)-iron(III)-complex

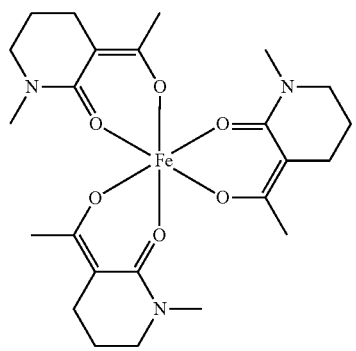

0.34 g (2.10 mmol) iron(III)chloride were dissolved in 100 ml of ethanol and 1.34 g (6.30 mmol) of 3-acetyl-1-methylpiperidin-2-one was added. 1.33 g 25% sodium methoxide solution (6.13 mmol) were diluted with 10 ml ethanol and added dropwise to the reaction solution. The reaction solution was stirred for 30 min and then filtered off. The filtrate was concentrated on a rotary evaporator to dryness and the residue was taken up in 50 ml of dichloromethane. The solution was again filtered, the dichloromethane was removed on a rotary evaporator and the residue was dried for 2 days at 50° C. under high vacuum. This gave 1.2 g product as a dark red solid.

IR (neat, cm$^{-1}$): 2927, 2855, 1559, 1462, 1399, 1303, 1254, 1202, 1181, 1082, 992, 921, 887, 856, 757, 707, 626.

Elemental analysis: C, 49.63%, H, 6.43%, N, 7.23%.

Fe-content: 9.80% [m/m].

Example 32

Tris-(ethyl 4-(dimethylamino)-2,4-dioxobutanoate)-iron(III)-complex

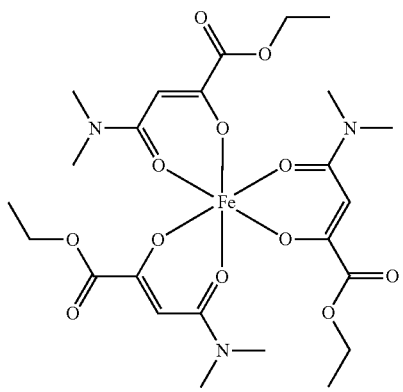

0.58 g (3.56 mmol) iron(III)chloride were dissolved in 80 ml THF and 2.00 g (10.69 mmol) of ethyl 4-(dimethylamino)-2,4-dioxobutanoate was added. After 40 min stirring time 1.07 g (10.69 mmol) triethylamine was added and the mixture was stirred for another 60 min at room temperature. Then 2.31 g 25% sodium methoxide solution (10.69 mmol) was added dropwise and the solution was stirred for another 2 hours. The precipitated salt was filtered and the filtrate was concentrated on a rotary evaporator to dryness. The residue was dried for 1 day at 50° C. in a high vacuum. This gave 2.0 g product as a red solid.

IR (neat, cm$^{-1}$): 2927, 1719, 1616, 1575, 1501, 1433, 1404, 1362, 1235, 1174, 1136, 1019, 944, 924, 767, 742, 652.

Elemental analysis: C, 45.83%, H, 5.82%, N, 6.83%.

Fe-content: 8.54% [m/m].

Example 33

Tris-(1-(morpholin-4-yl)butane-1,3-dione)-iron(III)-complex

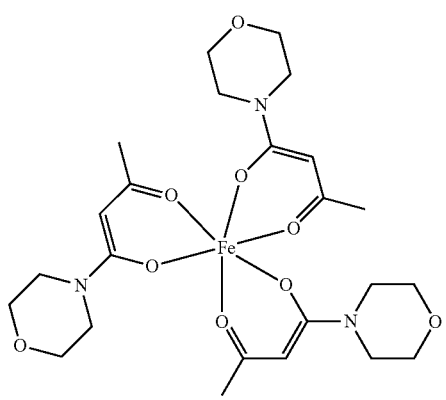

To a solution of 3.17 g (18.50 mmol) 1-(morpholin-4-yl)butane-1,3-dione in 40 ml of ethanol, a solution of 1.00 g (6.17 mmol) iron(III)chloride (anhydrous) in 10 ml ethanol was added dropwise. Then 6.22 g (74.00 mmol) of sodium bicarbonate was added in portions. After 1.5 h stirring at room temperature, the reaction mixture was filtered, washed with 10 ml of ethanol, the filtrate evaporated on a rotary evaporator, and the residue was dried overnight in an oven at 50° C. This gave 3.50 g of brown solid.

IR (neat, cm$^{-1}$): 2961, 2896, 2854, 1595, 1553, 1509, 1476, 1443, 1362, 1299, 1273, 1244, 1193, 1110.

Fe-content: 9.62% [m/m].

Example 34

Tris-(N-(2-methoxyethyl)-3-oxobutanamide)-iron(III)-complex

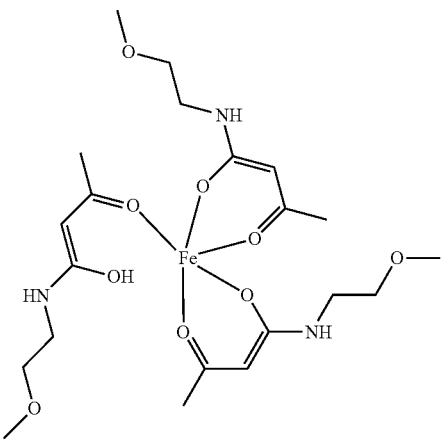

To a solution of 1.47 g (9.25 mmol) N-(2-methoxyethyl)-3-oxobutanamide in 15 ml of ethanol, a solution of 0.5 g (3.08 mmol) iron(III)chloride (anhydrous) in 5 ml of ethanol was added dropwise. Then 1.56 g (18.50 mmol) of sodium bicarbonate was added in portions. After stirring for 1 h at room temperature, the reaction mixture was filtered, washed with 10 ml of ethanol, the filtrate was evaporated on a rotary evaporator and the residue was dried overnight in an oven at 50° C. This gave 1.51 g of brown oil.

IR (neat, cm$^{-1}$): 3269, 2980, 2928, 2882, 2830, 1650, 1550, 1499, 1451, 1410, 1275, 1192, 1117, 1092, 1017, 958.

Fe-content: 9.68% [m/m].

Example 35

Tris-(N-Cyclopropyl-3-oxobutanamide)-iron(III)-complex

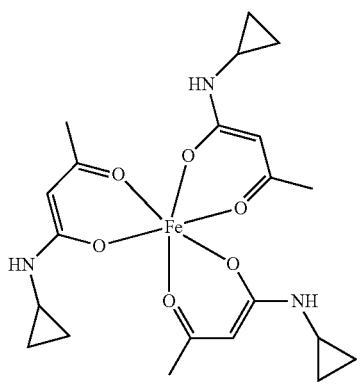

To a solution of 2.61 g (18.50 mmol) N-cyclopropyl-3-oxobutanamide in 30 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 1 h at room temperature, the reaction mixture was filtered, washed with 10 ml of ethanol, the filtrate was evaporated and the residue was dried overnight in an oven at 50° C. This gave 2.57 g of brown solid.

IR (neat, cm$^{-1}$): 3245, 3088, 3008, 1549, 1493, 1453, 1405, 1334, 1275, 1219, 1189, 1060, 1023, 981, 937.

Fe-content: 11.00% [m/m].

Example 36

Tris-(3-oxo-N-(propan-2-yl)butanamide)-iron(III)-complex

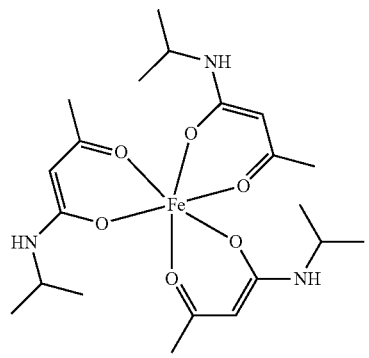

To a solution of 1.32 g (9.25 mmol) of 3-oxo-N-(propan-2-yl)butanamide in 15 ml of ethanol, a solution of 0.5 g (3.08 mmol) iron(III)chloride (anhydrous) in 5 ml ethanol was added dropwise. Then 1.56 g (18.50 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 1.30 g of a brown solid.

IR (neat, cm$^{-1}$): 3248, 3101, 2972, 2936, 2873, 1544, 1492, 1468, 1447, 1365, 1321, 1265, 1187, 1171, 1129, 998, 968.

Fe-content: 11.22% [m/m].

Example 37

Tris-(N-(2-hydroxyethyl)-3-oxobutanamide)-iron(III)-complex

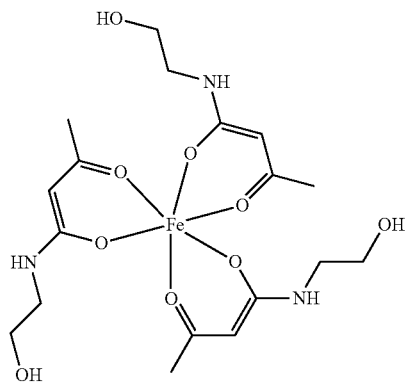

To a solution of 2.69 g (18.50 mmol) N-(2-hydroxyethyl)-3-oxobutanamide in 40 ml of ethanol, a solution of 1.00 g (6.17 mmol) iron(III)chloride (anhydrous) in 10 ml ethanol was added dropwise. Then 6.22 g (74.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 2.72 g of a brown solid.

IR (neat, cm$^{-1}$): 3259, 3110, 2946, 2875, 1552, 1498, 1451, 1405, 1360, 1273, 1188, 1059, 1018, 955, 778.

Fe-content: 11.30% [m/m].

Example 38

Tris-(N-(3-hydroxypropyl)-3-oxobutanamide)-iron(III)-complex

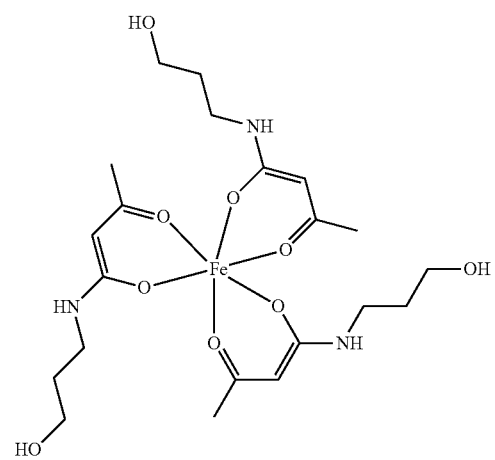

To a solution of 1.47 g (9.25 mmol) N-(3-hydroxypropyl)-3-oxobutanamide in 20 ml of ethanol, a solution of 0.5 g (3.08 mmol) iron(III)chloride (anhydrous) in 5 ml of ethanol was added dropwise. Then 1.56 g (18.50 mmol) of sodium bicarbonate was added in portions. After stirring for 2 h at room temperature, the reaction mixture was filtered, washed with 10 ml of ethanol, the filtrate was evaporated and the residue dried overnight in an oven at 50° C. This gave 1.80 g of brown solid.

IR (neat, cm$^{-1}$): 3270, 2939, 1551, 1500, 1407, 1270, 1188, 1008, 973, 947, 777.

Fe-content: 10.05% [m/m].

Example 39

Tris-(N-(4-hydroxybutyl)-3-oxobutanamide)-iron (III)-complex

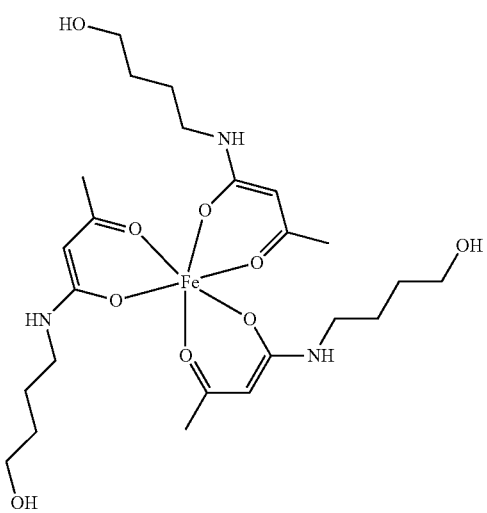

To a solution of 2.94 g (18.50 mmol) N-(4-hydroxybutyl)-3-oxobutanamide in 40 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 2 h at room temperature, the reaction mixture was filtered, washed with 10 ml of ethanol, the filtrate was evaporated and the residue dried overnight in an oven at 50° C. This gave 2.72 g of a brown solid.

IR (neat, cm$^{-1}$): 3273, 2934, 2867, 1649, 1555, 1502, 1436, 1409, 1272, 1188, 1053, 1027, 946, 778.

Fe-content: 9.36% [m/m].

Example 40

Tris-(N-(5-hydroxypentyl)-3-oxobutanamide)-iron (III)-complex

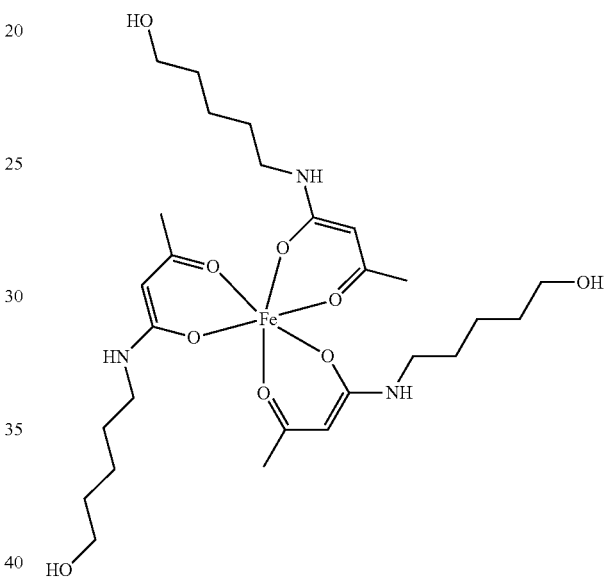

To a solution of 3.46 g (18.50 mmol) N-(5-hydroxypentyl)-3-oxobutanamide in 40 ml of ethanol, a solution of 1.00 g (6.17 mmol) iron(III)chloride (anhydrous)) in 10 ml ethanol was added dropwise. Then 3.11 g (37.00 mmol) of sodium bicarbonate was added in portions. After stirring for 1 h at room temperature, the reaction mixture was filtered, washed with 10 ml of ethanol, the filtrate was evaporated and the residue was dried overnight in an oven at 50° C. This gave 3.51 g of brown solid.

IR (neat, cm$^{-1}$): 3255, 3109, 2932, 2862, 1558, 1500, 1433, 1407, 1274, 1187, 1021, 949, 779.

Fe-content: 8.85% [m/m].

Example 41

Tris-(N-(1-hydroxy-2-methylpropan-2-yl)-3-oxobutanamide)-iron(III)-complex

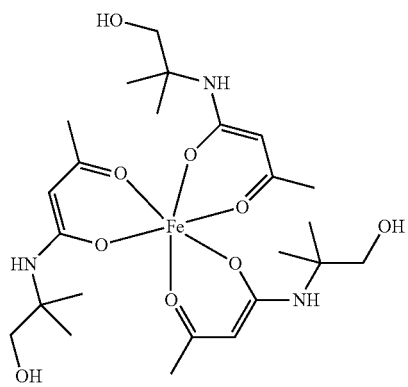

To a solution of 3.20 g (18.50 mmol) N-(1-hydroxy-2-methylpropane-2-yl)-3-oxobutanamid in 40 ml of ethanol, a solution of 1.00 g (6.17 mmol) iron (III) chloride anhydrous was added dropwise in 10 ml ethanol. Then 3.11 g (37.00 mmol) of sodium bicarbonate was added in portions. After stirring for 1 h at room temperature, the reaction mixture was filtered, washed with 10 ml of ethanol, the filtrate evaporated and the residue dried overnight in an oven at 50° C. This gave 3.42 g of a brown solid.

IR (neat, cm$^{-1}$): 3286, 2972, 2927, 1593, 1550, 1498, 1446, 1411, 1363, 1287, 1225, 1189, 1050, 962.

Fe-content: 9.17% [m/m].

Example 42

Tris-(N-(2-hydroxyethyl)-N-methyl-3-oxobutanamide)-iron(III)-complex

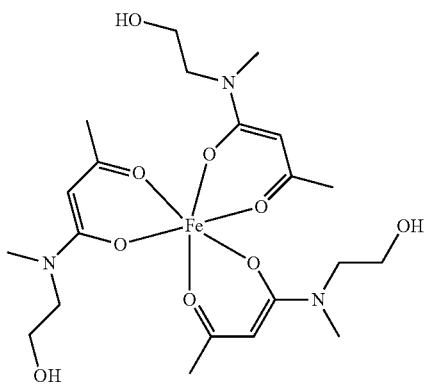

To a solution of 2.94 g (18.50 mmol) N-(2-hydroxyethyl)-N-methyl-3-oxobutanamide in 30 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 1 h at room temperature, the reaction mixture was filtered, washed with 10 ml of ethanol, the filtrate was evaporated and the residue was dried overnight in an oven at 50° C. This gave 3.11 g of a brown solid.

IR (neat, cm$^{-1}$): 3371, 2975, 2930, 2884, 1638, 1561, 1517, 1494, 1436, 1351, 1301, 1205, 1170, 1051, 958.

Fe-content: 9.61% [m/m].

Example 43

Tris-(N-(2-hydroxypropyl)-3-oxobutanamide)-iron(III)-complex

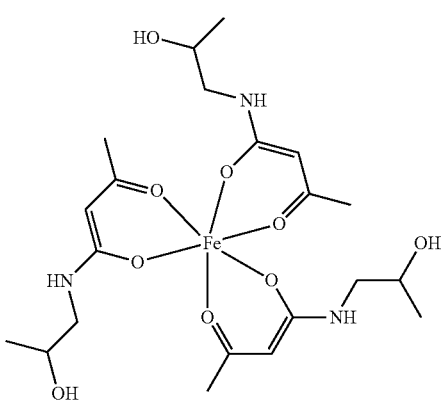

To a solution of 2.94 g (18.50 mmol) N-(2-hydroxypropyl)-3-oxobutanamide in 30 ml of ethanol, a solution of 1.00 g (6.17 mmol) iron(III)chloride (anhydrous) in 10 ml ethanol was added dropwise. Then 6.22 g (74.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.11 g of a brown solid.

IR (neat, cm$^{-1}$): 3281, 2973, 2925, 1552, 1501, 1454, 1409, 1377, 1272, 1190, 1079, 1053, 951, 777.

Fe-content: 9.84% [m/m].

Example 44

Tris-(N-(1-hydroxypropan-2-yl)-3-oxobutanamide)-iron(III)-complex

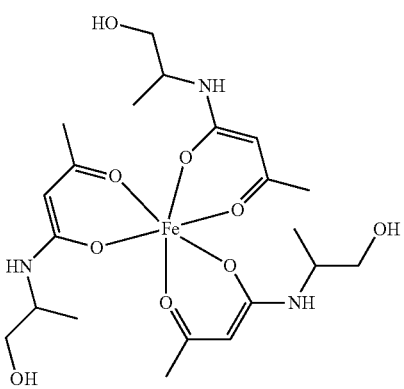

To a solution of 2.94 g (18.50 mmol) N-(2-hydroxypropyl)-3-oxobutanamide in 30 ml of ethanol, a solution of 1.00 g (6.17 mmol) iron(III)chloride (anhydrous) in 10 ml ethanol was added dropwise. Then 6.22 g (74.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.22 g of a brown solid.

IR (neat, cm$^{-1}$): 3259, 2973, 1551, 1494, 1451, 1409, 1270, 1189, 1158, 1091, 1041, 962.

Fe-content: 9.57% [m/m].

Example 45

Tris-(N-(1-hydroxybutan-2-yl)-3-oxobutanamide)-iron(III)-complex

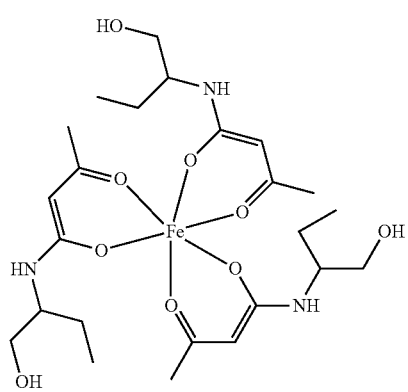

To a solution of 3.21 g (18.50 mmol) N-(1-hydroxybutane-2-yl)-3-oxobutanamide in 30 ml of ethanol a solution of 1.00 g (6.17 mmol) iron(III)chloride (anhydrous) in 10 ml ethanol was added dropwise. Then 6.22 g (74.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.22 g of brown solid.

IR (neat, cm$^{-1}$): 3268, 2965, 2933, 2875, 1546, 1493, 1457, 1410, 1285, 1188, 1049, 1000, 959, 775.

Fe-content: 9.39% [m/m].

Example 46

Tris-(N-(2,3-dihydroxypropyl)-3-oxobutanamide)-iron(III)-complex

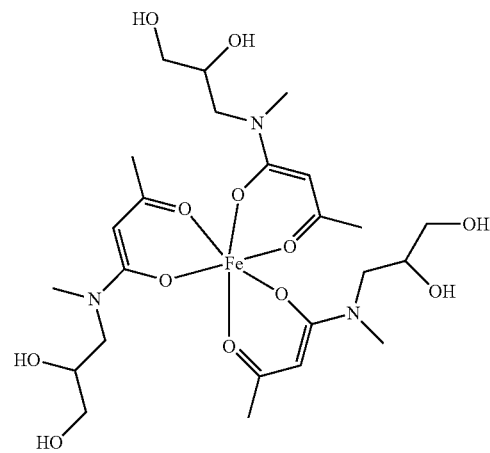

To a solution of 1.75 g (9.25 mmol) N-(2,3-dihydroxypropyl)-3-oxobutanamide in 20 ml of ethanol, a solution of 0.5 g (3.08 mmol) iron(III)chloride (anhydrous) in 5 ml ethanol was added dropwise. Then 1.56 g (18.50 mmol) of sodium bicarbonate was added in portions. After stirring for 1 h at room temperature, the reaction mixture was filtered, washed with 10 ml of ethanol, the filtrate was evaporated and the residue was dried overnight in an oven at 50° C. This gave 1.80 g of a brown solid.

IR (neat, cm$^{-1}$): 3349, 2929, 1635, 15559, 1519, 1493, 1353, 1210, 1157, 1099, 1044, 996, 956, 765.

Fe-content: 8.81% [m/m].

Example 47

Tris-(1-(3-hydroxypiperidin-1-yl)butane-1,3-dione)-iron(III)-complex

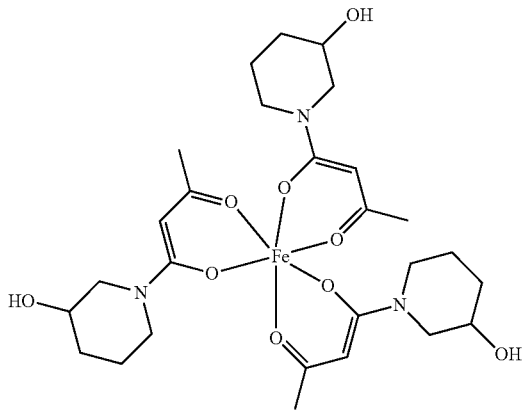

To a solution of 3.43 g (18.50 mmol) 1-(3-hydroxypiperidine-1-yl)butane-1,3-dione in 50 ml of ethanol, a solution of 1.00 g (6.17 mmol) iron(III)chloride (anhydrous) in 10 ml ethanol was added dropwise. Then 1.56 g (18.50 mmol) of sodium bicarbonate was added in portions. After stirring for 4 h at room temperature, the reaction mixture was filtered, washed with 10 ml of ethanol, the filtrate was evaporated and the residue was dried overnight in an oven at 50° C. This gave 3.51 g of a brown solid.

IR (neat, cm$^{-1}$): 3290, 2929, 2859, 1554, 1509, 1483, 1441, 1363, 1254, 1228, 1206, 1143, 1072, 997, 953, 858, 760.

Fe-content: 8.73% [m/m].

Example 48

Tris-(1-[4-(hydroxymethyl)piperidin-1-yl]butane-1,3-dione)-iron(III)-complex

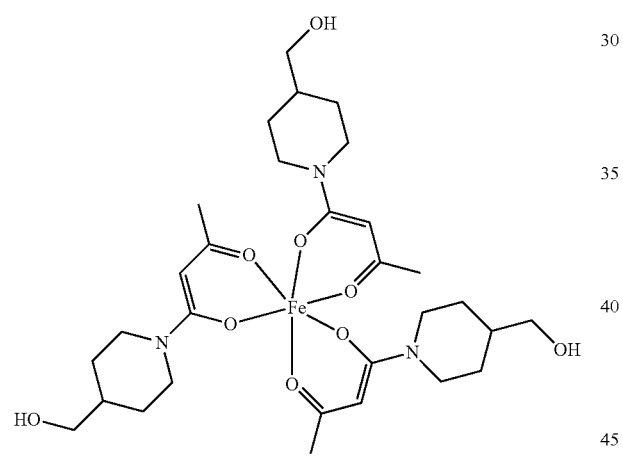

To a solution of 3.68 g (18.50 mmol) of 1-[4-(hydroxymethyl)piperidine-1-yl]butane-1,3-dione in 50 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.81 g of a brown solid.

IR (neat, cm$^{-1}$): 3334, 2916, 2858, 1555, 1511, 1485, 1445, 1366, 1268, 1247, 1217, 1088, 1033, 979, 953, 760.

Fe-content: 8.39% [m/m].

Example 49

Tris-(1-[3-(hydroxymethyl)piperidin-1-yl]butane-1,3-dione)-iron(III)-complex

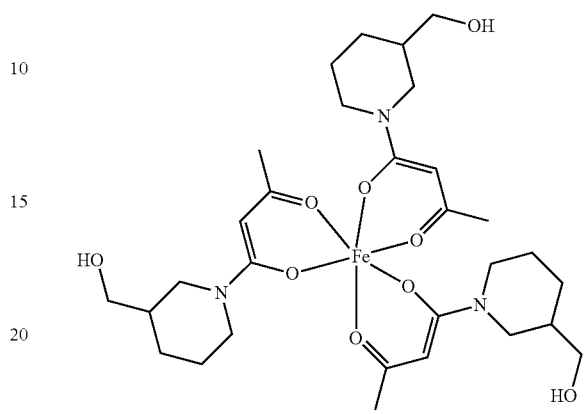

To a solution of 3.68 g (18.50 mmol) of 1-[3-(hydroxymethyl)piperidine-1-yl]butane-1,3-dione in 50 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 1 h at room temperature, the reaction mixture was filtered, washed with 10 ml of ethanol, the filtrate was evaporated and the residue was dried overnight in an oven at 50° C. This gave 3.92 g of a brown solid.

IR (neat, cm$^{-1}$): 3350, 2922, 2858, 1555, 1510, 1485, 1440, 1366, 1259, 1088, 1039, 995, 953, 760.

Fe-content: 8.27% [m/m].

Example 50

Tris-(1-[2-(hydroxymethyl)piperidin-1-yl]butane-1,3-dione)-iron(III)-complex

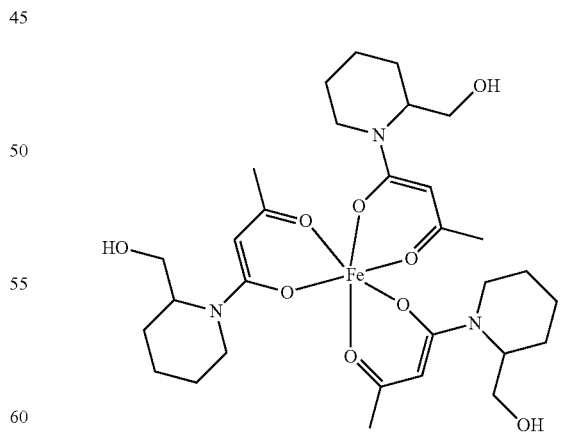

To a solution of 3.68 g (18.50 mmol) of 1-[2-(hydroxymethyl)piperidine-1-yl]butane-1,3-dione in 50 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After

Example 51

Tris-(1-[(3S)-3-hydroxypyrrolidin-1-yl]butane-1,3-dione)-iron(III)-complex

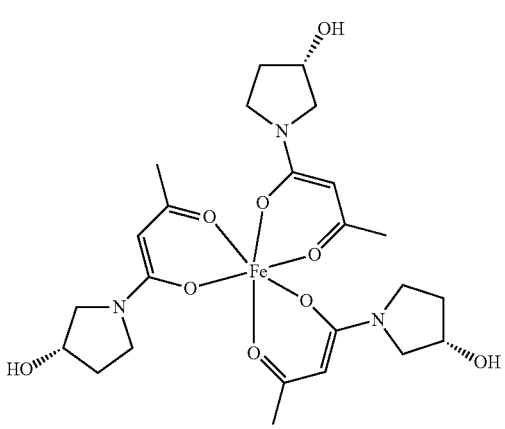

To a solution of 3.17 g (18.50 mmol) of 1-[(3S)-3-hydroxypyrrolidine-1-yl]butane-1,3-dione in 50 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.23 g of a brown solid.

IR (neat, cm$^{-1}$): 3315, 2946, 1558, 1514, 1472, 1350, 1206, 1103, 1054, 951, 875, 763.

Fe-content: 8.61% [m/m].

Example 52

Tris-(1-[4-(2-hydroxyethyl)piperazin-1-yl]butane-1,3-dione)-iron(III)-complex

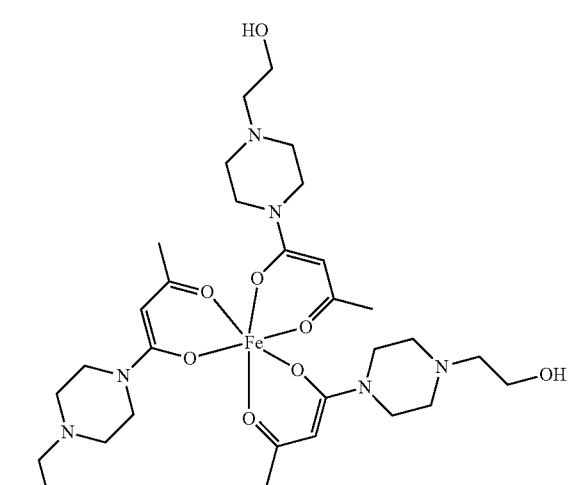

To a solution of 3.96 g (18.50 mmol) of 1-[4-(2-hydroxyethyl)piperazine-1-yl]butane-1,3-dione in 80 ml of MeOH a solution of 1.00 g (6.17 mmol) iron(III)chloride (anhydrous) in 20 ml MeOH was added dropwise. Then 3.11 g (37.00 mmol) of sodium bicarbonate was added in portions. After stirring for 2 h at room temperature, the reaction mixture was evaporated, the residue taken up in 100 ml dichloromethane, stirred for 15 minutes, filtered, and the filtrate was evaporated. The residue was taken up in 50 ml EtOH, evaporated again and the resulting residue was dried over eight in the drying oven. This gave 4.10 g of a brown solid.

IR (neat, cm$^{-1}$): 3365, 2914, 2809, 1591, 1554, 1509, 1480, 1443, 1369, 1290, 1249, 1138, 1050, 983, 960, 876, 759, 673.

Fe-content: 7.89% [m/m].

--- stirring for 2 h at room temperature, the reaction mixture was filtered, washed with 10 ml of ethanol, the filtrate was evaporated and the residue was dried overnight in an oven at 50° C. This gave 3.88 g of a brown solid.

IR (neat, cm$^{-1}$): 3358, 2914, 2854, 1554, 1509, 1484, 1445, 1370, 1311, 1269, 1245, 1217, 1088, 1035, 978, 953, 759.

Fe-content: 8.37% [m/m].

Example 53

Tris-(1-(4-methylpiperazin-1-yl)butane-1,3-dione)-iron(III)-complex

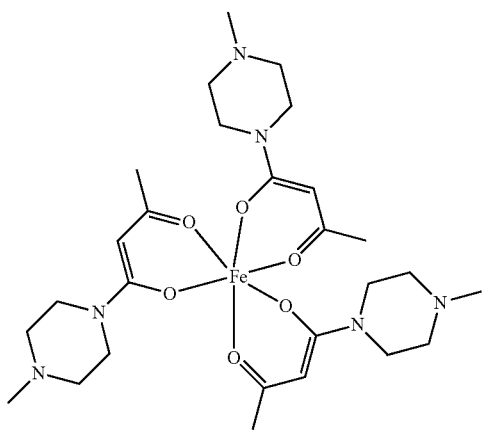

To a solution of 3.41 g (18.50 mmol) 1-(4-methyl-1-yl) butane-1,3-dione in 80 ml MeOH, a solution of 1.00 g (6.17 mmol) iron(III)chloride (anhydrous) in 20 ml MeOH was added dropwise. Then 3.11 g (37.00 mmol) of sodium bicarbonate was added in portions. After stirring for 2 h at room temperature, the reaction mixture was evaporated, the residue taken up in 100 ml dichloromethane, stirred for 15 minutes, filtered, and the filtrate was evaporated. The residue was taken up in 50 ml EtOH, evaporated again and the resulting residue was dried over eight in the drying oven. This gave 3.52 g of a brown solid.

IR (neat, cm$^{-1}$): 2934, 2845, 2789, 1554, 1507, 1478, 1445, 1370, 1291, 1257, 1235, 1142, 1092, 1072, 1000, 981, 959. 757.

Fe-content: 8.77% [m/m].

Example 54

Tris-(N-(3-hydroxypropyl)-N-methyl-3-oxobutanamide)-iron(III)-complex

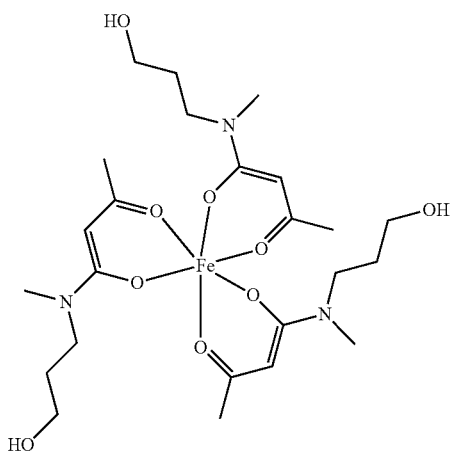

To a solution of 3.20 g (18.50 mmol) N-(3-hydroxypropyl)-N-methyl-3-oxobutanamide in 40 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 1 h at room temperature, the reaction mixture was filtered, washed with 10 ml of ethanol, the filtrate was evaporated and the residue was dried overnight in a drying oven at 50° C. This gave 3.31 g of a brown oil.

IR (neat, cm$^{-1}$): 3376, 2919, 1557, 1492, 1348, 1296, 1263, 1212, 1190, 1051, 989, 955, 763.

Fe-content: 9.08% [m/m].

Example 55

Tris-(N-(trans-4-hydroxycyclohexyl)-3-oxobutanamide)-iron(III)-complex

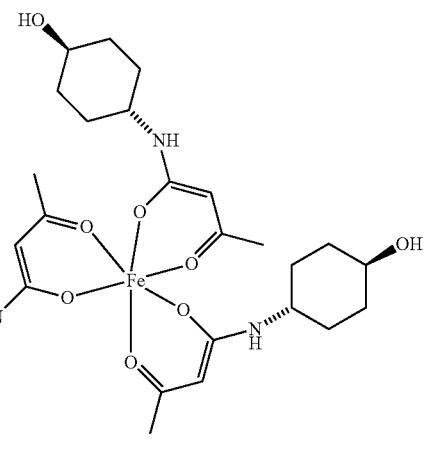

To a solution of 3.68 g (18.50 mmol) N-(trans-4-hydroxycyclohexyl)-3-oxobutanamide in 80 ml of ethanol, a solution of 1.00 g (6.17 mmol) iron(III)chloride (anhydrous) in 20 ml ethanol was added dropwise. Then 6.22 g (74.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.81 g of a brown solid.

IR (neat, cm$^{-1}$): 3280, 2932, 2859, 1549, 1494, 1453, 1409, 1371, 1309, 1265, 1187, 1055, 1014, 961, 941, 776.

Fe-content: 7.84% [m/m].

Example 56

Tris-(N-(3-hydroxy-2,2-dimethylpropyl)-3-oxobutanamide)-iron(III)-complex

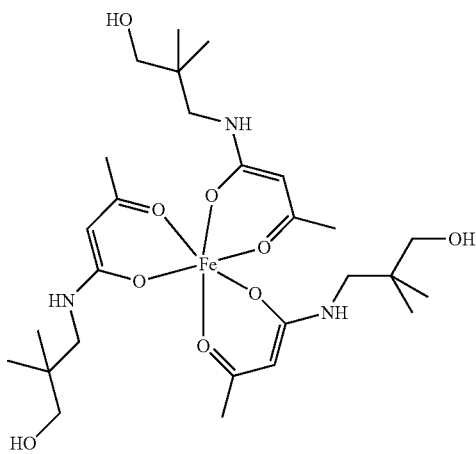

To a solution of 3.46 g (18.50 mmol) N-(3-hydroxy-2,2-dimethylpropyl)-3-oxobutanamide in 50 ml of ethanol, a solution of 1.00 g (6.17 mmol) of iron(111)chloride (anhydrous) in 15 ml ethanol was added dropwise. Then 6.22 g (74.00 mmol) of sodium bicarbonate was added in portions. After stirring for 4 h at room temperature, the reaction mixture was filtered, washed with 10 ml of ethanol, the filtrate was evaporated and the residue was dried overnight in an oven at 50° C. This gave 4.40 g of a brown solid.

IR (neat, cm$^{-1}$): 3289, 2963, 2872, 1554, 1502, 1450, 1410, 1265, 1190, 1050, 1014, 948, 777.

Fe-content: 8.3% [m/m].

Example 57

Tris-(1-[4-(dimethylamino)piperidin-1-yl]butane-1,3-dione)-iron(III)-complex

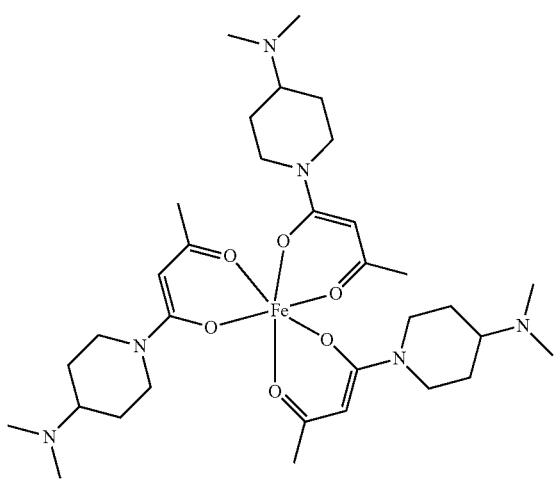

To a solution of 3.93 g (18.50 mmol) of 1-[4-(dimethylamino)piperidin-1-yl]butane-1,3-dione in 80 ml MeOH, a solution of 1.00 g (6.17 mmol) of iron(III)chloride (anhydrous) in 10 ml MeOH was added dropwise. Then 3.11 g (37.00 mmol) of sodium bicarbonate was added in portions. After stirring for 2 h at room temperature, the reaction mixture was evaporated, the residue was taken up in 100 ml dichloromethane, stirred for 15 minutes, filtered, and the filtrate was evaporated. The residue was taken up in 50 ml EtOH, evaporated again and the resulting residue was dried overnight in the oven. This gave 4.23 g of a brown solid.

IR (neat, cm$^{-1}$): 2940, 2858, 2769, 1593, 1553, 1509, 1482, 1448, 1372, 1328, 1271, 1236, 1205, 1040, 957, 874, 758.

Fe-content: 7.97% [m/m].

Example 58

Tris-(1-(4-methoxypiperidin-1-yl]butane-1,3-dione)-iron(III)-complex

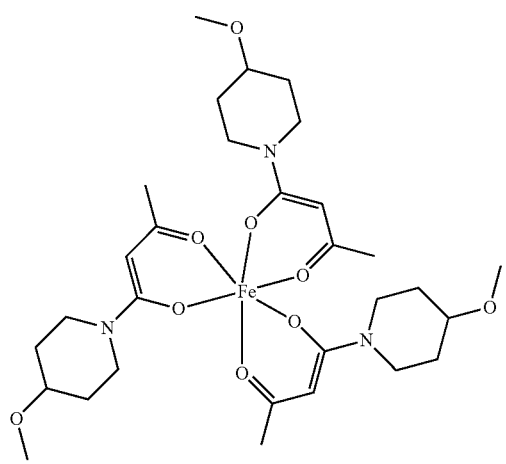

To a solution of 3.69 g (18.50 mmol) 1-(4-methoxypiperidin-1-yl]butane-1,3-dione in 80 ml MeOH, a solution of 1.00 g (6.17 mmol) iron(III)chloride (anhydrous) in 10 ml MeOH was added dropwise. Then, 3.11 g (37.00 mmol) of sodium bicarbonate was added in portions. After 1 h stirring at room temperature, the reaction mixture was evaporated, the residue was taken up in 100 ml dichloromethane, 15 min stirred, filtered, and the filtrate was evaporated. The residue was taken up in 50 ml EtOH, evaporated again, and the resulting residue was dried overnight in a drying oven. This gave 4.01 g of a brown solid.

IR (neat, cm$^{-1}$): 2944, 2825, 1634, 1557, 1511, 1452, 1376, 1317, 1271, 1235, 1184, 1096, 1047, 1023, 959, 939, 759.

Fe-content: 8.42% [m/m].

Example 59

Tris-(1-(2,6-dimethylmorpholin-4-yl]butane-1,3-dione)-iron(III)-complex

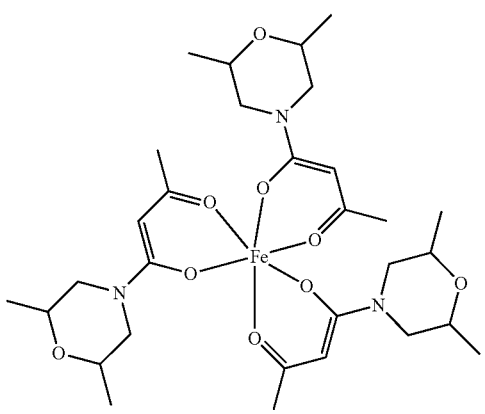

To a solution of 3.69 g (18.50 mmol) 1-(2,6-dimethylmorpholine-4-yl]butane-1,3-dione in 40 ml of ethanol, a solution of 1.00 g (6.17 mmol) iron(III)chloride (anhydrous) in 10 ml ethanol was added dropwise. Then, 3.11 g (37.00 mmol) of sodium bicarbonate was added in portions. After stirring for 2 h at room temperature, the reaction mixture was filtered, washed with 10 ml of ethanol, the filtrate was evaporated and the residue overnight was dried in an oven at 50° C. This gave 3.92 g of a brown solid.

IR (neat, cm$^{-1}$): 2974, 2872, 1556, 1510, 1477, 1373, 1258, 1244, 1172, 1138, 1116, 1082, 1050, 1002, 958, 759.

Fe-content: 8.10% [m/m].

Example 60

Tris-(N-(morpholin-4-yl)-3-oxobutanamide)-iron(III)-complex

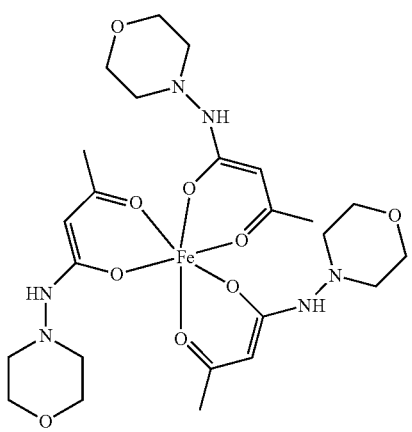

To a solution of 3.44 g (18.50 mmol) N-(morpholine-4-yl)-3-oxobutanamide in 50 ml of ethanol, a solution of 1.00 g (6.17 mmol) iron(III)chloride (anhydrous) in 20 ml ethanol was added dropwise. Then 3.11 g (37.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.63 g of a brown solid.

IR (neat, cm$^{-1}$): 3209, 2854, 1569, 1518, 1430, 1366, 1335, 1265, 1204, 1108, 1072, 1044, 975, 952, 869, 778, 703.

Fe-content: 8.34% [m/m].

Example 61

Tris-(1-(4-hydroxypiperidin-1-yl)pentane-1,3-dione)-iron(III)-complex

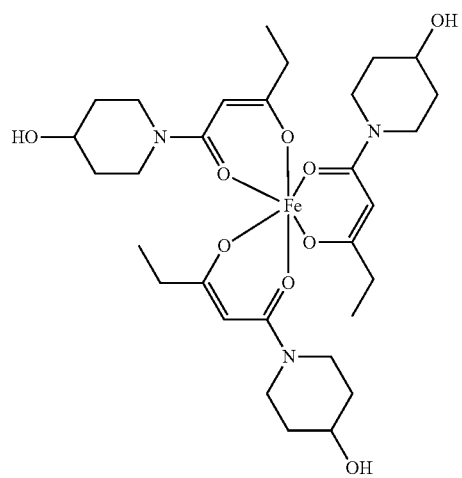

For the solution of 5.54 g (27.8 mmol) 1-(4-hydroxypiperidine-1-yl)pentane-1,3-dione in 45 ml of anhydrous ethanol, a solution of 1.51 g (9.31 mmol) anhydrous iron(III) chloride in 10 ml of anhydrous ethanol was added, followed by 4.67 g (55.6 mmol) of sodium bicarbonate. After 6.5 h, the reaction mixture was filtered and the solids discarded. The filtrate was freed from solvent on a rotary evaporator and the residue was dried for 16 h in a vacuum oven. This gave 5.56 g of a brown-red solid.

IR (neat, cm$^{-1}$): 2932, 2870, 1588, 1551, 1509, 1444, 1382, 1366, 1314, 1265, 1224, 1119, 1074, 978, 924, 832, 801, 764, 705, 661.

Fe-content: 8.26%

Example 62

Tris-(1-(morpholin-4-yl)pentane-1,3-dione)-iron(III)-complex

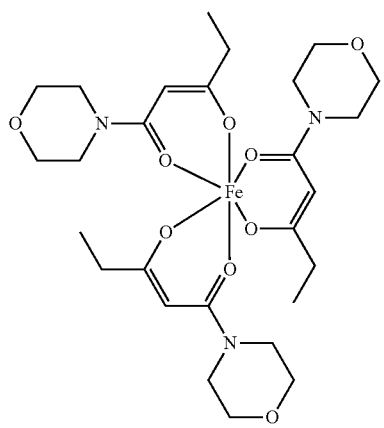

To a solution of 3.18 g (17.2 mmol) 1-(morpholine-4-yl)pentane-1,3-dione in anhydrous ethanol, a solution of 0.997 g (6.15 mmol) of anhydrous iron(III)chloride in 11 ml of anhydrous ethanol was added. Then, 3.11 g (37.0 mmol) sodium hydrogen carbonate was added and the reaction mixture was stirred 4 hours. The solids were filtered off and discarded. The filtrate was evaporated in a rotary evaporator to dryness and the residue was dried for 16 h in a vacuum oven. This gave 3.33 g of a red-brown solid.

IR (neat, cm$^{-1}$): 2964, 2851, 1591, 1551, 1510, 1473, 1439, 1380, 1315, 1300, 1274, 1241, 1189, 1112, 1063, 1003, 929, 857, 801, 763, 706, 664, 593.

Fe-content: 9.13% [m/m/].

Example 63

Tris-(N-Butyl-3-oxoheptanamide)-iron(III)-complex

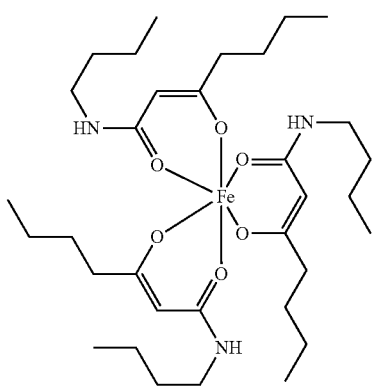

60 mmol (11.96 g) N-butyl-3-oxoheptanamide and 20 mmol (3.24 g) FeCl$_3$ (anhydrous) were dissolved in 110 ml ethanol (anhydrous), and 10.4 ml sodium methylate solution (30% m/m) added. It was stirred for 0.5 hours and the reaction solution was filtered. The filtrate was concentrated on a rotary evaporator and the product was dried. This gave 13.7 g of the title compound.

IR (neat, cm$^{-1}$): 2956, 2930, 2871, 1717, 1656, 1558, 1500, 1435, 1376, 1325, 1299, 1271, 1177, 1103, 1085, 1050, 994, 948, 894, 778, 682.

CHN-Elemental analysis: C, 59.26; H, 9.21; N, 6.12.

Fe-content: 7.39% [m/m]

Example 64

Tris-(1-(4-Hydroxypiperidin-1-yl)-4-methylpentane-1,3-dione)-iron(III)-complex

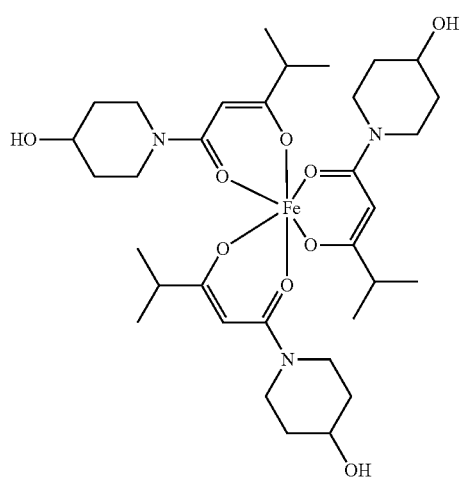

90 mmol (19.2 g) 1-(4-hydroxypiperidine-1-yl)-4-methylpentane-1,3-dione and 30 mmol (4.87 g) FeCl$_3$ (anhydrous) were dissolved in 150 ml ethanol (anhydrous) and 30 ml sodium ethylate solution (21% m/m) was added. It was stirred for 0.5 h and the reaction solution was filtered. The filtrate was concentrated on a rotary evaporator and the product was dried in a vacuum oven at 50° C. This gave 19.8 g of the title compound.

IR (neat, cm$^{-1}$): 2927, 2866, 1550, 1513, 1443, 1372, 1312, 1265, 1225, 1190, 1157, 1119, 1072, 1022, 980, 945, 882, 823, 808, 771, 714, 660, 646.

CHN-Elemental analysis: C, 52.00; H, 7.79; N, 5.99.

Fe-content: 7.21% [m/m]

Example 65

Tris-(N-(2-Hydroxyethyl)-N,4-dimethyl-3-oxopentanamide)-iron(III)-complex

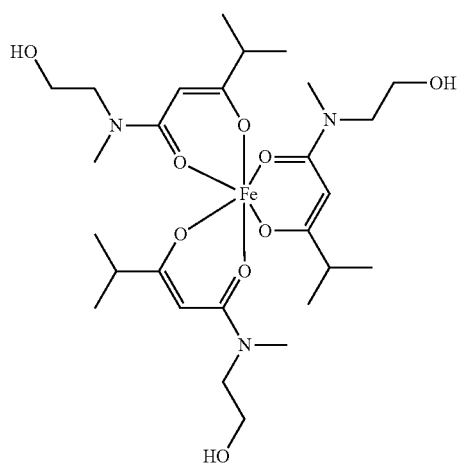

90 mmol (17.93 g) N-(2-hydroxyethyl)-N,4-dimethyl-3-oxopentanamide and 30 mmol (4.87 g), FeCl₃ (anhydrous) were dissolved in 150 ml ethanol (anhydrous) and 15 ml sodium methylate solution (30% m/m) was added. It was stirred for another 0.5 h and the reaction solution was filtered. The filtrate was concentrated on a rotary evaporator and the product was dried in a vacuum oven at 50° C. This gave 20.7 g of the title compound.

IR (neat, cm$^{-1}$): 2966, 2926, 2859, 1714, 1627, 1550, 1517, 1479, 1460, 1439, 1384, 1371, 1358, 1301, 1273, 1246, 1190, 1159, 1114, 1087, 1065, 1051, 1019, 991, 947, 927, 884, 850, 774, 717, 682.

CHN-Elemental analysis: C, 44.04; H, 6.97; N, 6.33.
Fe-content: 7.79% [m/m]

Example 66

Tris-(N,N-Dimethyl-2-oxocyclopentanecarboxamide)-iron(III)-complex

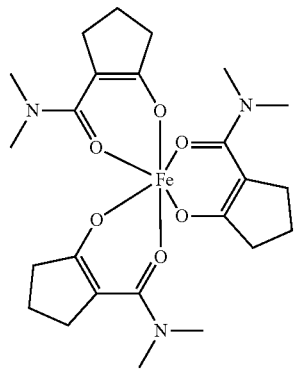

18 mmol (3.29 g) N,N-dimethyl-2-oxocyclopentanecarboxamide (purity >85%) and 6 mmol (0.925 g) FeCl₃ (anhydrous) were dissolved in 50 ml ethanol (anhydrous), and 3 ml sodium methylate solution (30% m/m) were added. It was stirred for 1 h and the reaction solution was filtered. The filtrate was concentrated on a rotary evaporator and the product was dried in a vacuum oven at 50° C. This gave 3.9 g of the title compound.

IR (neat, cm$^{-1}$): 2945, 2882, 1735, 1635, 1555, 1491, 1466, 1451, 1411, 1395, 1362, 1347, 1303, 1262, 1215, 1186, 1169, 1141, 1099, 1050, 1020, 983, 946, 915, 903, 885, 834, 770, 754, 733, 694, 638.

Fe-content: 8.03% [m/m]

Example 67

Tris-(N-cyclopentyl-3-oxobutanamide)-iron(III)-complex

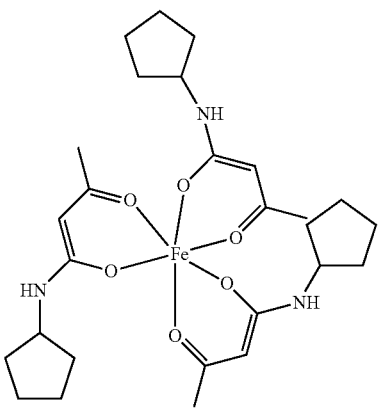

To a solution of 31.3 g (18.50 mmol) N-cyclopentyl-3-oxobutanamide in 40 ml of ethanol, a solution of 1.00 g (6.17 mmol) iron(III)chloride (anhydrous) in 10 ml ethanol was added dropwise. Then 6.22 g (74.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.74 g of a brown solid.

IR (neat, cm$^{-1}$): 3256, 2956, 2869, 1550, 1491, 1450, 1409, 1357, 1265, 1185, 1042, 1015, 951, 780.

Fe-content: 9.17% [m/m].

Example 68

Tris-(1-(pyrrolidin-1-yl)butane-1,3-dione)-iron(III)-complex

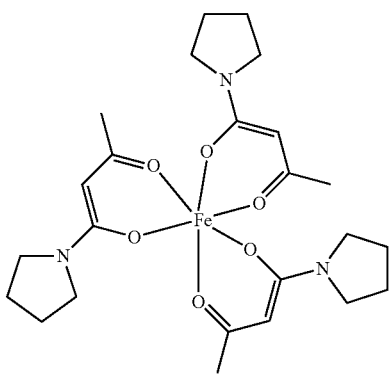

To a solution of 2.87 g (18.50 mmol) 1-(pyrrolidine-1-yl)butane-1,3-dione in 40 ml of ethanol, a solution of 1.00 g (6.17 mmol) iron(III)chloride (anhydrous) in 10 ml ethanol was added dropwise. Then 6.22 g (74.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.41 g of a brown solid.

IR (neat, cm$^{-1}$): 2966, 2869, 1556, 1511, 1473, 1457, 1351, 1328, 1224, 1206, 1117, 1080, 996, 971, 953, 761.

Fe-content: 10.16% [m/m].

Example 69

Tris-(methyl-N-(3-oxobutanoyl)-L-serinate)-iron(III)-complex

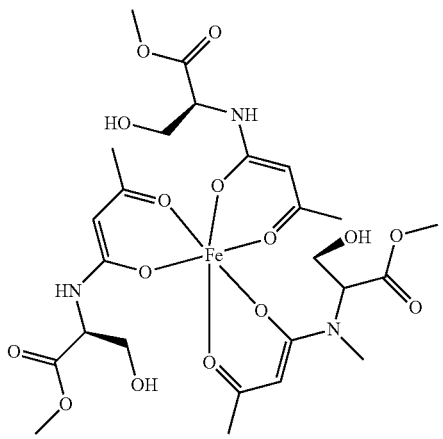

To a solution of 3.75 g (18.50 mmol) of methyl N-(3-oxobutanoyl)-L-serinate in 50 ml of ethanol, a solution of 1.00 g (6.17 mmol) iron(III)chloride (anhydrous)) in 10 ml ethanol was added dropwise. Then 3.11 g (37.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 4.45 g of a brown solid.

IR (neat, cm$^{-1}$): 3285, 2955, 1733, 1543, 1491, 1408, 1343, 1274, 1209, 1186, 1146, 1077, 1054, 1029, 958, 779.

Fe-content: 8.02% [m/m].

Example 70

Tris-(1-(4-acetylpiperazine-1-yl)butane-1,3-dione)-iron(III)-complex

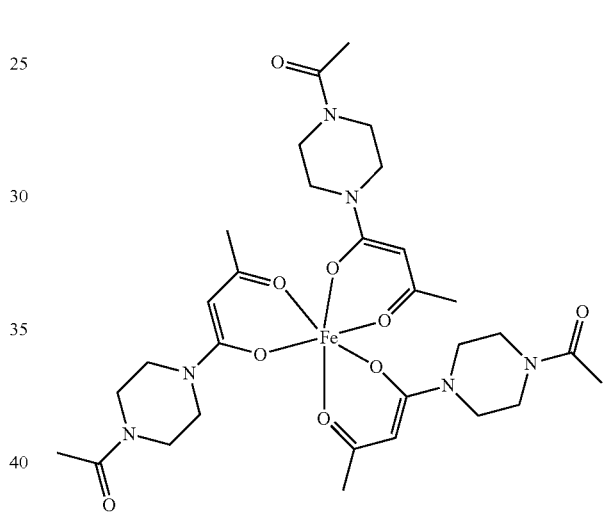

To a solution of 3.92 g (18.50 mmol) 1-(4-acetylpiperazine-1-yl)butane-1,3-dione in 80 ml MeOH, a solution of 1.00 g (6.17 mmol) iron(III)chloride (anhydrous) in 20 ml MeOH was added dropwise. Then 3.11 g (37.00 mmol) of sodium bicarbonate was added in portions. After stirring for 1 h at room temperature, the reaction mixture was evaporated, the residue taken up in 200 ml dichloromethane, stirred for 15 minutes, filtered, and the filtrate was evaporated. The residue was taken up in 50 ml EtOH, evaporated again and the resulting residue was dried overnight in a drying oven. This gave 4.1 g of a brown solid.

IR (neat, cm$^{-1}$): 2914, 1637, 1555, 1511, 1468, 1421, 1367, 1284, 1239, 1172, 1046, 981, 958, 760.

Fe-content: 7.74% [m/m].

Example 71

Tris-(N-cyclohexyl-3-oxobutanamide)-iron(III)-complex

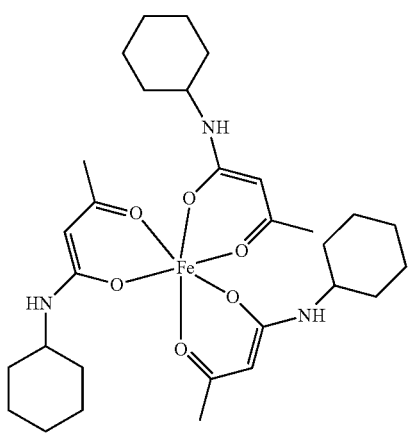

To a solution of 3.39 g (18.50 mmol) N-cyclohexyl-3-oxobutanamide in 40 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 3.8 g of a brown solid.

IR (neat, cm$^{-1}$): 3282, 2928, 2854, 1552, 1488, 1448, 1408, 1315, 1278, 1256, 1187, 1150, 1109, 1041, 975, 942, 781.

Fe-content: 8.81% [m/m].

Example 72

Tris-(methyl-N-(3-oxobutanoyl)glycinate)-iron(III)-complex

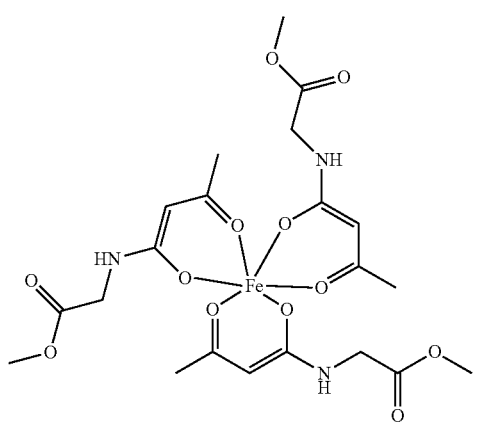

To a solution of 3.21 g (18.50 mmol) of methyl N-(3-oxobutanoyl)glycinate in 40 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 1 h at room temperature, the reaction mixture was filtered, washed with 10 ml of ethanol, the filtrate was evaporated and the residue was dried overnight in an oven at 50° C. This gave 3.95 g of a brown oil.

IR (neat, cm$^{-1}$): 3343, 2955, 1739, 1543, 1495, 1409, 1365, 1284, 1179, 1051, 1011, 988, 779.

Fe-content: 8.95% [m/m].

Example 73

Tris-(N-(2-methylpropyl)-3-oxobutanamide)-iron(III)-complex

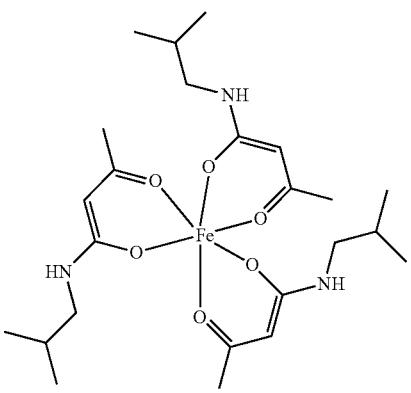

To a solution of 2.90 g (18.50 mmol) N-(2-methylpropyl)-3-oxobutanamide in 40 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 4 h at room temperature, the reaction mixture was filtered, washed with 10 ml of ethanol, the filtrate was evaporated and the residue was dried overnight in an oven at 50° C. This gave 3.49 g of a brown solid.

IR (neat, cm$^{-1}$): 3284, 3110, 2959, 2927, 2871, 1551, 1499, 1433, 1408, 1271, 1188, 1156, 1102, 1018, 954, 940, 777.

Fe-content: 9.70% [m/m].

Example 74

Tris-(N-(cyclopropylmethyl)-3-oxobutanamide)-iron(III)-complex

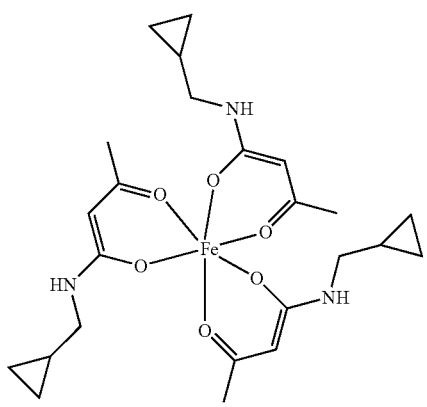

To a solution of 1.44 g (9.25 mmol) N-(cyclopropylmethyl)-3-oxobutanamide in 20 ml of ethanol, a solution of 0.5 g (3.08 mmol) iron(III)chloride (anhydrous) in 10 ml ethanol was added dropwise. Then 1.56 g (18.50 mmol) of sodium bicarbonate was added in portions. After stirring for 4 h at room temperature, the reaction mixture was filtered, washed with 10 ml of ethanol, the filtrate was evaporated and the residue was dried overnight in an oven at 50° C. This gave 1.75 g of a brown solid.

IR (neat, cm$^{-1}$): 3270, 1549, 1498, 1431, 1407, 1265, 1187, 1165, 1096, 1023, 951, 830, 778.

Fe-content: 9.89% [m/m].

Example 75

Tris-(ethyl 4-(morpholin-4-yl)-2,4-dioxobutanoate)-iron(III)-complex

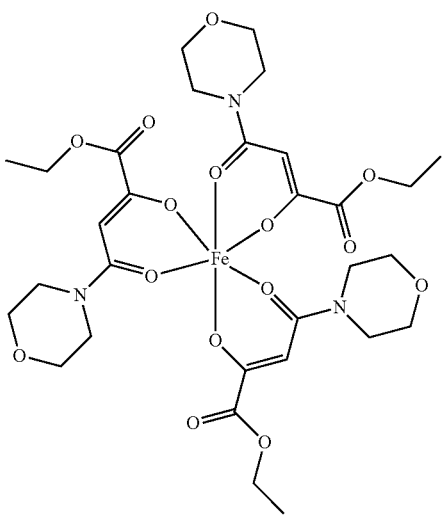

0.24 g (1.45 mmol) iron(III)chloride were dissolved in 20 ml THF and 1.00 g (4.36 mmol) of ethyl 4-(morpholine-4-yl)-2,4-dioxobutanoate was added. After 40 min of stirring, 0.44 g (4.36 mmol) of triethylamine was added and allowed to stir for another 60 min at room temperature. Then 4.6 g 6% sodium ethoxide solution (4.4 mmol) was added dropwise and the solution was stirred for another 2 hours. The precipitated salt was filtered off and the filtrate was concentrated on a rotary evaporator to dryness. The residue was dried 1 day at 50° C. in high vacuum. This gave 0.8 g product as an orange solid.

IR (neat, cm$^{-1}$): 2978, 2923, 2863, 1704, 1610, 1568, 1511, 1442, 1375, 1300, 1275, 1246, 1138, 1111, 1062, 1018, 946, 860, 759, 722, 651.

Elemental analysis: C, 48.54%, H, 5.8%, N, 5.48%.

Fe-content: 6.9% [m/m].

Example 76

Tris-(ethyl N-(3-oxobutanoyl)-L-alaninate)-iron(III)-complex

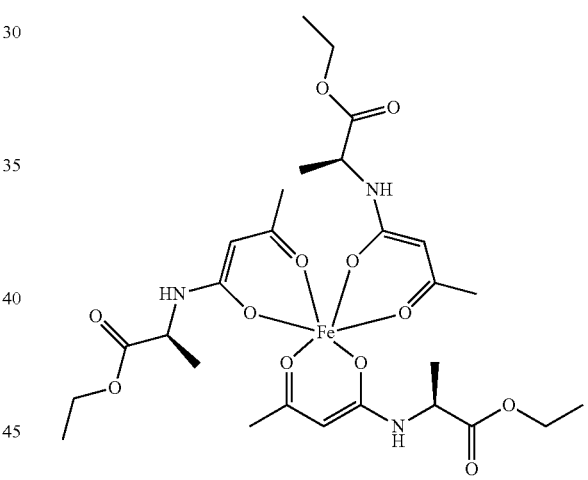

To a solution of 3.72 g (18.50 mmol) of ethyl N-(3-oxobutanoyl)-L-alaninate in 40 ml of ethanol, a solution of 1.00 g (6.17 mmol) iron(III)chloride (anhydrous) in 10 ml ethanol was added dropwise. Then 3.11 g (37.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 4.00 g of a brown oil.

IR (neat, cm$^{-1}$): 3348, 2981, 1733, 1658, 1589, 1539, 1490, 1448, 1411, 1300, 1206, 1186, 1155, 1051, 965, 777.

Fe-content: 7.80% [m/m].

Example 77

Tris-(N-cyclobutyl-3-oxobutanamide)-iron(III)-complex

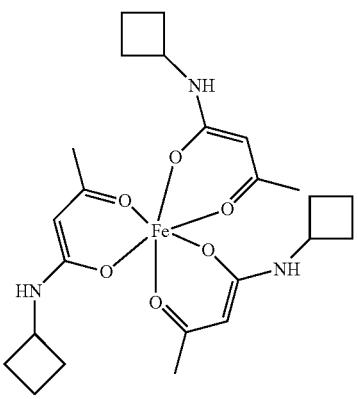

To a solution of 1.43 g (9.25 mmol) N-cyclobutyl-3-oxobutanamide in 20 ml of ethanol, a solution of 0.5 g (3.08 mmol) iron(III)chloride (anhydrous) in 10 ml ethanol was added dropwise. Then 1.56 g (18.50 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 1.71 g of a brown solid.

IR (neat, cm$^{-1}$): 3280, 2978, 2943, 1546, 1488, 1408, 1274, 1187, 1156, 1031, 970, 946, 779, 757.

Fe-content: 9.98% [m/m].

Example 78

Tris-(1-(azetidine-1-yl)butane-1,3-dione)-iron(III)-complex

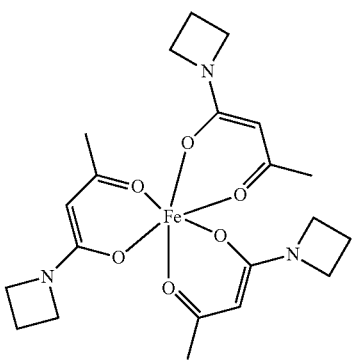

To a solution of 1.30 g (9.25 mmol) 1-(azetidine-1-yl)butane-1,3-dione in 20 ml of ethanol, a solution of 0.5 g (3.08 mmol) of iron(III)chloride (anhydrous) in 10 ml ethanol was added dropwise. Then 3.11 g (37.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 1.58 g of a brown solid.

IR (neat, cm$^{-1}$): 2945, 2878, 1558, 1510, 1473, 1344, 1297, 1201, 1003, 948, 753.

Fe-content: 11.13% [m/m].

Example 79

Tris-(ethyl 1-(3-oxobutanoyl)-piperidine-4-carboxylate)-iron(III)-complex

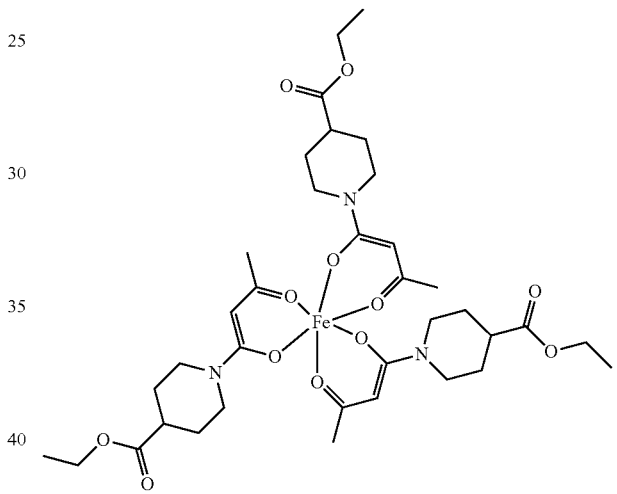

To a solution of 2.23 g (9.25 mmol) of ethyl 1-(3-oxobutanoyl)-piperidine-4-carboxylate in 30 ml of ethanol, a solution of 0.5 g (3.08 mmol) iron(III)chloride (anhydrous) in 10 ml ethanol was added dropwise. Then 3.11 g (37.00 mmol) of sodium bicarbonate was added in portions. After stirring for 2 h at room temperature, the reaction mixture was filtered, washed with 10 ml of ethanol, the filtrate was evaporated and the residue was dried overnight in an oven at 50° C. This gave 2.43 g of a brown solid.

IR (neat, cm$^{-1}$): 2957, 2931, 2862, 1724, 1639, 1555, 1511, 1485, 1446, 1372, 1312, 1271, 1236, 1174, 1038, 973, 958, 760.

Fe-content: 6.67% [m/m].

Example 80

Tris-(1-(4-Hydroxypiperidin-1-yl)-4-methoxybutane-1,3-dione)-iron(III)-complex

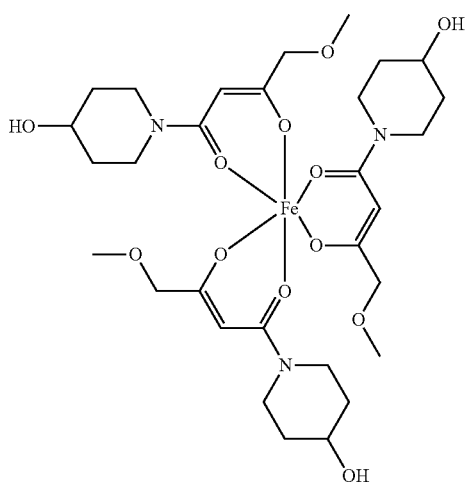

18 mmol (3.91 g) 1-(4-hydroxypiperidine-1-yl)-4-methoxybutane-1,3-dione and 6 mmol (0.96 g), FeCl$_3$ (anhydrous) were dissolved in 80 ml ethanol (anhydrous) and 4 ml of sodium methoxide solution (30% m/m) was added. It was stirred for 1 h and the reaction solution was filtered. The filtrate was concentrated on a rotary evaporator and the product was dried. This gave 4.36 g of the title compound.

IR (neat, cm$^{-1}$): 2928, 2824, 1727, 1597, 1564, 1513, 1491, 1445, 1385, 1331, 1265, 1227, 1197, 1109, 1074, 1051, 1025, 990, 957, 845, 807, 765, 723, 653.

Fe-content: 7.11% [m/m].

The invention claimed is:

1. A medicament, containing
iron (III) complex compounds having the formula

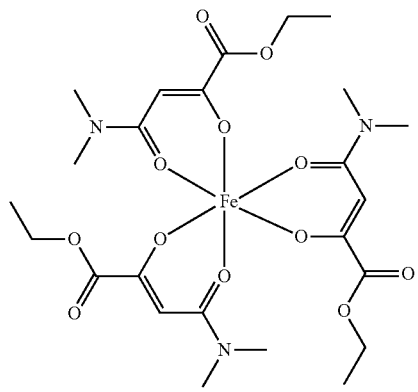

or pharmaceutically acceptable salts thereof.

2. The medicament of claim 1 further comprising at least one physiologically compatible carrier or excipient.

3. A composition, containing
iron (III) complex compounds having the formula

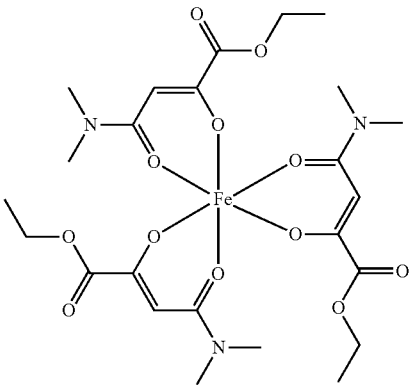

or pharmaceutically acceptable salts thereof, in combination with at least one further medicament which acts on iron metabolism.

4. A composition, containing iron (III) complex compounds having the formula

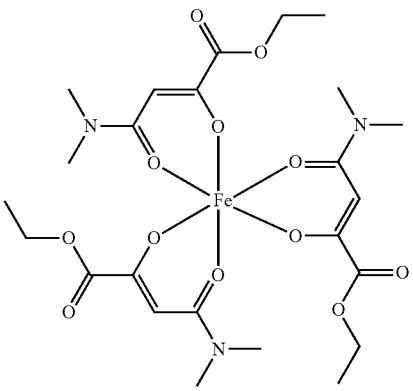

or pharmaceutically acceptable salts thereof.

5. An iron (III) complex compound having the formula

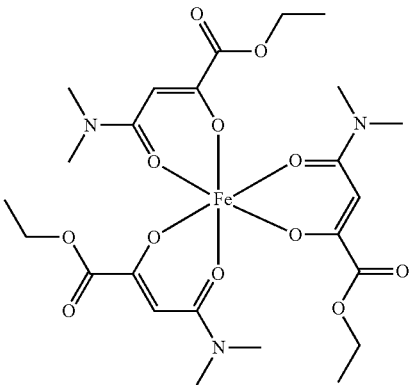

or pharmaceutically acceptable salts thereof.

* * * * *